US006960437B2

(12) United States Patent
Enzelberger et al.

(10) Patent No.: US 6,960,437 B2
(45) Date of Patent: Nov. 1, 2005

(54) NUCLEIC ACID AMPLIFICATION UTILIZING MICROFLUIDIC DEVICES

(75) Inventors: Markus M. Enzelberger, Esslingen (DE); Jian Liu, Pasadena, CA (US); Stephen R. Quake, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 528 days.

(21) Appl. No.: 10/118,466

(22) Filed: Apr. 5, 2002

(65) Prior Publication Data

US 2003/0008308 A1 Jan. 9, 2003

Related U.S. Application Data

(60) Provisional application No. 60/281,960, filed on Apr. 6, 2001, provisional application No. 60/300,516, filed on Jun. 22, 2001, and provisional application No. 60/334,473, filed on Nov. 16, 2001.

(51) Int. Cl.[7] .......................... C12Q 1/68; C12P 19/34; C12M 3/00
(52) U.S. Cl. ...................... 435/6; 435/91.2; 435/287.2; 435/287.3
(58) Field of Search ........................ 435/6, 91.2, 287.2, 435/287.3

(56) References Cited

U.S. PATENT DOCUMENTS

| 3,570,515 | A | 3/1971 | Kinner |
| 3,747,628 | A | 7/1973 | Holster et al. |
| 4,046,159 | A | 9/1977 | Pegourie |
| 4,119,368 | A | 10/1978 | Yamazaki |
| 4,153,855 | A | 5/1979 | Feingold |
| 4,245,673 | A | 1/1981 | Bouteille et al. |
| 4,344,064 | A | 8/1982 | Bitler et al. |
| 4,434,704 | A | 3/1984 | Surjaatmadja |

(Continued)

FOREIGN PATENT DOCUMENTS

| DE | 299 17 313 U1 | 2/2001 |
| EP | 0 579 997 A1 | 1/1994 |
| EP | 592 094 A2 | 4/1994 |
| EP | 703 364 A1 | 3/1996 |
| EP | 706 004 A2 | 4/1996 |
| EP | 779 436 A2 | 6/1997 |
| EP | 829 360 A2 | 3/1998 |
| EP | 845 603 A1 | 6/1998 |
| EP | 999 055 A2 | 10/2000 |
| GB | 2 155 152 A | 9/1985 |
| GB | 2 308 460 A | 6/1997 |
| WO | WO 90/015070 A1 | 12/1990 |
| WO | WO 92/016657 A1 | 10/1992 |
| WO | WO 97/27324 A1 | 7/1997 |
| WO | WO 98/00231 A1 | 1/1998 |
| WO | WO 98/04742 A1 | 2/1998 |
| WO | WO 98/07069 A1 | 2/1998 |

(Continued)

OTHER PUBLICATIONS

Axelrod, Daniel "Cell–Substrate Contacts Illuminated by Total Internal Reflection Fluorescence" Journal of Cell Biology, Apr. 1981, pp. 141–145, vol. 89.

(Continued)

Primary Examiner—Kenneth R. Horlick
(74) Attorney, Agent, or Firm—Townsend and Townsend and Crew LLP

(57) ABSTRACT

The present invention provides microfluidic devices and methods using the same in various types of thermal cycling reactions. Certaom devices include a rotary microfluidic channel and a plurality of temperature regions at different locations along the rotary microfluidic channel at which temperature is regulated. Solution can be repeatedly passed through the temperature regions such that the solution is exposed to different temperatures. Other microfluidic devices include an array of reaction chambers formed by intersecting vertical and horizontal flow channels, with the ability to regulate temperature at the reaction chambers. The microfluidic devices can be used to conduct a number of different analyses, including various primer extension reactions and nucleic acid amplification reactions.

48 Claims, 19 Drawing Sheets

U.S. PATENT DOCUMENTS

| | | |
|---|---|---|
| 4,707,237 A | 11/1987 | Lepp et al. |
| 4,898,582 A | 2/1990 | Faste |
| 5,085,562 A | 2/1992 | van Lintel |
| 5,088,515 A | 2/1992 | Kamen |
| 5,091,652 A | 2/1992 | Mathies et al. |
| 5,096,388 A | 3/1992 | Weinberg |
| 5,126,115 A | 6/1992 | Fujita et al. |
| 5,164,558 A | 11/1992 | Huff et al. |
| 5,171,132 A | 12/1992 | Miyazaki et al. |
| 5,224,843 A | 7/1993 | van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,304,487 A | 4/1994 | Wilding et al. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom et al. |
| 5,400,741 A | 3/1995 | DeTitta et al. |
| 5,423,287 A | 6/1995 | Usami et al. |
| 5,529,465 A | 6/1996 | Zengerle et al. |
| 5,593,130 A | 1/1997 | Hansson et al. |
| 5,639,423 A | 6/1997 | Northrup et al. |
| 5,642,015 A | 6/1997 | Whitehead et al. |
| 5,646,039 A | 7/1997 | Northrup et al. |
| 5,659,171 A | 8/1997 | Young et al. |
| 5,660,370 A | 8/1997 | Webster |
| 5,674,742 A | 10/1997 | Northrup et al. |
| 5,681,024 A | 10/1997 | Lisec et al. |
| 5,705,018 A | 1/1998 | Hartley |
| 5,759,014 A | 6/1998 | Van Lintel |
| 5,775,371 A | 7/1998 | Pan et al. |
| 5,802,856 A | 9/1998 | Schaper et al. |
| 5,832,165 A | 11/1998 | Reichert et al. |
| 5,836,750 A | 11/1998 | Cabuz |
| 5,842,787 A | 12/1998 | Kopf-Sill et al. |
| 5,846,396 A | 12/1998 | Zanzucchi et al. |
| 5,858,195 A | 1/1999 | Ramsey |
| 5,863,722 A | 1/1999 | Brenner |
| 5,875,817 A | 3/1999 | Carter |
| 5,876,187 A | 3/1999 | Afromowitz et al. |
| 5,876,675 A | 3/1999 | Kennedy |
| 5,876,946 A | 3/1999 | Burbaum et al. |
| 5,888,778 A | 3/1999 | Shuber |
| 5,922,591 A | 7/1999 | Anderson et al. |
| 5,922,604 A | 7/1999 | Stapelton et al. |
| 5,928,880 A | 7/1999 | Wilding et al. |
| 5,932,799 A | 8/1999 | Moles |
| 5,942,443 A | 8/1999 | Parce et al. |
| 5,958,344 A | 9/1999 | Levine et al. |
| 5,972,639 A | 10/1999 | Parandoosh |
| 5,976,822 A | 11/1999 | Landrum et al. |
| 6,004,515 A | 12/1999 | Parce et al. |
| 6,007,309 A | 12/1999 | Hartley |
| 6,007,690 A | 12/1999 | Nelson et al. |
| 6,015,531 A | 1/2000 | Colin et al. |
| 6,018,616 A | 1/2000 | Schaper |
| 6,043,080 A | 3/2000 | Lipshutz et al. |
| 6,046,056 A | 4/2000 | Parce et al. |
| 6,048,498 A | 4/2000 | Kennedy |
| 6,062,261 A | 5/2000 | Jacobson et al. |
| 6,094,274 A | 7/2000 | Yokoi |
| 6,103,537 A | 8/2000 | Ullman et al. |
| 6,107,044 A | 8/2000 | Nikiforov |
| 6,123,769 A | 9/2000 | Sanjoh |
| 6,132,580 A | 10/2000 | Mathies et al. |
| 6,132,685 A | 10/2000 | Kercso et al. |
| 6,136,212 A | 10/2000 | Mastrangelo et al. |
| 6,146,842 A | 11/2000 | Josiah et al. |
| 6,150,119 A | 11/2000 | Kopf-Sill et al. |
| 6,150,180 A | 11/2000 | Parce et al. |
| 6,155,282 A | 12/2000 | Zachary et al. |
| 6,165,694 A | 12/2000 | Liu |
| 6,167,910 B1 | 1/2001 | Chow |
| 6,171,850 B1 | 1/2001 | Nagle et al. |
| 6,174,365 B1 | 1/2001 | Sanjoh |
| 6,174,675 B1 | 1/2001 | Chow et al. |
| 6,197,595 B1 | 3/2001 | Anderson et al. |
| 6,214,246 B1 | 4/2001 | Craighead |
| 6,221,654 B1 | 4/2001 | Quake et al. |
| 6,225,109 B1 | 5/2001 | Juncosa et al. |
| 6,227,809 B1 | 5/2001 | Forster et al. |
| 6,235,471 B1 | 5/2001 | Knapp et al. |
| 6,296,673 B1 | 10/2001 | Santarsiero et al. |
| 6,306,659 B1 | 10/2001 | Parce et al. |
| 6,321,791 B1 | 11/2001 | Chow |
| 6,344,325 B1 | 2/2002 | Quake et al. |
| 6,355,420 B1 | 3/2002 | Chan |
| 6,361,671 B1 | 3/2002 | Mathies et al. |
| 6,408,878 B2 | 6/2002 | Unger et al. |
| 6,540,895 B1 | 4/2003 | Quake et al. |
| 6,767,706 B2 * | 7/2004 | Quake et al. ................ 435/6 |
| 2001/0027745 A1 | 10/2001 | Weigl et al. |
| 2001/0041357 A1 * | 11/2001 | Fouillet et al. ............ 435/91.1 |
| 2002/0124896 A1 | 9/2002 | O'Connor et al. |
| 2003/0138829 A1 | 7/2003 | Unger et al. |
| 2003/0196695 A1 | 10/2003 | O'Connor et al. |

FOREIGN PATENT DOCUMENTS

| | | |
|---|---|---|
| WO | WO 98/45481 A1 | 10/1998 |
| WO | WO 99/14311 A1 | 3/1999 |
| WO | WO 99/17093 A1 | 4/1999 |
| WO | WO 99 41015 | 8/1999 |
| WO | WO 99/61888 A2 | 12/1999 |
| WO | WO 00/53801 A1 | 9/2000 |
| WO | WO 00/60345 A1 | 10/2000 |
| WO | WO 00/68414 A2 | 11/2000 |
| WO | WO 00/70082 A1 | 11/2000 |
| WO | WO 01/001025 A2 | 1/2001 |
| WO | WO 01/07061 A1 | 2/2001 |
| WO | WO 01/24937 A2 | 4/2001 |
| WO | WO 01/32930 A1 | 5/2001 |
| WO | WO 02/00343 A2 | 1/2002 |
| WO | WO 02/29106 A2 | 4/2002 |
| WO | WO 02/30486 A2 | 4/2002 |
| WO | WO 02/40874 A1 | 5/2002 |
| WO | WO 02/43615 A2 | 6/2002 |
| WO | WO 02/065005 A1 | 8/2002 |
| WO | WO 02/072892 A1 | 9/2002 |
| WO | WO 02/081729 A2 | 10/2002 |
| WO | WO 02/081935 A2 | 10/2002 |
| WO | WO 03/048295 A1 | 6/2003 |

OTHER PUBLICATIONS

Chou, H. et al., "Disposable Microdevices for DNA Analysis and Cell Sorting", Proc. Solid–State Sensor and Actuator Workshop, Hilton Head, SC, Jun. 8–11, 1998, pp. 11–14.

Chou, H.P. et al., "Microfabricated devices for sizing DNA and sorting cells," in Micro– and Nanofabricated Structures and Devices for Biomedical Environmental Applications, Paul L. Gourley, Editor, Proceedings of SPIE, 1998, pp. 181–187, vol. 3258.

Fu et al.; "A microfabricated fluorescence–activated cell–sorter", Nature Biotechnology, 1999, pp. 1109–1111, vol. 17.

Gonzalez, J.E. & Tsien, R. "Improved indicators of cell membrane potential that use fluorescence resonance energy transfer", Chem. Biol., 1997, pp. 269–277, vol. 4, No. 4.

Hermanson, G.T. et al. Immobilized Affinity Ligand Techniques, 1992, Chapter 2, Academic Press, San Diego, U.S.A.

Jacobson, K. et al.; "International Workshop on the Application of Fluorescence Photobleaching Techniques to Problems in Cell Biology", Workshop Summary, Federation Proceedings, 1983, pp. 72–79, vol. 42.

Levine, L.M. et al. "Measurement of specific protease activity utilizing fluorescence polarization", Anal. Biochem., 1997, pp. 83–88, vol. 247, No. 1.

Llopis, J. et al. "Ligand–dependent interactions of coactivators steroid receptor coactivator–1 and peroxisome proliferator–activated receptor binding protein with nuclear hormone receptors can be imaged in live cells and are required for transcription", Proc. Natl. Acad. Sci. U.S.A., 2000, pp. 4363–4368, vol. 97, No. 8.

Mahajan, N.P. et al. "Novel mutant green fluorescent protein protease substrates reveal the activation of specific caspases during apoptosis", Chem. Biol., 1999, pp. 401–409, vol. 6, No. 6.

Moreno Davila, H. "Molecular and functional diversity of voltage–gated calcium channels", Molecular and Functional Diversity of Ion Channels and Receptors. Ann N. Y. Acad. Sci., 1999, pp. 102–117, vol. 868.

Nagai, Y. et al. "A fluorescent indicator for visualizing cAMP–induced phosphorylation in vivo." Nat Biotechnol., 2000, pp. 313–316, vol. 18, No. 3.

Parker, G.J. et al. "Development of high throughput screening assays using fluorescence polarization: nuclear receptor–ligand–binding and kinase*/phophatase assays", J. Biomol. Screen., 2000, pp. 77–88, vol. 5, No. 2.

Seethala, R. & Menzel, R. "A fluorescence polarization competition immunoassay for tyrosine kinases", Anal. Biochem. , 1998, pp. 257–262, vol. 255, No. 2.

Takahashi, A. et al., "Measurement of Intracellular Calcium", Physiol. Rev., 1999, pp. 1089–1125, vol. 79, No. 4.

Unger, Marc A. et al. "Single–molecule fluorescence observed with mercury lamp illumination", Biotechniques, Nov. 1999, p. 1008–1014, vol. 27, No. 5

Van De Pol, F.C.M. et al. "A Thermo–Pneumatic Actuation Principle for a Microminiature Pump and Other Micromechanical Devices" Sensors and Actuators, May 3, 1989, pp. 139–143, vol. 17, Nos. 1–2.

Xu, X. et al. "Detection of programmed cell death using fluorescence energy transfer", Nucleic Acids Res. , 1998, pp. 2034–2035, vol. 26, No. 8.

Zaccolo, M. et al. "A genetically encoded, fluorescent indicator for cyclic AMP in living cells", Nat Cell Biol, 2000, pp. 25–29, vol. 2, No. 1.

Zdeblick et al. "A Microminiature Electric–to–Fluidic Valve", Transducers '87, Proceedings of the 4th International Conference on Solid–State Sensors and Actuators. Reprinted in Micromechanics and MEMS Classic and Seminal Papers to 1990, 1987, pp. 437–439, IEEE Press, USA.

Ahn et al., "Fluid Micropumps Based on Rotary Magnetic Actuators," Proceedings of 1995 IEEE Micro Electro Mechanical Systems, Workshop ( MEMS '95), held in Amsterdam, Netherlands on Jan. 29–Jan. 2, 1995, pp. 408–412 (1995).

Applied Biosystems, "TaqMan® PCR Reagent Kit with AmpliTaq Gold® DNA Polymerase Protocol," Jan. 2003, Published in the U.S.A.

Blegrader et al., "PCR Detection of Bacteria in Seven Minutes," Science, 284(5413):449–450 (1999).

Belgrader et al., "A Battery–Powered Notebook Thermal Cycler for Rapid Multiplex Real–Time PCR Analysis," Anal. Chem., 73:286–289 (2001).

Benard et al., "A Titanium–Nickel Shape–Memory Alloy Actuated Micropump," Proceedings of Transducers '97, 1997 International Conference on Solid–State Sensors and Actuators, held in Chicago, Il., Jun. 16–19, 1997, 1:361–364 (1997).

Brechtel et al., "Control of the electroosmotic flow by metal–salt–containing buffers," J. Chromatography A, 716:97–105 (1995).

Bryzek et al., "Micromachines on the march," 8045 IEEE Spectrum, 31(5):20–31 (1994). XP 000456261.

Buchaillot et al., "Silicon Nitride Thin Films Young's Modulus Determination by an Optical Non–Destructive Method," Jpn. J. Appl. Phys., 36 Pt. 2 (6B):L794–L797 (1997).

Burns et al., "An Integrated Nanoliter DNA Analysis Device," Science, 282:484–487 (1998).

Chaudhari et al., "Transient Liquid Crystal Thermometry of Microfabricated PCR Vessel Arrays," J. Microelectromechanical Systems, 7(4):345–355 (1998).

Chiu et al., "Patterned deposition of cells and proteins onto surfaces by using three–dimensional microfluidic systems", PNAS, 97(6):2408–2413 (2000).

Chiou et al., "A Closed–Cycle Capillary Polymerase Chain," Anal. Chem., 73:2018–2021 (2001).

Chou et al., "A microfabricated device for sizing and sorting DNA molecules," PNAS, 96:11–13 (1999).

Chou et al., "A Microfabricated Rotary Pump," Biomedical Microdevices, 3(4):323–330 (2001).

Chou et al., "Integrated Elastomer Fluidic Lab–on–a–chip–Surface Patterning and DNA Diagnostics," Proceedings of the Solid State Actuator and Sensor Workshop, held in Hilton Head South Carolina in 2000.

Delamarche et al., "Patterned Delivery of Immunoglobulins to Surfaces Using Microfluidic Networks," Science, 276:779–781 (1997).

Duffy et al., "Rapid Prototyping of Microfluidic Systems in Poly(dimethylsiloxane)", Analytical Chemistry, 70(23):4974–4984 (1998).

Duffy et al., "Rapid prototyping of microfluidic switches in poly(dimethyl siloxane) and their actuation by electro–osmotic flow," J. Micromech. Microeng., 9:211–217 (1999).

Duffy et al., "Patterning Electroluminescence Materials with Feature Sizes as Small as 5 µm Using Elastomeric Membranes as Masks for Dry Lift–Off," Adv. Mater., 11(7):546–552 (1999). XP–000849014.

Effenhauser et al., "Integrated Capillary Electrophoresis on Flexible Silicone Microdevices; Analysis of DNA Restriction Fragments and Detection of Single DNA Molecules on Microchips," Anal. Chem., 69(17):3451–3457 (1997).

Effenhauser et al., "Integrated chip–based capillary electrophoresis," Electrophoresis, 18:2203–2213 (1997).

Erlich, H.A., PCR Technology, pp. 1–5, Stockton Press, New York (1989).

Fahrenberg et al., "A microvalve system fabricated by thermoplastic molding," J. Micromech. Microeng., 5:169–171 (1995).

Fu et al., "An Integrated Microfabricated Cell Sorter," Analytical Chemistry.

Gass et al., "Integrated flow–regulated silicon micropump," Sensors and Actuators A, 43335–338 (1994).

Gerlach, T., "Pumping Gases by a Silicon Micro Pump with Dynamic Passive Valves," *Proceedings of Transducers '97, 1997 International Conference on Solid–State Sensors and Actuators*, held in Chicago, Il., Jun. 16–19, 1997, 1:357–360 (1997).

Goll et al., "Microvalves with bistable buckled polymer diaphragms," *J. Micromech. Microeng.*, 6:77–79 (1996).

Graveson et al., "Microfluidics—a review", *J. Micromech. Microeng.* 3:168–182 (1993).

Harrison et al., "Micromachining a Miniaturized Capillary Electrophoresis–Based Chemical Analysis System on a Chip," *Science*, 261:895–897 (1993).

Hong et al., "Integration of gene amplification and capillary gel electrophoresis on a polydimethylsiloxane–glass hybrid microchip," *Electrophoresis 2001*, 22:328–333 (2001).

Hornbeck et al., "Bistable Deformable Mirror Device," *Spatial Light Modulators and Applications 1988 Technical Digest Series, vol. 8*, Postconference Edition, Summaries of papers presented at the Spatial Light Modulators and Applications Topical Meeting, Jun. 15–17, 1988, Optical Society of America, pp. 107–110.

Hosokawa et al., "Handling of Picoliter Liquid Samples in a Poly(dimethylsiloxane)–Based Microfluidic Device," *Anal. Chem.*, 71(20):4781–4785 (1999).

Ibrahim et al., "Real–Time Microchip PCR for Detecting single–Base differences in Viral and Human DNA," *Anal. Chem.*, 70:2013–2017 (1998).

Ikuta et al., "Three dimensional micro integrated fluid systems, (MIFS) fabricated by stereo lithography," *IEEE Kyushu Institute of Technology*, pp. 1–6 (1994).

Jacobson et al., "High–speed separations on a microchip," *Anal. Chem.*, 66(7):1114–1118 (1994).

Jacobson et al., "Microfluidic Devices for Electrokinetically Driven Parallel and Serial Mixing," *Anal. Chem.*, 71(20):4455–4459 (1999).

Jerman, H., "Electrically–Activated, Normally–Closed Diaphragm Valves," *Proceedings of Transducers '91, 1991 International Conference on Solid–State Sensors and Actuators*, pp. 1045–1048 (1991).

Jung et al., "Chemical and Physical Interactions at Metal/Self–Assembled Organic Monolayer Interfaces," *Critical Reviews in Solid State and Material Sciences*, 19(1):2–10 (1994).

Kenis et al., "Microfabrication Inside Capillaries Using Multiphase Laminar Flow Patterning," *Science*, 285:83–85 (1999).

Khandurina et al., "Integrated System for Rapid PCR–Based DNA Analysis in Microfluidic Devices," *Anal. Chem.*, 72:2995–3000 (2000).

Kopp et al., "Chemical Amplification: Continuous–Flow PCR on a Chip", *Science*, 280:1046–1048 (1998).

Kuhn et al., "Silicon Charge Electrode Array for Ink Jet Printing", *IEEE Transactions on Electron Devices*, ED–25(10):1257–1260 (1978).

Lagally et al., "Single–Molecule DNA Amplification and Analysis in an Integrated Microfluidic Device," *Anal. Chem.*, 73:565–570 (2001).

Lin et al., "Free–Space Micromachined Optical Switches for Optical Networking," *IEEE J. Selected Topics in Quantum Electronics*, 5(1):4–9 (1999).

Lötters et al., "The mechanical properties of the rubber elastic polymer polydimethylsiloxane for sensor applications," *J. Micromech. Microeng.*, 7:145–147 (1997).

Lucy et al., "Characterization of the Cationic Surfactant Induced Reversal of Electroosmotic Flow in Capillary Electrophoresis," *Anal. Chem.*, 68:300–305 (1996).

Maluf, N., *An Introduction to Microelectromechanical Systems Engineering*, Artech House Publishers, Boston London pp. 42–45.

Markx et al. "Applications of dielectrophoresis in biotechnology," *Tibtech*, 15:426–432 (1997).

Muller et al., "Surface–Micromachined Microoptical Elements and Systems," *Proceedings of IEEE*, 86(8):1705–1720 (1998).

Nakano et al., "High Speed Polymerase Chain Reaction in Constant Flow," *Biosci. Biotech. Biochem.*, 58(2):349–352 (1994).

Olsson et al., "Simulation Studies of Diffuser and Nozzle Elements for Valve–less Micropumps," *Proceedings of Transducers '97, 1997 International Conference on Solid–State Sensors and Actuators*, held in Chicago, Il., Jun. 16–19, 1997, 2:1039–1042 (1997).

Qin et al., "Elastomeric Light Valves**", *Adv. Mater.*, 9(5):407–410 (1997). XP–000683891.

Qin et al., "Photolithography with transparent reflective photomasks," *J. Vac.Sci. Technology*, 16(1):98–103 (1998).

Quake et al., "From micro– to nanofabrication with soft materials," *Science*, 290(5496):1536–1540 (2000).

Rapp. R., "LIGA micropump for gases and liquids," *Sensors and Actuators A*, 40:57–61 (1994).

Roylance et al., "A Batch–Fabricated Silicon Accelerometer", *IEEE Transactions on Electron Devices*, ED–26(12):1911–1917 (1979).

Schasfoort et al., "Field–Effect Flow Contorl for Microfabricated Fluidic Networks," *Science*, 286:942–945 (1999).

Schueller et al., "Fabrication of glassy carbon microstructures by soft lithography," *Sensors and Actuators*, 72(2):125–139 (1999).

Shoji, S., "Fluids for Sensor Systems", *Topics in Current Chemistry*, 194:162–188 Springer Verlag Berlin Heidelberg (1998).

Shoji et al., "Smallest Dead Volume Microvalves for Integrated Chemical Analyzing Systems," *Proceedings of Transducers '91, 1991 International Conference on Solid–State Sensors and Actuators*, pp. 1052–1055 (1991).

Smits, J.G., "Piezoelectric Micropump with Three Valves Working Peristaltically", *Sensors and Actuators*, A21–A23:203–206 (1990).

Sohn et al., "Capacitance cytometry: Measuring biological cells one by one," *PNAS*, 97(20):10687–10690 (2000).

Tufte et al., "Silicon Diffused–Element Piezoresistive Diaphragms," *J. Appl. Phys.*, 33(11):3322–3327 (1962).

Tyagi et al., "Molecular Beacons: Probes that Fluoresce upon Hybridization," *Nature Biotechnology*, 14:303–308 (1996).

Unger et al., "Monolithic Microfabricated Valves and Pumps by Multilayer Soft Lithography," *Science*, 288:113–116 (2000).

Van der Pol et al., "Micro Liquid Handling Devices—A Review", *Micro Systems, Technologies*, 90:799–805 (1990).

Vieider et al., "A Pneumatically Actuated Micro Valve with a Silicone Rubber Membrane for Integration with Fluid–Handling Systems," *Proceedings of Transducers '95*, the 8th International Conference on Solid–State Sensors and Actuators and Eurosensors IX, held in Stockholm, Sweden on Jun. 25–29, 1995, 2:284–286 (1995).

Washizu et al., "Molecular Dielectrophoresis of Biopolymers," *IEEE Transactions on Industry Applications*, 30(4):835–843 (1994).

Wooley et al., "Functional Integration of PCR Amplification and Capillary Electrophoresis in a Microfabricated DNA Analysis Device," *Anal. Chem.*, 68:4081–4086 (1996).

Xia et al., "Complex Optical Surfaces Formed by Replica Molding Against Elastomeric Masters," *Science*, 273:347–349 (1996).

Xia et al., "Soft Lithography," *Angew. Chem. Int. Ed.* 37:551–575 (1998).

Xia et al., "Micromolding of Polymers in Capillaries: Applications in Microfabrication," *Chemistry of Materials*, 8(7):1558–1567 (1996).

Xia et al., "Micromolding in Capillaries: Applications in Material Science," *J. American Chemical Society*, 118;5722–5731 (1996).

Yang et al., "A Mems Thermopneumatic Silicone Membrane Valve", Proceedings of IEEE 10$^{th}$ Annual International Workshop on MicroElectro Mechanical Systems, *Sensors and Actuators*, A64(1):101–108 (1998).

Yang et al., "A MEMS Thermopneumatic silicone Membrane Valve," *Proceedings of the IEEE 10th Annual Workshop of Micro Electro Mechanical Systems Workshop (MEMS '97)*, held Jan. 26–30, 1997 in Nagoya, Japan, pp. 114–118 (1997).

Yazdi et al., "Micromachined Inertial Sensors," *Proceedings of IEEE*, 86(8):1640–1659 (1998).

Young et al., "Contoured elastic–membrane microvalves for microfluidic network integration," *J. Biomechanical Engineering*, 121:2–6 (1999).

XP–002149046, Ullmann's Encyclopedia of Industrial Chemistry, Sixth Edition, 1999 Electronic Release, 6 pages.

Zengerle et al., "A Micro Membrane Pump with Electrostatic Actuation," *1992 IEEE Conf. on Micro Electro Mechanical Systems,* held Feb. 4–7, 1992, in Travemunde Germany, pp. 19–24.

Zengerle et al., "Performance Simulation of Microminiaturized Membrane Pumps," from 7th International Conference on Solid–State Sensors and Actuators held Jun. 7–10, 1993 in Yokohama Japan, pp. 106–109.

* cited by examiner

NUCLEIC ACID AMPLIFICATION UTILIZING MICROFLUIDIC DEVICES

CROSS-REFERENCE TO RELATED APPLICATIONS

This application claims the benefit of U.S. Provisional Application No. 60/281,960, filed Apr. 6, 2001, U.S. Provisional Application No. 60/300,516, filed Jun. 22, 2001, and U.S. Provisional Application No. 60/334,473, filed Nov. 16, 2001, each of which is incorporated herein by reference in its entirety for all purposes.

STATEMENT REGARDING FEDERALLY SPONSORED RESEARCH

This invention was made with support from Grant Number CTS-0088649 awarded by the National Science Foundation. Therefore, the U.S. government has certain rights in this invention.

FIELD OF THE INVENTION

The present invention relates to microfluidic devices and methods of using the same in various types of thermal cycling reactions.

BACKGROUND OF THE INVENTION

Nucleic acid amplification reactions have emerged as powerful tools in a variety of genetic analyses and diagnostic applications. The value of these techniques is their ability to rapidly increase the concentration of target nucleic acids of interest that might be present at very low and otherwise undetectable levels. For instance, by utilizing the polymerase chain reaction (PCR) amplification technique, one can amplify a single molecule of a target nucleic acid by $10^6$ to $10^9$.

PCR is perhaps the most well-known of a number of different amplification techniques. This well established procedure involves the repetition of heating (denaturation) and cooling (annealing) cycles in the presence of a target nucleic acid, primers that hybridize to the target, deoxynucleotides, a polymerase and cofactors such as metal ions. Each cycle produces a doubling of the amount of the target DNA. The cycles are conducted at characteristic temperatures: 95° C. for denaturing double stranded nucleic acid, 50 to 65° C. for hybridization of primer to the target nucleic acid, and 72 to 77° C. for primer extension (see, generally, Sambrook et al., (1989) Molecular Cloning: A Laboratory Manual, 2nd ed., Cold Spring Harbor Laboratory Press; see also U.S. Pat. Nos. 4,683,202 and 4,683,195, for example).

Methods for conducting PCR amplifications fall into two general classes. The approach typically utilized is a time domain approach in which the amplification reaction mixture is kept stationary and the temperature is cycled (see, e.g., Cheng, et al. (1996) Nucleic Acids Res. 24:380–385; Shoffer, et al. (1996) Nucleic Acids Res. 24:375–379; and Hong, et al. (2001) Electrophoresis 22:328–333). While methods utilizing this approach can be conducted with relatively small sample volumes, the methods require complex regulation of heater elements and relatively long reaction times. Another approach that has been discussed is limited to a space domain approach in which three temperature zones are constantly kept at the different temperatures and the reaction mixture runs in a serpentine flow channel above it (see, e.g., Kopp et al. (1998) Science 280:1046–1048). A method such as this can be conducted at relatively high speed because it is not necessary to heat and cool the heaters, but requires the use of relatively large sample volumes.

SUMMARY OF THE INVENTION

A variety of microfluidic devices and methods for conducting temperature controlled analyses are provided herein. Unlike conventional microfluidic devices, the devices disclosed herein include elastomeric components. In some instances, much of the device is manufactured from elastomeric materials. The devices can be utilized in a wide variety of applications, particularly in analyses involving thermal cycling.

Certain of these microfluidic devices include (a) a substrate comprising an elastomeric material; (b) a flow channel disposed within the substrate, the flow channel being configured such that a sample introduced into the flow channel can be cycled around the flow channel, and comprising a plurality of temperature regions at which temperature can be regulated, each temperature region located at a different location along the flow channel; (c) an inlet in fluid communication with the flow channel via which the sample can be introduced into the flow channel; and (d) a temperature controller operatively disposed to regulate temperature within at least one of the plurality of temperature regions. Devices of this type can also include one or more pumps for transporting fluid through the flow channel. Certain of these pumps comprise one or more control channels, each of the control channels of the pump formed within an elastomeric material and separated from the flow channel by a section of an elastomeric membrane, the membrane being deflectable into or retractable from the substantially circular flow channel in response to an actuation force applied to the control channel. The flow channel in some of these devices is substantially circular. A flow channel of this shape cannot be formed with conventional silicon-based microfluidic devices that utilize electrical current to move solutions through the microfluidic channels.

Still other devices have a different configuration in which the device includes a plurality of reaction chambers disposed along the flow channel and in fluid communication with the flow channel, with each reaction chamber located within one of the temperature regions. Devices of this type can also include a plurality of control channels, each formed within an elastomeric material and separated from one of the reaction chambers by an elastomeric membrane, the membrane being deflectable into one of the reaction chambers in response to an actuation force applied to the control channel. As a result of such actuation, sample can be transported between the reaction chambers. In some instances, the plurality of reaction chambers are in fluid communication such that substantially all of the sample within the plurality of reaction chambers is collected at one of the plurality of reaction chambers upon actuation of the control channels associated with the other reaction chambers.

Other microfluidic devices that are provided herein include (a) a substantially circular microfabricated flow channel in fluid communication with an inlet; (b) a plurality of temperature regions, each region located at a different location along the substantially circular flow channel; and (c) a temperature controller operatively disposed to regulate the temperature within at least one of the plurality of temperature regions.

Methods utilizing devices of the foregoing design are also provided herein. Such methods generally involve providing a microfluidic device such as described above, introducing a sample into the flow channels, and then transporting the sample between the different temperature regions. Such methods can involve introducing a nucleic acid sample and components for conducting a nucleic acid amplification reaction into the flow channel. The sample and the components for the amplification reaction are then repeatedly cycled through the flow channel such that the sample and components are exposed to the temperature regions multiple times and an amplified product is formed. The methods can further involve detection of the amplified product. In some methods, the amplified product bears a detectable label and detection involves detecting the label. Detection in other methods involves contacting the amplified product with a label such that the amplified product becomes labeled. Exemplary labels suitable for such methods include interchelating dyes and molecular beacons. Still other detection schemes involve conducting a quantitative PCR assay, detecting amplified product by gel electrophoresis, or measuring capacitance of a solution containing the amplified product.

Microfluidic devices of the type described above can also be utilized to conduct sequencing reactions. In such methods a nucleic acid sample is introduced into the flow channel together with one or more components required for conducting a sequencing reaction. Quantitative PCR can also be performed with the devices. Such methods involve introducing a nucleic acid and one or more components for conducting a quantitative PCR reaction into the flow channel and then transporting the sample and components through the different temperature regions.

Other microfluidic devices that are disclosed herein have a different design and are in the form of an array or matrix of junctions or reaction chambers located at the intersection of horizontal and vertical flow channels. Microfluidic devices of this type enable a large number of reactions to be conducted simultaneously. Certain of these devices include (a) a substrate comprising an elastomeric material; (b) a first plurality of flow channels formed within the substrate; (c) a second plurality of flow channels, each formed within the substrate and in fluid communication with an inlet, the second flow channels intersecting the first flow channels to define an array of reaction chambers; (d) isolation valves selectively actuatable to block flow between junctions along at least one of the first and second flow channels, and to regulate solution flow to the reaction chambers; (e) a plurality of temperature regions located along each of the second plurality of microfabricated flow channels; and (f) a temperature controller operatively disposed to regulate temperature at one or more of the temperature regions. In certain of these devices, the isolation valves comprise a first and second valve that have differing activation thresholds.

Other devices include (a) a substrate comprising an elastomeric material; (b) a first plurality of flow channels formed within the substrate; (c) a second plurality of flow channels, each formed within the substrate and in fluid communication with an inlet, the second flow channels intersecting the first flow channels to define an array of reaction chambers; and (d) isolation valves selectively actuatable to block flow between junctions along at least one of the first and second flow channels, and to regulate solution flow to the reaction chambers, wherein the isolation valves comprise a first and second isolation valve that have differing activation thresholds. In certain devices, reaction chambers are separated from one another by at least two first isolation valves or at least two second isolation valves.

With array-based microfluidic devices such as just described, the isolation valves can comprise an elastomeric membrane that separates a control channel and the microfabricated flow channel upon which the valve acts, the elastomeric membrane able to be deflected into or retracted from the flow channel upon which it acts in response to an actuation force. Devices of this design can also include one or more pumps to flow solution through the horizontal and/or vertical flow channels. Certain of these pumps comprise one or more control channels, each of the control channels formed within an elastomeric material and separated from one of the horizontal or vertical flow channels by a section of an elastomeric membrane, the membrane being deflectable into or retractable from the horizontal or vertical flow channel upon which it acts in response to an acutation force applied to the control channel.

Array-based devices such as the foregoing can be utilized to conduct diverse types of analyses, including nucleic acid amplification reactions, synthesis reactions and screening analyses. In general such methods involve (a) provding an array-based device such as described above, (b) introducing a sample and one or more reactants into the reaction chambers by selective actuation of one or more of the isolation valves, whereby reaction between the sample and the one or more reactants occurs, and (c) heating regions of the microfluidic device to promote reaction between the sample and the one or more reactants within the reaction chambers. In certain methods, the sample and the one or more reactants are introduced into the first and second plurality of flow channels, and then the isolation valves actuated to allow the sample and the one or more reactants to mix by diffusion within the reaction chambers.

When nucleic acid amplification reactions are performed, the sample is a nucleic acid containing sample and the one or more reactants are reactants required for the particular type of amplification reaction. The heating step promotes reaction between the nucleic acid and the one or more reactants to form an amplified product. The resulting amplified product can be detected according to the methods described above.

Certain methods involve introducing samples and/or one or more of the reactants under pressure. Some of these methods involve positioning the microfluidic device in a holder that is configured to form an air tight chamber over an inlet to each of the first plurality of flow channels. Sample and/or one or more of the reactants are placed into the inlets to the first plurality of flow channels. The airtight chamber is then pressurized, thereby forcing the sample and/or one or more reactants into the flow channels.

Nucleic acid amplification reactions utilizing array-based devices generally involve introducing nucleic acid samples into each of the first plurality of flow channels and one or more reactants for conducting an amplification reaction into each of the second plurality of flow channels, whereby the nucleic acid samples and the one or more reactants become mixed. By heating regions of the microfluidic device to promote reaction, amplified product can be formed. Amplified product can be detected according to the methods set forth above. Sequencing and quantitative PCR reactions can be performed in related fashion.

Temperature is controlled at the temperature regions or reaction chambers of the microfluidic devices utilizing any of a number of temperature controller including, but not limited to, a Peltier device, a resitive heater, a heat exchanger and an indium tin oxide element. Certain temperature controllers suitable for use with the array-based microfluidic devices are provided. Some of these controllers include (a) a plate assembly comprising a first plate and a second plate that are separated from one another by a separation material, the separation material forming a fluid-tight seal around the periphery of the plates, the space between the plates and bounded by the separation material defining a chamber; (b) an inlet assembly located at a first end region of the plate assembly and in fluid communication with the chamber; and (c) an outlet assembly located at a second end region of the plate assembly opposite the first end region and in fluid communication with the chamber such that fluid in the chamber can exit therefrom via the outlet assembly. With controllers of this design a region located between the inlet and outlet assembly and adjacent or abutting a surface of the first plate is adapted to receive a microfluidic chip, the first and second plate comprise a transparent region that permits optical detection of the microfluidic chip, and the top plate is less than 100 microns thick. Other temperature controllers include a plate assembly that comprises (i) a hinged assembly that comprises a first plate and a second plate that are hingeably connected, such that the first plate can be moved toward or away from an upper face of the second plate; (ii) a third plate; (iii) a separation material that separates a lower face of the second plate opposite the upper face from the third plate and forms a fluid-tight seal therebetween; (iv) a chamber formed by the space between the lower face of the second plate and the third plate and being bounded by the separation material; and (v) a pair of holes, one hole being located in the first plate and the other hole being located in the second plate, the holes positioned such that when the first plate is folded onto the second plate, the pair of holes are aligned. In addition to the plate assembly, the temperature controller includes an inlet assembly located at a first end region of the plate assembly and in fluid communication with the chamber; and (c) an outlet assembly located at a second end region of the plate assembly opposite the first end region and in fluid communication with the chamber such that fluid in the chamber can exit therefrom via the outlet assembly, wherein the hinged assembly is adapted to receive a microfluidic chip between the first and second plate.

To facilitate amplification reactions, polymerase can be immobilized only within temperature regions at which primer extension occurs. This means that non-thermophilic polymerases can be utilized as the polymerase is not exposed to the higher temperatures required to separate the template nucleic acid from the extension product.

In certain devices, detection is facilitated by immobilizing one or more nucleic acids to a region of a flow channel or reaction chamber. Such nucleic acids can serve as probes to bind selected amplification products, for example. By spatially depositing the nucleic acids in known locations, the presence or absence of particular target nucleic acids can be ascertained according to the location at which a target nucleic acid binds to the array of nucleic acids.

DETAILED DESCRIPTION OF THE INVENTION

I. Definitions

Figure 1:
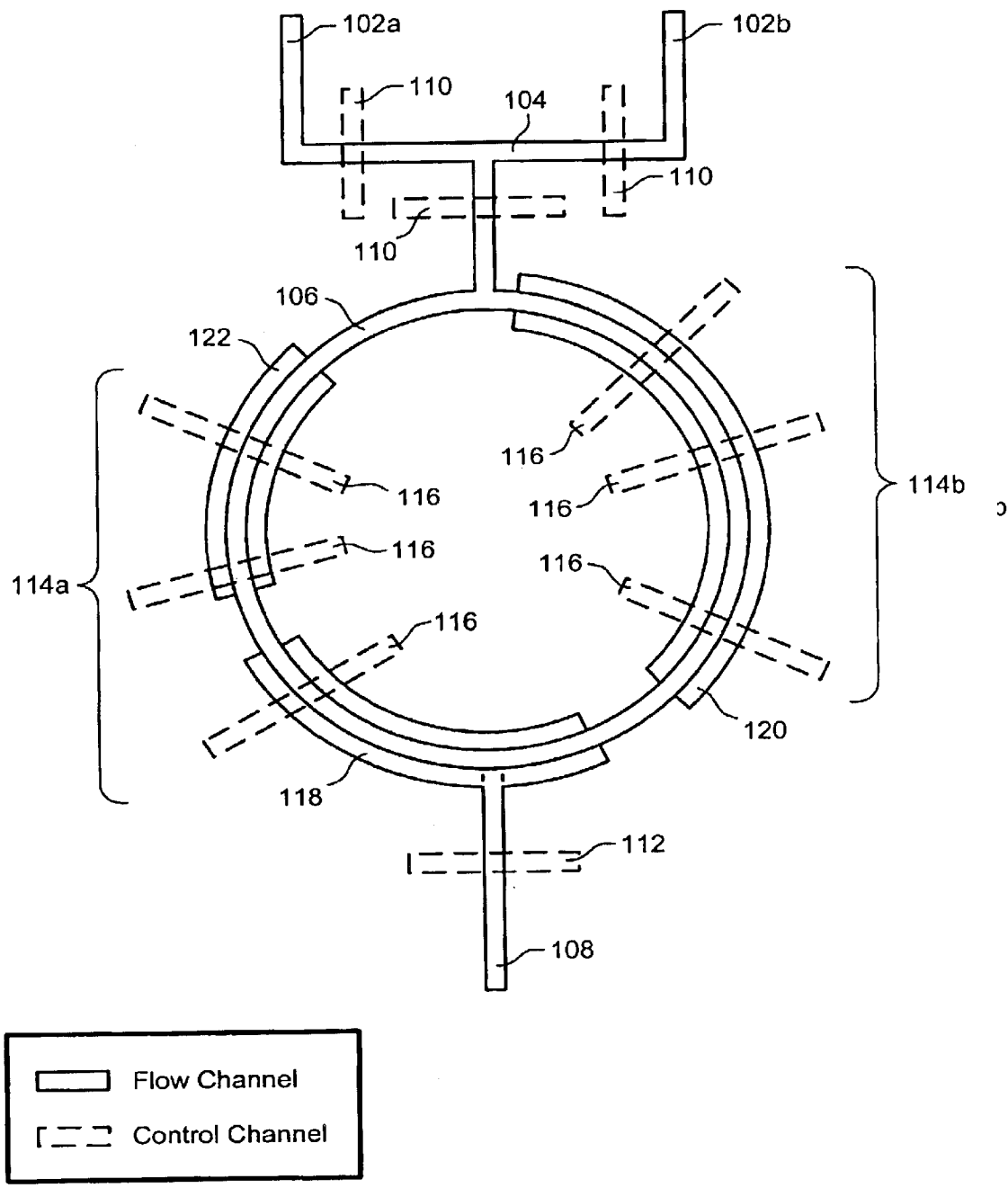
FIG. 1 is a schematic representation of an exemplary microfluidic device for conducting thermal cycling reactions that utilizes a substantially circular flow channel configuration.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

A "flow channel" refers generally to a flow path through which a solution can flow.

The term "valve" unless otherwise indicted refers to a configuration in which a flow channel and a control channel intersect and are separated by an elastomeric membrane that can be deflected into or retracted from the flow channel in response to an actuation force.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa–1 TPa, in other instances between about 10 Pa–100 GPa, in still other instances between about 20 Pa–1 GPa, in yet other instances between about 50 Pa–10 MPa, and in certain instances between about 100 Pa–1 MPa. Elastomeric materials having a Young's modulus outside of these ranges can also be utilized depending upon the needs of a particular application.

Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in U.S. application Ser. No. 09/605,520, and PCT Application No. 00/17740, both of which are incorporated herein by reference in their entirety.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14–25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, enzymes linked to nucleic acid probes and enzyme substrates. The term "detectably labeled" means that an agent has been conjugated with a label or that an agent has some inherent characteristic (e.g., size, shape or color) that allows it to be detected without having to be conjugated to a separate label.

II. Overview

A variety of microfluidic devices and methods for conducting analyses that benefit from temperature control are provided herein. Certain devices generally include a microfabricated flow channel along which a plurality of different temperature regions are located. In some of these devices, the flow channel forms a loop to allow for continuous and cyclic solution flow through the flow channel, thus allowing a sample to be repeatedly exposed to the different temperature regions.

Still other microfluidic devices provided herein comprise a plurality of intersecting flow channels to form an array or matrix of reaction chambers or junctions at which reactions can occur. Such devices permit a large number of reactions (e.g., nucleic acid amplification reactions) to be performed simultaneously in a multiplex format, or facilite high throughput screening of samples (e.g., screening compounds that bind to nucleic acids or proteins). Temperature controllers can regulate temperature for the entire device or a portion thereof (e.g., a junction at which flow channels intersect). Some of the devices having such an architecture include valves that have different actuation thresholds. By judicious placement of such valves along a flow channel, certain reagents or sample can be segregated within a flow channel and subsequently released for diffusive mixing with other reagents in the flow channel.

The devices are further characterized in part by including various components such as flow channels, control channels, valves and/or pumps, at least some of which are manufactured from elastomeric materials. This is in sharp contrast to conventional microfluidic devices that typically are based on silicon substrates (i.e., silicon chips). Additionally, with many of the devices disclosed herein, amplification reactions can benefit from aspects of both space and time domain amplification approaches, whereas heretofore amplification reactions were typically limited to utilizing only one approach or the other. Moreover, as alluded to above, certain of the devices and methods utilize a substantially circular flow channel through which samples and reactant solutions can be repeatedly transported. With conventional microfluidic devices that utilize electric fields to control solution flow, continuous circular flow is not possible.

The devices provided herein are useful in performing a variety of analyses requiring temperature control. This includes template extension reactions that involve thermal cycling. Such template extension reactions include both linear amplification reactions (extension reactions conducted with a single primer) and exponential amplifications (extension reactions conducted with both forward and reverse primers). Thus, the term amplification refers to both linear amplification reactions (e.g., certain sequencing reactions and single base pair extension reactions) as well as exponential amplification reactions (e.g., PCR).

Certain methods can be conducted in a multiplexing format in which multiple target nucleic acids are simultaneously amplified in a flow channel as the targets and amplification agents are cycled through the different temperature regions, or within a reaction chamber where temperature is cycled. Such reactions can be performed by utilizing primers specifically complementary to the different targets and then utilizing differential detection methods to detect different amplified products. Alternatively, multiple temperature cycling devices can be incorporated into a single device in which solution flow is controlled through common control channels.

III. General Device Structure

The microfluidic devices disclosed herein are typically constructed at least in part from elastomeric materials and constructed by single and multilayer soft lithography (MLSL) techniques and/or sacrificial-layer encapsulation methods (see, e.g., Unger et al. (2000) Science 288:113–116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, one can slow or entirely block solution flow through the flow channel. Using combinations of control and flow channels of this type, one can prepare a variety of different types of valves and pumps for regulating solution flow.

The devices and methods described herein utilize such valves and pumps to control solution flow through a series of reaction chambers at which temperature can be regulated, and/or a series of different temperature zones or regions that are disposed along one or more flow channels, thereby providing a way to tailor a temperature sequence or profile according to the particular temperature requirements of an analysis. As noted supra, such devices can be utilized in a variety of analyses that utilize thermocycling, particularly nucleic acid amplification processes such as PCR, for example.

More specifically, some of the microfluidic devices that are provided typically include a flow channel into which a sample can be introduced and transported. In certain designs, the flow channel forms a loop such that sample introduced into the loop can be cycled multiple times through the enclosed loop. Such a flow channel can be referred to as a rotary microfluidic flow channel or simply rotary flow channel. The loop can be substantially circular in certain devices but other shapes such as rectangular, triangular, hexagonal, octogonal, or any other suitable geometrical shape, can be utilized as well.

A plurality of temperature zones or regions are spaced along the flow channel. These temperature regions are regions of the loop in which a temperature controller regulates temperature. These regions can be controlled by a single temperature controller but, more typically, the temperature in each region is regulated by a separate temperature controller. The temperature regions can be of varying lengths as a way to further control the temperature of the solution flowing through the flow channel. With certain devices, the width and/or depth of the flow channel is varied in the different temperature zones to provide a further mechanism for regulating temperature.

As noted above, solution flow through the flow channel is controlled using one or more control channels that are separated from the flow channel by a semipermeable membrane. The deflection of such membranes into the flow channel can be used to block solution flow (i.e., as a valve), to expel solution from one region of the flow channel to another region (i.e., as a pump), and, by staggering the time at which a series of control channels are actuated so as to stagger membrane deflection into the flow channel, to produce a peristaltic pumping action. With the use of such arrangements, one can regulate solution flow through the flow channel without having to utilize electric fields to effectuate transport, although such techniques can also be utilized in certain applications.

Certain devices also include a detection section at which unreacted agents and/or products can be detected. This detection section can include detectors that are incorporated into the device or be aligned with a detector that is not incorporated into the device. In some instances, the detection section includes the flow channel in which the thermal cycling reaction takes place. In other designs, the detection section is located at another part of the device, typically downstream from an outlet connected to the flow channel in which thermal cycling occurs. Because the microfluidic devices provided herein can be made of elastomers that are substantially optically transparent, the devices can be used with certain detection systems that cannot be utilized with conventional devices manufactured from silicon.

Thus, in operation, certain methods involve introducing a sample into the flow channel and then actuating control channels associated with the flow channel to move the sample from one temperature region to another. With certain devices, solution can be transported semi-continuously or continuously around the looped flow channel such that the sample is repeatedly exposed to the different temperature zones in a cyclic fashion.

For applications involving nucleic acid template extension reactions such as nucleic acid amplification reactions, a sample containing a nucleic acid target is introduced into the flow channel. Components for conducting the amplification (e.g., primers, deoxynucleotides, polymerase, buffers and cofactors such as metal ions) are also introduced into the flow channel. The order in which these solutions are added can be reversed. The temperature within the temperature regions is selected to promote the major processes involved in amplification reactions, namely annealing of primer(s) to the target nucleic acid, extension of the primers, dissociation of complementary strands of the extension product, and then reannealing of primer to target nucleic acid or amplified product.

Other microfluidic devices include some of the foregoing features but differ in that rather than having a loop-shaped flow channel, the device includes a plurality of intersecting horizontal and vertical flow channels, the intersections providing reaction chambers at which reactions can occur. Temperature at the reaction chambers or junctions can be controlled by a temperature controller that regulates temperature throughout the device, or one or more temperature controllers that regulate temperature at one or more of the reaction chambers.

In operation, these array or matrix type devices involve flowing a set of reagents through the horizontal flow channels and one or more sets of reagents through the vertical flow channels. These reagents become mixed together within the junctions of the horizontal and vertical flow channels. Typically, products and/or unreacted regents are detected at the junctions of the flow channels or at regions of the flow channel adjacent the junctions.

The following sections describe in greater detail a number of specific configurations that can be utilized to achieve temperature control during analyses, particularly nucleic acid amplification reactions. It should be understood, however, that these configurations are exemplary and that modifications of these systems will be apparent to those skilled in the art.

IV. Devices Utilizing a Substantially Circular Flow Channel Configuration

A. Architecture

Devices of this configuration utilize a rotary pump design in which one or more elastomeric pump(s) act to circulate fluid through a substantially circular flow channel. As used herein the term "substantially circular" has the meaning known in the art and refers to configurations that are circles, as well as variations from a circular configuration such as ellipsoids, ovals and octagons for example.

Devices of this design can be manufactured by multilayer soft lithography. Such devices generally consists of two layers that are joined together: a first layer into which flow channels are formed and through which sample and reactants flow, and a second layer into which control channels are formed. These two layers are joined such that the control channels are appropriately oriented with respect to the flow channels. The resulting device is typically then affixed to a substrate (e.g., a glass slide) such that the substrate forms one wall of the flow channel. However, a thin elastomeric membrane can be placed over the exposed flow channel to form a device in which the flow channel is entirely formed of elastomer.

One exemplary microfluidic device for conducting thermal cycling reactions is illustrated in FIG. 1. This device 100 includes in the layer with the flow channels a plurality of sample inputs 102a and 102b, a mixing T-junction 104, a central circulation loop 106 (i.e., the substantially circular flow channel), and an output channel 108. As indicated supra, the intersection of a control channel with a flow channel can form a microvalve. This is so because the control and flow channels are separated by a thin elastomeric membrane that can be deflected into the flow channel or retracted therefrom. Deflection or retraction of the elastomeric membrane is achieved by generating a force that causes the deflection or retraction to occur. In certain systems, this is accomplished by increasing or decreasing pressure in the control channel as compared to the flow channel with which the control channel intersects. However, a wide variety of other approaches can be utilized to actuate the valves including various electrostatic, magnetic, electrolytic and electrokinetic approaches. Such approaches are described, for example, in PCT Publication WO 01/01025, previously incorporated herein in its entirety for all purposes.

The substantially circular central loop 106 and the control channels 116 that intersect with it form the central part of the rotary pump. The pump(s) 114a and 114b that cause solution to be flowed through the substantially circular flow channel 106 consist of a set of at least three control channels 116 that are adjacent to one another and which intersect the substantially circular branch flow channel 106 (i.e., the central loop). When a series of on/off actuation sequences, such a 001, 011, 010, 110, 100, 101, are applied to the control channels 116, the fluid in the central loop 106 can be peristaltically pumped in a chosen direction, either clockwise or counterclockwise. The peristaltic pumping action results from the sequential deflection of the membranes separating the control channels 116 and flow channel 106 into or out of the flow channel. In general, the higher the actuation frequency, the faster the fluid rotates through the central loop. However, a point of saturation is eventually reached at which increased frequency does not result in faster fluid flow. This is primarily due to limitations in the rate at which the membrane can return to an unactuated position. While the system shown in FIG. 1 shows two sets of pumps 114a and 114b (i.e., two sets of three control channels 116 that overlay the substantially circular flow channel 106) a single pump can be utilized (i.e., a single set of three control channels overlaying the substantially circular flow channel). Furthermore, while each pump is shown as including three control channels, more control channels can be utilized. It should also be understood that the three control channels can be different segments of a single control channel that overlay the flow channel.

Figure 18:
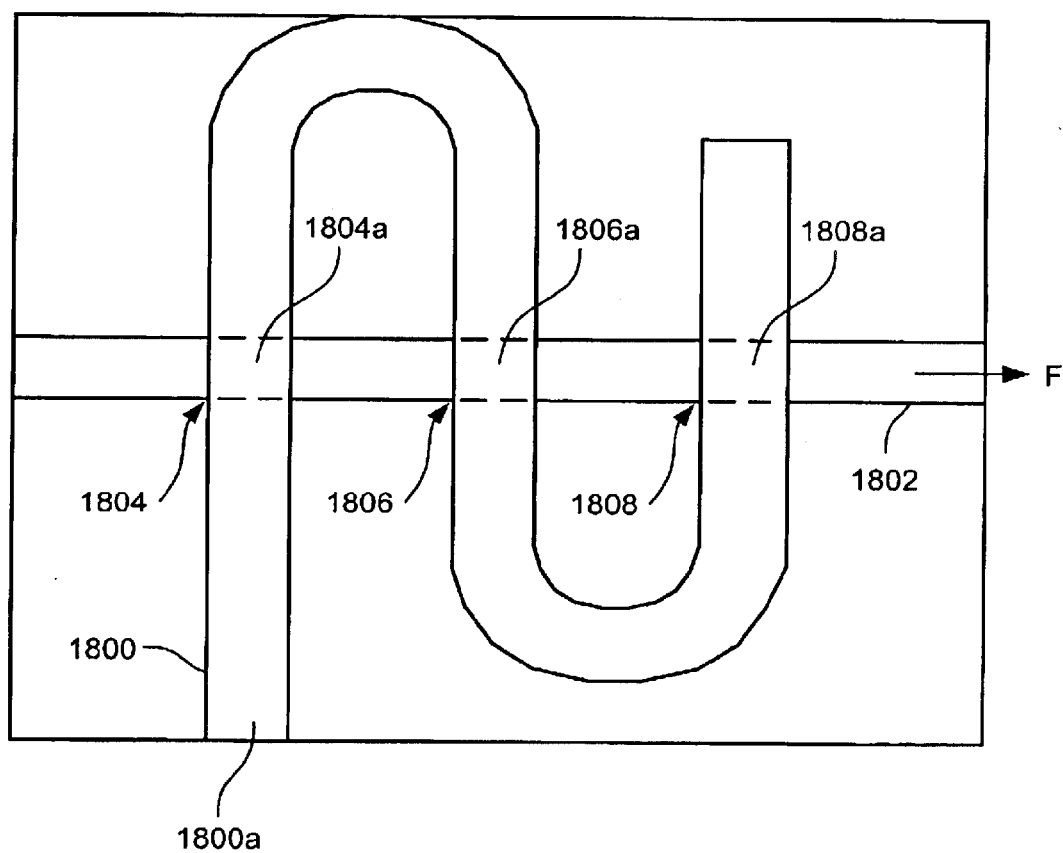
FIG. 18 shows an "S" shaped control channel design that can provide peristaltic pumping action on an underlying flow channel.

An example of such an arrangement is an "S" shaped control channel that passes over the flow channel at least three times. FIG. 18 presents a plan view of a pump structure, wherein serpentine control channel 1800 crosses over underlying flow channel 1802 at three different points, thereby creating three valve structures 1804, 1806, and 1808 having membranes 1804a, 1806a, and 1808a respectively. Application of a high pressure signal to first end 1800a of control channel 1800 causes a high pressure signal to propagate to first valve 1804, then to second valve 1806, and finally to third valve 1808, as shown in TABLE 1.

TABLE 1

| TIME | VALVE 7804 | VALVE 7806 | VALVE 7808 |
|---|---|---|---|
| $T_0$ | 1 | 0 | 0 |
| $T_1$ | 1 | 1 | 0 |
| $T_2$ | 1 | 1 | 1 |
| $T_3$ | 0 | 1 | 1 |
| $T_4$ | 0 | 0 | 1 |
| $T_5$ | 0 | 0 | 0 |

0 = valve open; 1 = valve closed

The resulting sequence of deflection of membranes 1804a, 1806a, and 1808a creates a pumping action in flow channel 1802 in direction F. Moreover, relaxation of pressure at first end 1800d of control channel 1800 at time $T_3$ would cause a low pressure signal to propagate to first valve 1804, then to second valve 1806, and finally to third valve 1808, setting the stage for another pumping sequence without causing reversal in direction of material previously flowed through channel 1802.

A variety of different auxiliary flow channels which are in fluid communication with the central loop 106 can be utilized to introduce and withdrawn sample and reactant solutions from the central loop. As depicted in FIG. 1, for example, a plurality of inlets 102a and 102b that are joined to a T-shaped flow channel 104 that is in fluid communication with the central loop 106 can be used to introduce sample and solutions containing reactants or assay components into the central loop 106. Similarly, one or more exit or outlet flow channels 108 in fluid communication with central loop 106 can be utilized to remove solution from central loop 106. Control valves 110 and 112 can be utilized at the inlet(s) and the outlet(s), respectively, to prevent solution flow into or out from the central loop 106.

With continued reference to FIG. 1, it can be seen that a plurality of temperature regions 118, 120 and 122 are located at different locations along the central loop 106. As shown, these temperature regions 118, 120 and 122 can be of varying lengths. In this way, one can flow solution through the central loop at a continuous flow rate but still vary the length of time that solution is exposed to a particular temperature. As described in greater detail infra, a variety of different types of temperature controllers can be utilized to regulate temperature within the different temperature regions. In certain designs, a heater (e.g., sputtered resistive metal) is positioned between the flow channel and the substrate (see FIG. 4). Usually the temperature is different in each of the different temperature regions. While the device shown in FIG. 1 shows three separate temperature regions, it should be understood that fewer or more temperature regions can be utilized. The number of regions depends primarily on the nature of the reaction and the size of the device. A related device described in the examples below describe a system with just two temperature regions.

Flow channel sizes and shapes can vary. With certain devices, the diameter of the channel tends to range from about 1 mm to 2 cm, although the diameter can be considerably larger in certain devices (e.g., 4, 6, 8, or 10 cm). Limits on how small the diameter of the circular flow channel can be are primarily a function of the limits imposed by the multilayer soft lithography processes. Channel widths (either flow or control) usually vary between 30 $\mu$m and 250 $\mu$m. However, channel width in some devices is as narrow as 1 $\mu$m. Channels of larger widths can also be utilized, but generally require some type of structural support within the flow channel. Channel height generally varies between 5 and 50 $\mu$m. The flow channel is typically rounded to allow for complete blockage of the channel once the membrane is deflected into the channel. In some devices, the channels have shapes such as octagons or hexagons. In certain devices, the flow channels are rounded and 100 $\mu$m wide and 10 $\mu$m high and control channels are 100 $\mu$m wide and 10 $\mu$m high. One system that has been utilized in certain studies has utilized a central loop having a diameter of 2 cm, a flow channel depth of 100 $\mu$m and a width of 10 $\mu$m. While the channels typically have the foregoing sizes and shapes, it should be recognized that the devices provided herein are not limited to these particular sizes and shapes.

Devices utilizing a substantially circular design allow considerable flexibility in exposing samples to desired temperature profiles because of the ability to control temperature in both the time and space domains. With the central loop and the integrated pumps, these devices also permit one to continuously and repeatedly to flow solution through the different temperature zones. However, by periodically altering the rate of control valve actuation, one can also regulate how long solution is exposed to any particular temperature.

B. Methods for Conducting Analyses

A wide variety of applications can be conducted with devices 100 having the design shown in FIG. 1, especially applications requiring temperature cycling. Before introducing solution into device 100, it is sometimes helpful to first purge the flow channels within the device of air. This avoids potential complications resulting from the formation of air bubbles within the flow channels that can disrupt solution flow through the flow channels. Because the devices described herein are wholly or largely manufactured from elastomeric compounds that have a certain degree of porosity, this can conveniently be achieved by pressurizing the device which causes any gas to diffuse through the pores of the device.

Once device 100 has been primed, sample and any necessary reagents are collectively or separately introduced into the central loop 106 via the inlets 102a and 102b. The control valves 110 positioned adjacent the inlets 102a and 102b and the T intersection 104 are initially opened to allow solution to flow into the central loop 106. After the desired samples and reagents have been introduced into the central loop 106, the control valves 110 at the inlets 102a and 102b and outlet 108 are closed. Solution is circulated through the central loop 106 by actuating the pumps 114a and 114b. As the solution is cycled around the central loop 106, the sample and reagents are exposed to a sequence of different temperatures.

Following completion of the temperature cycling, the presence of remaining reactants and/or products generated during reaction can be detected. With certain devices detection is accomplished by detecting remaining reactants and/or products within the central loop 106 itself. Thus, the rotary pump 106 constitutes a detection region. In other instances, the control valve 112 of the outlet 108 is opened so solution can be removed from the central loop 106. The solution that is withdrawn can then be transported via a flow channel in fluid communication with the outlet 108 to a detection region elsewhere on the microfluidic device. Alternatively, the solution can be removed from the microfluidic device and analyzed on a separate device.

As described in greater detail below, a wide variety of detection options can be utilized to detect the reactants and/or products. The particular method employed depends upon the nature of the reactant and/or product being detected.

In the specific instance of nucleic acid amplification reactions, a sample containing or potentially containing a target nucleic acid is introduced into the central loop 106 via one of the inlets 102a and 102b. The other reagents necessary to conduct the amplification reaction are similarly introduced via one of the inlets 102a and 102b. The sample and reagents can be introduced collectively or separately. Reagents typically utilized to conduct an amplification reaction will vary somewhat depending upon the particular type of amplification reaction being conducted and are known to those of ordinary skill in the art. Typical reagents include a primer or primers (e.g., forward and reverse primers) that specifically hybridize to the target nucleic acid, the four deoxynucleoside triphosphates (i.e., dATP, dTTP, dGTP and dCTP), a polymerase, a buffer and various other cofactors required by the polymerase (e.g., metal ion).

Following introduction of the sample and the necessary amplification reagents into the central loop 106, the sample and amplification reagents are circulated around the central loop 106 under the action of the pumps 114a and 114b. The number of temperature regions 118, 120 and 122 and the temperature therein can be selected according to the particular amplification reaction being conducted. The device shown in FIG. 1 is useful for conducting standard PCR reactions as it includes three temperature zones 118, 120 and 122 to promote the three primary events that occur during a PCR amplification, namely: (1) annealing of the primer(s) to its/their complementary target, (2) extension of the primer as the polymerase enzyme incorporates additional nucleotides, and (3) denaturation of the double stranded nucleic acid such that the primer(s) can reanneal to the target or a newly replicated strand. Temperatures typical for conducting PCR reactions are 95° C. (denaturation), 72° C. (extension) and 49–69° C. (annealing).

C. Variations

In some applications, the solution flow rate is varied. One approach for achieving this is to alter the rate at which the control channels are actuated. Alternatively, actuation of the control channels can be kept constant but the dimensions of the flow channel altered at different regions. Thus, the pumping rate can be kept constant while solution flow through the flow channel can be varied depending upon the size of the flow channel. Thus, in certain devices, the flow channel dimension can vary between one or more of the temperature regions as a way to provide another level of temperature control.

During the thermal cycling process, various reagents or solutions can optionally be introduced into the central loop via the inlets. For example, additional polymerase can be introduced if the enzyme starts to become denatured during the cycling process. More buffer solution can be introduced to compensate for solution loss due to evaporation. Similarly, solution can be withdrawn via the outlet during the cycling process as part of time course studies or to monitor the progress of the reaction, for example.

V. Devices Utilizing a Plurality of Reaction Chambers

A. Architecture

Figure 2:
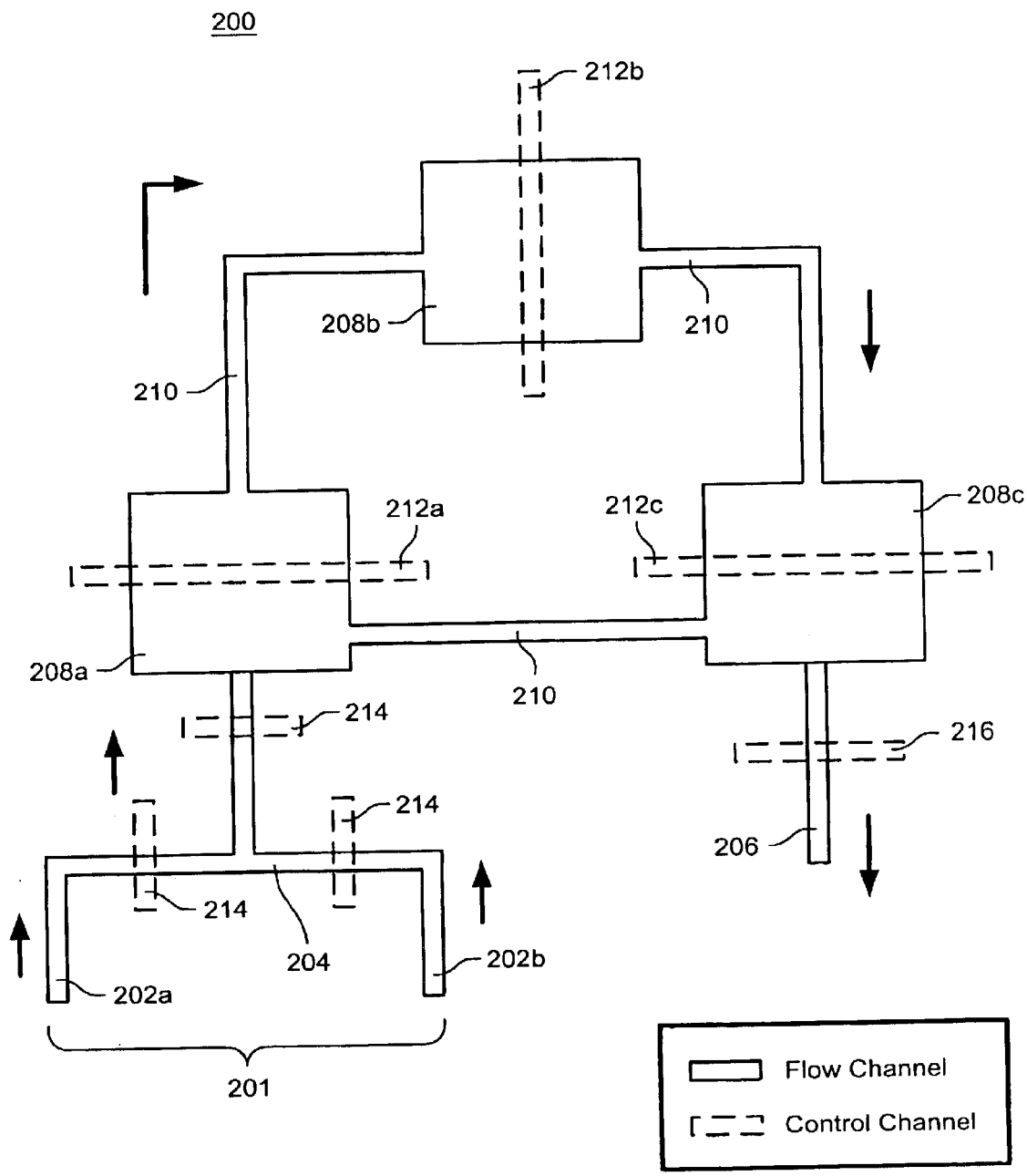
FIG. 2 is a schematic representation of another exemplary microfluidic device for conducting thermal cycling reactions in which the flow channel incorporates a plurality of reaction chambers.

An example of another configuration that can be utilized in thermocycling reactions is illustrated in FIG. 2. As with the microfluidic device illustrated in FIG. 1, this device 200 also is composed of two layers that are joined together: a first layer into which flow channels are formed and through which sample and reactants flow, and a second layer into which control channels are formed. After these two layers are joined such that the control channels properly intersect with the appropriate flow channels, the resulting device is typically affixed to a support (e.g., glass). Consistent with the architecture of the device shown in FIG. 1, the layer with the flow channels has a plurality of sample inputs 202a and 202b, a mixing T-junction 204, and an output channel 206 (see FIG. 2). This device, however, differs in that a plurality of reaction chambers 208a, 208b and 208c are disposed along the primary flow channel 210. In general, a different reaction chamber is provided for each different temperature region that is needed to conduct the analysis of interest.

Figure 3A:
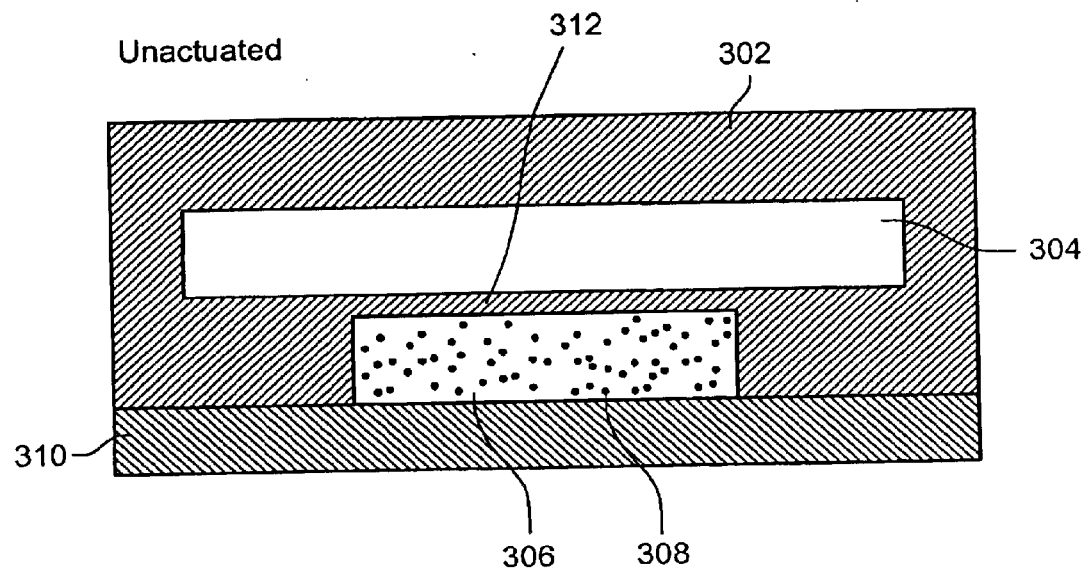
FIGS. 3A and 3B are cross-sectional views of an unactuated and actuated reaction chamber such as present in the microfluidic device illustrated in FIG. 2.
Figure 3B:
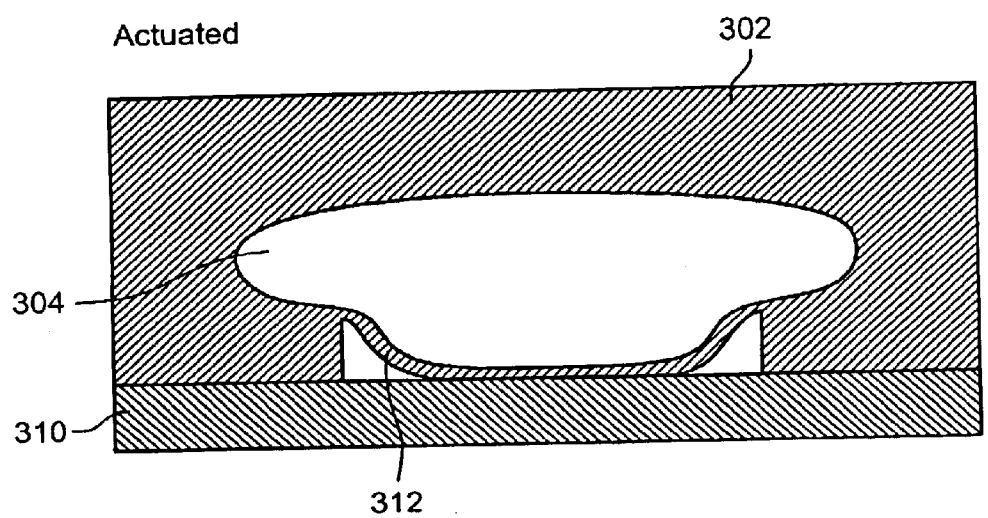

The plurality of reaction chambers 208a, 208b and 208c are in fluid communication with other reaction chambers in the system. The reaction chambers 208a, 208b, and 208c are also operatively disposed with respect to a control channel 212a, 212b and 212c, respectively. Actuation of the control channel associated with a reaction chamber causes the solution within the chamber to be expelled. As depicted in FIGS. 3A and 3B, because the control channel 304 and reaction chamber 308 are formed within an elastomeric material 302 (that is attached to a substrate 310) and separated by a flexible elastomeric membrane 312, actuation of the control channel 304 results in deflection of the membrane 312 into the reaction chamber 306. Because the membrane 312 can mold to the shape of the reaction chamber 306, essentially all solution and reactants 308 within the reaction chamber 306 is forced out of the actuated reaction chamber and into an unactuated reaction chamber. Reaction chambers 306 whose associated control channel 304 is actuated are sometimes referred to simply as actuated chambers; conversely, reaction chambers 306 whose control channels 304 are not actuated are referred to as unactuated reaction chambers. The reaction chambers in certain devices are fluidly connected such that actuation of all the control channels but one results in substantially all of the solution in the actuated reaction chambers being forced into the one reaction chamber whose control channel is not actuated (i.e., the sole unactuated reaction chamber).

The flow channel can include as few as two reaction chambers. However, the number of reaction chambers can vary significantly and is limited primarily by the size of the microfluidic device. As noted supra, in general the number of reaction chambers incorporated into the device is selected to correspond to the number of different temperature regions one requires for an analysis. With many nucleic acid amplification reactions three reaction chambers are utilized to accommodate the temperatures for performing annealing, extension and denaturation. However, certain devices include 4, 5, 6, 7, 8, 9 or 10 reaction chambers. Other designs utilize tens or even hundreds of reaction chambers, for example.

With systems of this design a sample and/or reagents can be rapidly passed back and forth between two or more reaction chambers by selective and alternate actuation of the corresponding control channels, thus resulting in the folding of a solution back onto itself. In this way, solutions can be rapidly mixed. Such configurations can also be utilized in a variety of thermal cycling applications by repeatedly passing a fluid through an established thermal gradient.

These devices allow reactions to be conducted with ultra small reaction volumes because one can consolidate the different reaction chambers into a small space and because solution is fully transferred between chambers due to the flexibility of the membrane that causes transport. The high compliance of the membrane can also accommodate for volume changes associated with the thermocycling process. High speed cycling can be achieved because there is no need to ramp the temperature to the desired level.

In the case of the particular device shown in FIG. 2, the device 200 includes an inlet system 201 having one or more inlets 202a and 202b and a mixing T junction 204 in fluid communication with the reaction chamber 208a set to the first temperature in the temperature gradient. Control valves 214 in the inlet system 201 can be used to control introduction of the sample and other reagents. Device 200 includes three reaction chambers 208a, 208b and 208c set to temperatures that are optimal for the annealing, extension and denaturation processes associated with the amplification reaction. Substantially all of the solution within device 200 can be transported to the reaction chamber having the next temperature in the gradient by actuating all of the other reaction chambers. An outlet flow channel 206 is in fluid communication with one reaction chamber 208c to allow reaction products and unreacted reagents to be withdrawn. Typically, the outlet 206 is in fluid communication with the reaction chamber 208c set to the final temperature in the temperature gradient.

B. Methods for Conducting Analyses

Sample and reagents are introduced into the first reaction chamber 208a in the flow channel 210 via the inlets 202a and 202b. Prior to introducing such solutions, the flow channel 210 and reaction chambers 208a, 208b and 208c can be purged of air as described supra to avoid potential problems associated with air bubble formation. Once introduced, typically the sample and reagents are transported from one reaction chamber/temperature region to another by actuating the control channels of all of the reaction chambers, except for the reaction chamber into which solution is to be delivered. Thus, referring once again to FIG. 2, once sample and reagents have had sufficient exposure to the temperature of reaction chamber 208a, substantially all of the solution in each of the reaction chambers and other sections of the flow channel system can be forced into reaction chamber 208b by actuating control channels 212a and 212c associated with reaction chambers 208a and 208c, respectively. Similarly, solution can be forced into reaction chamber 208c by actuating control channels 212a and 212b associated with reaction chambers 208a and 208b.

For nucleic acid amplifications, the general considerations set forth above with respect to the device shown in FIG. 1 apply to methods performed with device 200 as well. The temperature of each reaction chamber is set for the temperature that promotes the annealing, extension and denaturation processes. Solution is transported between the different reaction chambers by selectively actuating the appropriate control channels as just described. Any amplified product formed and unreacted reagents can be transported out of the reaction chambers via the outlet.

Detection of unreacted reagents and/or product can be conducted at one or more than one of the reaction chambers. Alternatively, detection can be conducted after reagents and product have been transported from the reaction chambers and at another location on the device. As with the other device, another option is to remove a portion of the withdrawn solution and to analyze the withdrawn solution on another system.

C. Variations

The same general variations described supra in relation to the system with a substantially circular system also apply here.

VI. Devices Utilizing an Array of Reaction Chambers

A. First Exemplary Configuration

1. Architecture

Certain devices comprise a plurality of intersecting vertical and horizontal flow channels which form an N×N array of cross-injection junctions or reaction chambers. A separate amplification reaction can be performed at each junction, thereby allowing a very large number of amplification reactions to be carried out on a single device at the same time. The number of vertical and horizontal flow channels can vary widely and is limited primarily by the overall size of the microfluidic device and the size and spacing of the flow channels. Devices of this type can include less than ten vertical and horizontal flow channels each, but often include tens or even hundreds of vertical and horizontal flow channels to form a vary large number of cross-injection junctions at which amplification reactions can take place.

Figure 5:
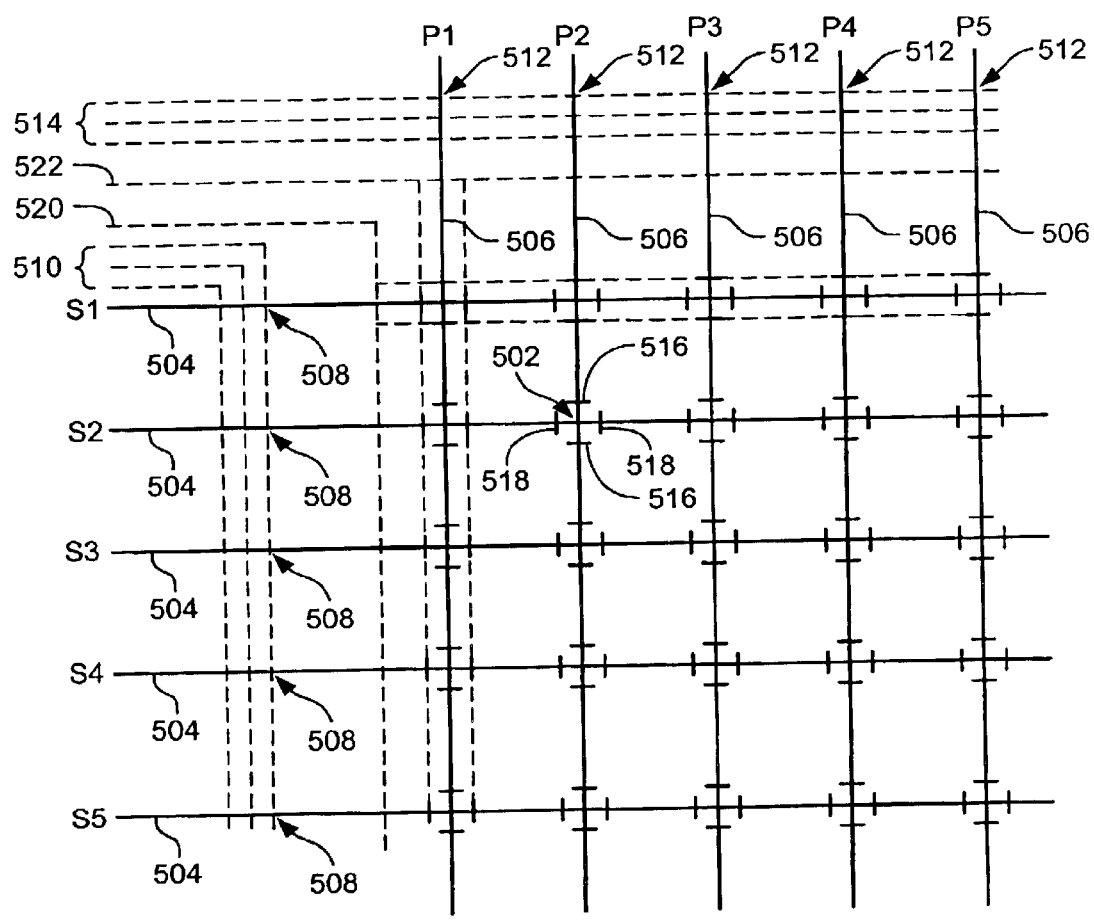
FIG. 5 is a plan view of a structure for high throughput screening of nucleic acids in accordance with one embodiment of the present invention.

FIG. 5 illustrates a specific example of such an alternative structure for performing nucleic acid amplifications. The high throughput structure of FIG. 5 comprises a five-by-five array 500 of cross-injection junctions 502 formed by the intersection of parallel horizontal flow channels 504 and parallel vertical flow channels 506. Array 500 enables the mixing of a nucleic acid sample S1–S5 with a primer-containing solution P1–P5, for a total of 5×5=25 simultaneous possible amplification reactions. The other components necessary for conducting a particular amplification reaction (e.g., polymerase, labeled and/or unlabeled nucleotides, metal ions and other cofactors) can be included in either the nucleic acid sample and/or with the primer solution.

Movement of nucleic acid sample solutions S1–S5 along horizontal flow channels 504 is controlled in parallel by peristaltic pumps 508 formed by overlying control channels 510. Movement of primer solutions P1–P5 along vertical flow channels 506 is controlled in parallel by peristatic pumps 512 formed by overlying control channels 514. Column valves 516 and row valves 518 surround each junction 502 formed by the intersection of horizontal and vertical flow lines 504 and 506.

Column valves 516 blocking flow in the vertical direction are controlled by a single control line 520. Row valves 510 blocking flow in the horizontal direction are controlled a single control line 522. For purposes of illustration, only the first portion of control lines 520 and 522 are shown in FIG. 5. However, it is to be understood that every row and column valve is controlled by these control lines.

During an amplification reaction, horizontal flow channels 504 introduce samples of five different nucleic acid samples (S1–S5) into junctions 502, while vertical flow channels 506 introduce five different primer-containing solutions (P1–P5) to junctions 502. Through the metering technique described below in connection with FIGS. 6A–6C, all 5×5=25 possible combinations of nucleic acid sample and primer are stored at the 5×5=25 junctions 502 of array 500. Each such amplification reaction is mixed at a fixed ratio of S to P.

Once charged with the nucleic acid samples and primer solutions, the microfluidic array is then cycled through temperatures chosen to promote the steps involved in the particular nucleic acid amplification (e.g., annealing of primer to nucleic acid target, primer extension and dissociation of strands in amplified product). In some instances, it is advantageous to separately control temperature between different columns (e.g., because different primers are introduced into different columns). To separately regulate the temperature, each column of the microfabricated device shown in FIG. 5 may include an associated temperature control structure. Although not shown in FIG. 5, such temperature control structures are described in detail below in section VIII and include thermistors, resistive heaters and Peltier controllers.

In other instances, separate control over the temperatures of columns of the array shown in FIG. 5 is not required. Such may be the case when the same primer is introduced to various samples in each column or when the primers and target nucleic acids have sufficiently similar composition that the amplification reaction steps can be performed at the same temperatures. Various temperature control devices can be utilized in this situation, including those described in section VIII. One option is simply to position the device adjacent a temperature control block which provides uniform heat over the array surface and which can be cycled through the different temperatures required for amplification.

If a very high degree of temperature control is required (e.g., for studies conducted to optimize reaction conditions), the devices can be manufactured such that the temperature at each junction can be separately regulated. Resistive heaters (see infra) positioned at each junction is one option for forming such devices, although other options described in section VIII can be utilized as well.

2. Methods for Conducting Analyses

Figure 6A:
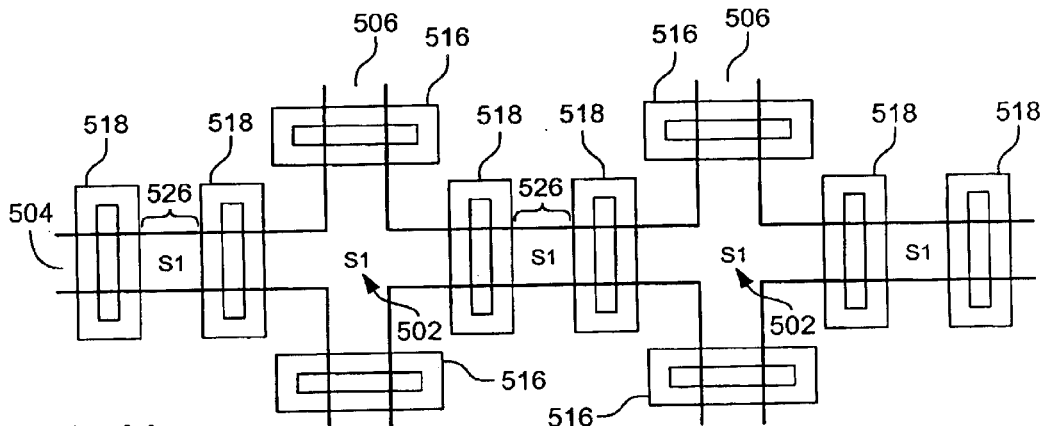
FIGS. 6A–6C are enlarged views of a portion of the structure of FIG. 5 showing its operation.
Figure 6B:
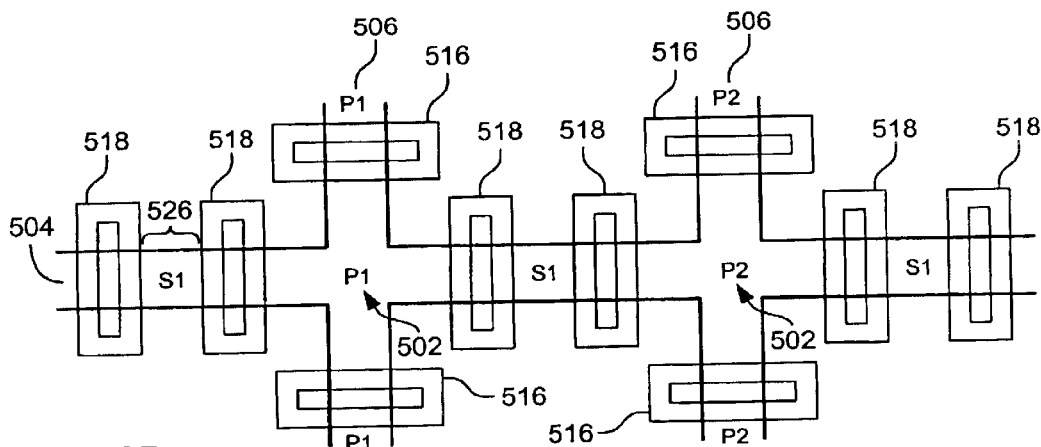
Figure 6C:
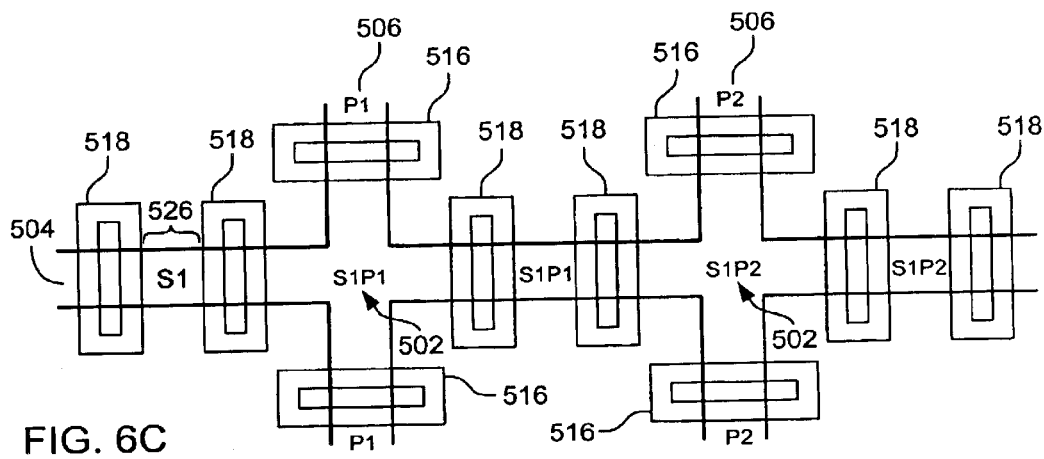

FIGS. 6A–6C show enlarged plan views of adjacent junctions of array 500 of FIG. 5. For purposes of illustration, the control lines are omitted in FIGS. 6A–6C. In addition, the lateral distance between junctions is considerably shortened, and in actuality the junctions would be separated by a substantial distance to prevent cross-contamination between junctions.

In a first step shown in FIG. 6A, column valves 516 are closed and nucleic acid samples are first flowed down each of horizontal flow channels 504. In the array portion shown enlarged in FIG. 6A, inter-row valve regions 526 are thereby charged with sample material S1.

Next, as shown in FIG. 6B, row valves 518 are closed, and column valves 516 are opened. Solutions containing different primers are flowed down each of vertical flow channels 506. In the array portion enlarged in FIG. 6B, junctions 502 are thereby charged with primers P1 and P2.

Finally, as shown in FIG. 6C, column valves 516 are closed and row valves 518 are opened. Pumping of the peripheral peristaltic pumps of the array causes the nucleic acid sample in inter-valve regions 526 to mingle with the primer solution of junctions 502 as both are flowed into junctions 502 and inter-valve regions 526. In the array portion enlarged in FIG. 6C, amplification may then occur in sample/primer environments S1P1 and S1P2 provided the primer and a nucleic acid within a given junction are complementary to one another.

With certain other devices, separate control lines can be used to control alternate row valves. In such an embodiment, the inter-row valve regions and the junctions are charged with sample and primer as described above in FIGS. 6A and 6B. Next, alternate row valves are opened such that sample in inter-row valve regions mixes by diffusion with primer in the junctions. This particular approach does not require pumping, and the closed state of the other set of alternate row valves prevents cross-contamination.

Once the various nucleic acid and primer solutions have been introduced into the array of junctions in the high throughput structure and mixed with one another (see FIG. 5), the device is cycled through the various temperatures which promote the different amplification stages. For those junctions in which the primer is complementary to a nucleic acid contained in the sample, amplified product is formed and can subsequently be detected. With knowledge of the identity of the primer at each junction, the presence or absence of particular target nucleic acids at each junction can be determined. Given the large number of junctions that can be formed as part of a microfluidic device, one can interrogate a very large number of samples in a short time period.

Amplified products can be detected according to any of the methods described below under section IX. As described in greater detail infra, one such approach utilizes molecular beacons (see, e.g., Tyagi et al., (1996) "Molecular Beacons: Probes that Fluoresce upon Hybridization", *Nature Biotechnology* 14:303–308, which is hereby incorporated by reference for all purposes). By utilizing a variety of different molecular beacons (optionally bearing different labels), one can readily detect the presence of specific nucleic acids that are complementary to the target nucleic acid of interest.

Typically, amplified product is detected within the junctions. In certain designs, each junction is associated with its own detector. With other designs, each junction is interrogated with a single detector. For example, a detector may include a translatable stage to properly position each junction with respect to the detection element or a scanner that illuminates each junction. Alternatively, array detectors can be utilized to detect signals from each of the junctions simultaneously. Further details regarding these and other options are provided in Section IX.

B. Second Exemplary Configuration

1. Architecture

Other devices are array-based devices and share a number of similarities with the architecture to the arrays just described and illustrated in FIGS. 5 and 6A–6C. In general these devices also comprise a plurality of intersecting vertical and horizontal flow channels which form an N×N array of cross-injection junctions or reaction chambers. A separate amplification reaction can be performed at each junction, thereby allowing a very large number of amplification reactions to be carried out on a single device at the same time. Certain of these devices include two types of valves, a "large valve" and a "small valve," that differ with respect to the magnitude of the actuation force required to activate the valve. Thus, these valves have different activation thresholds. Utilization of such valves provides another level of control in regulating solution flow through the array.

Some devices are also designed such that a plurality of the vertical and/or horizontal flow channels are fluidly connected to a shared input. This configuration is useful because it means that separate aliquots of sample or reagent need not be separately added to each of the flow channels. The ability to fill a plurality of flow channels with a single sample significantly reduces total sample or reactant volume by eliminating much of the dead volume associated with separate injections into each flow channel. This feature is particularly important when the amount of sample or reagent available is limited or the cost of the sample and/or reagent is high.

Figure 12:
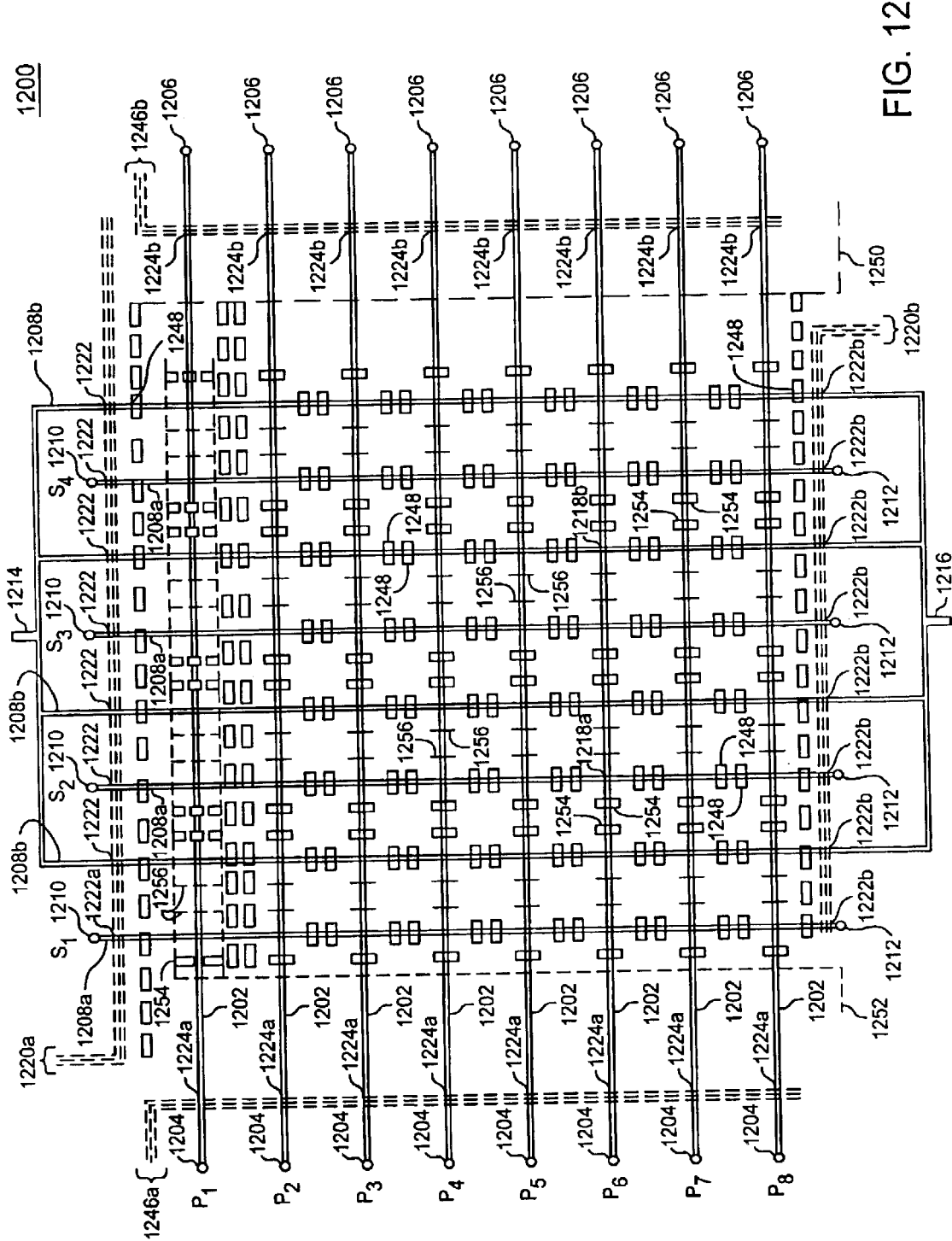
FIG. 12 is a plan view of an exemplary matrix or array microfluidic device that can be utilized to conduct nucleic acid amplification reactions and other types of reactions.

FIG. 12 illustrates a specific example of such an alternative structure for performing nucleic acid amplifications, including several of the foregoing design elements. The fluid layer (i.e., the layer containing the fluid channels) of the particular array-based device shown in of FIG. 12 comprises an 8×8 array 1200 of cross-injection junctions formed by the intersection of parallel horizontal flow channels and parallel vertical flow channels. The horizontal flow channels 1202 each have independent inlets 1204 and outlets 1206. The vertical flow channels, in contrast, are divided into a first set of M vertical flow channels 1208a that are connected to independent inlets 1210 and outlets 1212, and a second set of M vertical flow channels 1208b that are connected to a single or shared inlet 1214 and outlet 1216. The junctions, then, fall into two groups, those junctions 1218a formed by the intersection between a horizontal flow channel 1202 and a vertical flow channel 1208a not connected to shared inlet 1214, and those junctions 1218b that are formed by the intersection between a horizontal flow channel 1202 and a vertical flow channel 1208b that is connected to the shared inlet 1214.

This design enables N sets of a first reagent to be mixed with M sets of a second reagent and M sets of a third reagent (where M+M=N). Thus, for instance, with array 1200, four nucleic acid samples (e.g., S1–S4) can be mixed with eight primers, P1–P8, thus generating a total of 4×8=32 simultaneous reactions on a single chip. This particular architecture is useful because a reagent that is required for each reaction can be introduced as a single aliquot via shared inlet 1214 into the M vertical flow channels 1208b that are connected to shared inlet 1214. This feature reduces the complexity in loading the array 1200 and minimizes the amount of solution required for injection. Other components necessary for conducting a particular amplification reaction (e.g., labeled and/or unlabeled nucleotides, metal ions and other cofactors) can be included in either the nucleic acid sample and/or with the primer solution.

In the case of nucleic acid amplification reactions, for example, nucleic acid samples S1–S4 and common reagent, R (e.g., polymerase), are transported along vertical flow channels 1208a and 1208b under the action of peristaltic pumps 1222a and 1222b formed by overlying control channels 1220a and 1220b, respectively. Movement of primer solutions P1–P5 along horizontal flow channels 1202 is controlled by peristaltic pumps 1224a and 1224b formed by overlying control channels 1246a and 1246b, respectively. Because peristaltic pumps 1222a, 1222b, 1224a and 1224b are positioned on each side of array 1220, solution can readily be flowed back and forth through the vertical flow channels 1208a and 1208b and the horizontal flow channels 1202.

The control layer that overlays the fluid layer contains two types of control channels to define two different types of valves. Each set of control channels can have a single inlet for actuating the control channel. The use of the two different types of valves enables horizontal flow channels 1202 and vertical flow channels 1208a and 1208b to be actuated separately. The two valves differ with respect to the width of the control channel. Valves with wider control channels (e.g., approximately 200 microns) are referred to as big valves, whereas valves with narrower control channels (e.g., approximately 75 microns) are referred to as small valves. The wider the flow channel is, the easier it is to close the flow channel. Thus, at high actuation levels (e.g., high pressure levels), both big and small valves close and prevent solution flow through the flow channel upon which they act. However, at intermediate actuation levels (e.g., intermediate pressure levels), big valves remain closed and block solution flow, whereas small valves are deactuated and allow solution to flow through the flow channel. At low actuation levels (e.g., low pressure levels), both big valves and small valves are deactuated and allow solution to flow.

With continued reference to FIG. 12, large column valves 1248 that block solution flow in the vertical flow channels 1208a and 1208b are controlled by a single control line 1250. In contrast, another control line 1252, can regulate solution flow through the horizontal flow channels 1202 by actuating both large row valves 1254 and small row valves 1256. For purposes of illustration, only the first portion of control lines 1250 and 1252 are shown in FIG. 12. However, it is to be understood that every row valve 1254 and 1256 and column valve 1248 is controlled by control lines 1250 and 1252. As described in greater detail infra, the ability to selectively actuate the large valves and small valves means that solution can be flowed through a flow channel and then trapped between a pair of small valves. These small valves can then be selectively opened while the large valves remain closed to allow diffusive mixing between the trapped solution and solution within a junction, for example.

Thus, during an amplification reaction for instance, row valves 1254 and 1256 can be opened while column valves 1248 are closed to introduce eight different primer solutions (P1–P8) into horizontal flow channels 1202 and then into junctions 1218a and 1218b. Next, row valves 1254 and 1256 are closed and column valves 1248 opened to allow samples containing nucleic acids to flow through the vertical flow channels 1208a (i.e., those that are connected to individual inlets 1210) into junctions 1218a. With the valves in this same configuration, polymerase is introduced into those vertical flow channels 1208b that are connected to the shared inlet 1214. Through the metering techniques described below in connection with FIGS. 13A-D and 14A-C, all 8×4=32 possible combinations of nucleic acid sample and primer are stored at the junctions 1208a of array 1200.

2. Methods for Conducting Analyses

FIGS. 13A–13D show enlarged plan views of adjacent junctions of array 1200 of FIG. 12. To increase clarity, the control lines are omitted in FIGS. 13A–13D. Initially, column valves 1248 are closed and primer solutions are first flowed down each of horizontal flow channels 1202. In the array portion shown enlarged in FIG. 13A, junctions 1218a and 1218*b*, and inter-row valve regions 1260*a* defined by two large valves 1254 and inter-row valve regions 1260*b* defined by two small valves 1256 are thereby charged with primer, P1.

Figure 13A:
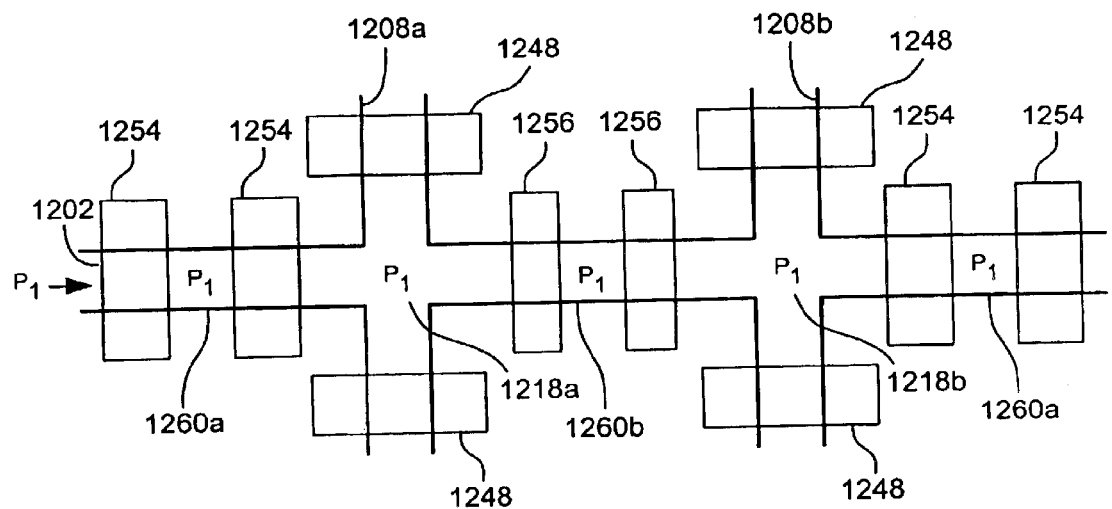
FIGS. 13A–13D are enlarged views of a portion of the device of FIG. 12 showing its operation.
Figure 13B:
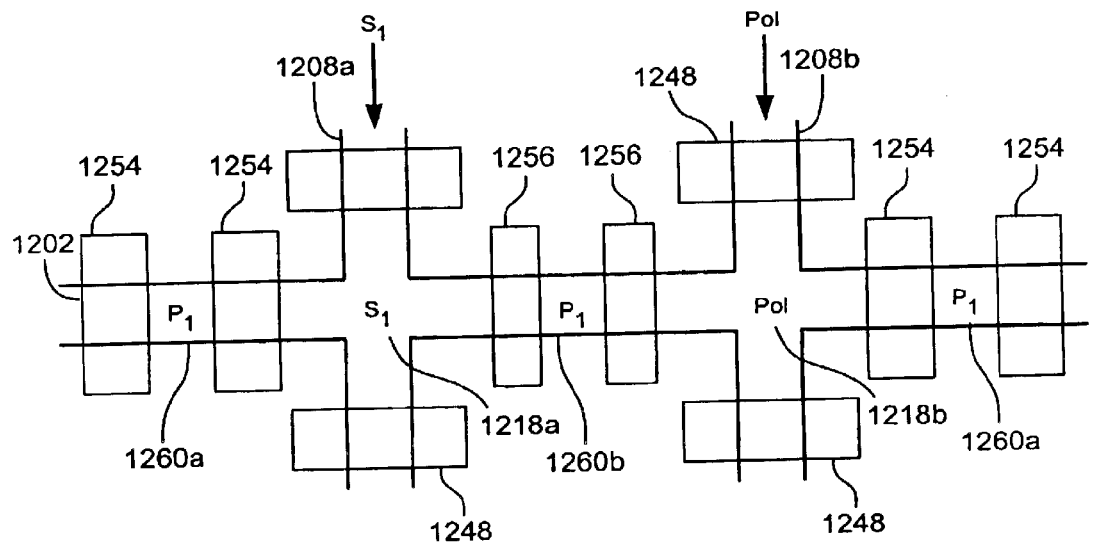

Next, as shown in FIG. 13B, both large row valves 1254 and small row valves 1256 are closed, while column valves 1248 are opened. Nucleic acid samples are then transported down vertical flow channels 1208*a* not connected to shared inlet 1214. In the array portion enlarged in FIG. 13B, junctions 1218*a* are thereby charged with sample S1. Similarly, polymerase, Pol, is flowed down vertical flow channels 1208*b* that are connected to shared inlet 1214; the junctions 1218*b* shown in array portion enlarged in FIG. 13B thus become charged with polymerase. Consequently, vertical flow channels alternate between those that contain sample and those that contain polymerase.

Figure 13C:
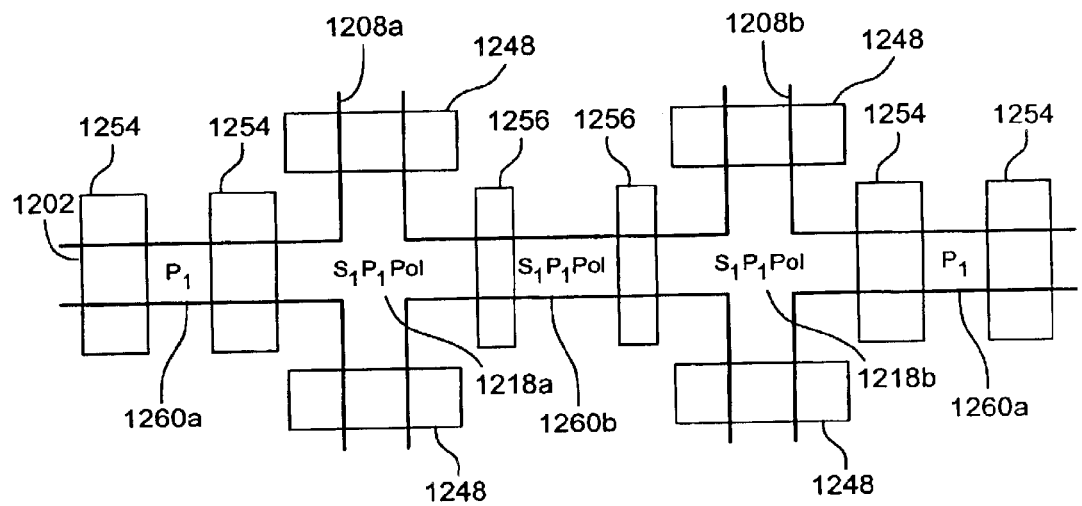
Figure 13D:
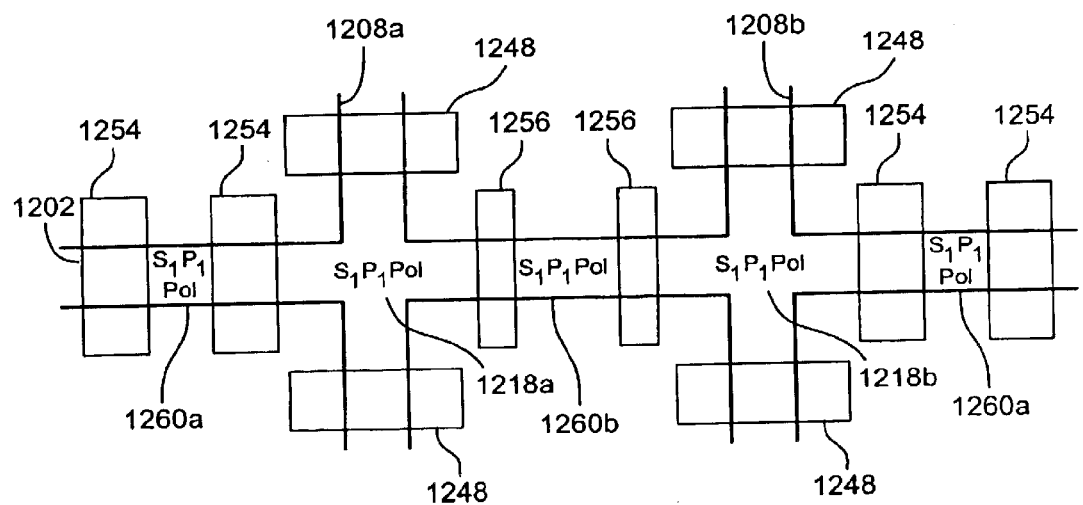

Finally, as shown in FIG. 13C, column valves 1248 are closed and small row valves 1256 are opened, while large row valves 1254 are kept closed. As indicated above, this can be achieved by applying an intermediate pressure to the control channels associated with large and small valves 1254 and 1256. In this approach, no pumping along the horizontal flow channel 1202 is required, as primer P1, sample S1 and polymerase Pol mix by diffusion to form the mixture P1, S1, Pol. Alternatively, as shown in FIG. 13D, column valves 1248 can be closed and both large row valves 1254 and small row valves 1256 opened. Pumping of the peripheral peristaltic pumps of the array causes the primer, P1, in inter-valve regions 1260*a* to mix with the nucleic acid sample, S1, of junction 1218*a* and polymerase Pol within junction 1218*b*, either as they are pumped in one direction or as they are pumped back and forth.

Figure 14A:
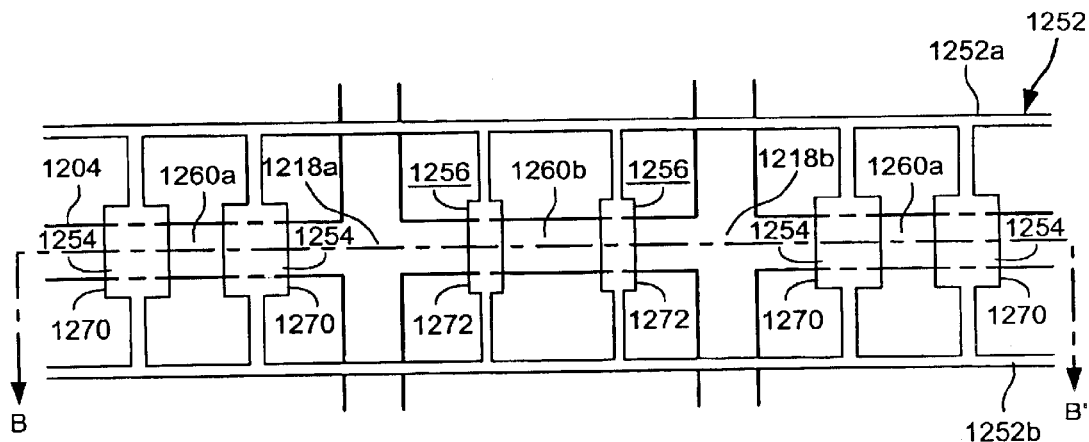
FIGS. 14A–14C are enlarged views of a portion of the device of FIG. 12 showing its operation.
Figure 14B:
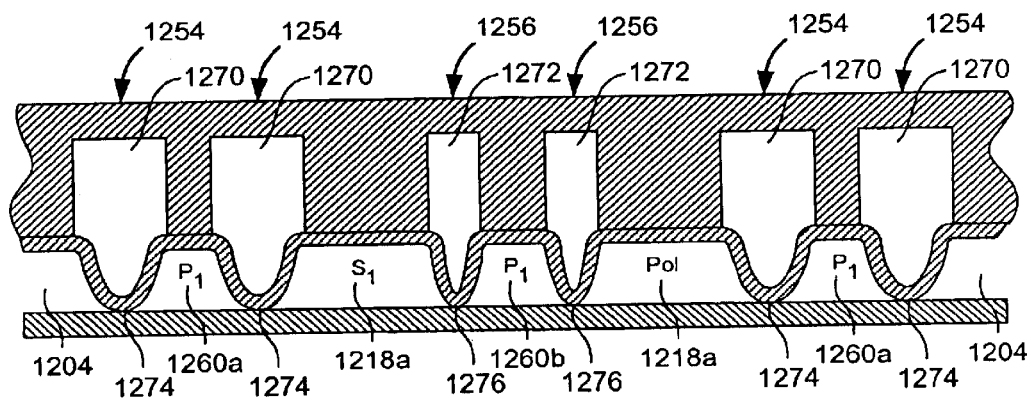
Figure 14C:
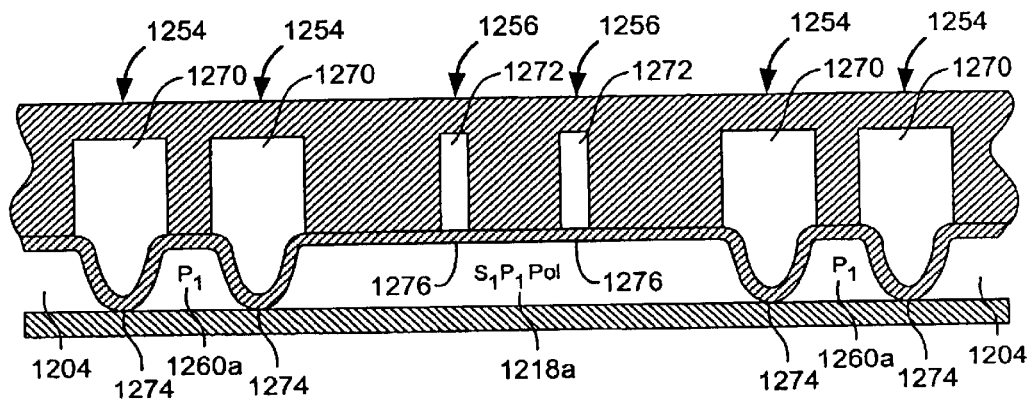

The foregoing process is illustrated in greater detail in FIGS. 14A–14C. FIG. 14A shows an enlarged view of a portion of one flow channel 1204. FIG. 14B presents a cross-sectional view along line B–B' of the enlarged flow channel portion of FIG. 14A prior to deactuation of small row valves to allow diffusion of sample, primer and polymerase located in inter-valve regions and adjacent junctions. FIG. 14C shows a cross-sectional view along line B–B' of the enlarged flow channel portion of FIG. 14A after deactuation of the small row valves.

Control line 1252 comprises parallel branches 1252*a* and 1252*b* positioned on either side of flow channel 1204. Branches 1252*a* and 1252*b* are connected by pairs of wide cross-over portions 1270 and narrow cross over portions 1272, which define large valves 1254 and small valves 1256, respectively. As set forth in FIGS. 13A–13D, junctions 1218*a* and 1218*b* are charged with a nucleic acid and polymerase, respectively; intervalve region 1260*a* and 1260*b* are initially filled with primer, P1.

As discussed briefly above, the differing width of crossover portions 1270 and 1272 cause elastomer membranes 1274 and 1276 of large valves 1254 and small valves 1256, respectively, to have different actuation thresholds. In particular, because wide membranes 1274 have increased area, they are easier to actuate then narrow membranes 1276. Thus, application of a high pressure to control line 1252 causes the deflection of both elastomer membranes 1274 and 1276 into the underlying flow channel 1204, closing both large valves 1254 and small valves 1256. Application of a low pressure to control line 1252, however, causes both elastomer membranes 1274 and 1276 to retract out from the underlying flow channel 1204, thus opening both large valves 1254 and small valves 1256. Finally, application of an intermediate pressure to control line 1252 causes only the wide membrane 1274 of large valve structures 1254 to remain actuated, whereas narrow membranes 1276 of small valve structures 1256 are deactuated to open the valve.

The differential response of the different sized valves enables a plurality of reaction subchambers to be defined with a single control channel. These subchambers can then be opened, permitting diffusion of the various reagents to mix together. This is illustrated in FIG. 14C, wherein an intermediate pressure is applied to control line 1252, allowing narrower membranes 1276 of small valve structures 1256 to retract out of flow channel 1204, while wide membranes 1274 of large valve structures 1254 remain within flow channel 1204 to prevent cross contamination between reaction sites.

Once the various nucleic acid and primer solutions have been introduced into the array of junctions in the high throughput structure and mixed with one another (see FIG. 5), the device is cycled through the various temperatures which promote the different amplification stages. For those junctions in which the primer is complementary to a nucleic acid contained in the sample, amplified product is formed and can subsequently be detected. Any of the variety of detection methods disclosed in section IX can be utilized to detect amplified product.

As with the other array-based system described supra, amplified product is usually detected within the junctions. In certain designs, each junction is associated with its own detector. With other designs, each junction is interrogated with a single detector (e.g., via the use of a translatable stage or an array detector).

Thus, the foregoing matrix arrays provides a way to conduct a large number of analyses with limited sample volume. Instead of having to micropipette an aliquot of sample (typically about 1 microliter) onto a microfluidic device for each analysis, the array- or matrix-based devices provided herein enable a large number of reactions to be conducted with a single aliquot of sample, as the sample (e.g., nucleic acid sample) comes into contact with numerous different reactants (e.g., different primers) in the various junctions which it enters. Thus, for instance, a one microliter sample can provide 500 assays (assuming 2 nanoliters per assay) using an array-based device such as set forth herein.

Further discussion of matrix arrays such as those disclosed herein that can be utilized in similar types of analyses, as well as additional discussion on the structure of such devices is set forth in a commonly owned and copending application entitled "High Throughput Screening of Crystallization of Materials," filed Apr. 5, 2002, and having attorney docket number 20174C-0049200US.

VII. Fabrication of Microfluidic Devices

The microfluidic devices disclosed herein are typically constructed by single and multilayer soft lithography (MLSL) techniques and/or sacrificial-layer encapsulation methods. The MLSL approach involves casting a series of elastomeric layers on a micro-machined mold, removing the layers from the mold and then fusing the layers together. In the sacrificial-layer encapsulation approach, patterns of photoresist are deposited wherever a channel is desired. The use of these techniques to fabricate elements of microfluidic devices is described, for example, by Unger et al. (2000) Science 288:113–116, by Chou, et al. (2000) "Integrated Elastomer Fluidic Lab-on-a-chip-Surface Patterning and DNA Diagnostics, in Proceedings of the Solid State Actuator and Sensor Workshop, Hilton Head, S.C.; and in PCT Publication WO 01/01025, all of which are incorporated herein by reference in their entirety for all purposes.

More specifically, certain fabrication methods involve initially fabricating mother molds for top layers (elastomeric layer with the control channels) and bottom layers (elastomeric layer with the flow channel) on silicon wafers by photolithography with photoresist (Shipley SJR 5740). Channel heights can be controlled precisely by the spin coating rate. Photoresist channels are formed by exposing the photoresist to UV light followed by development. Heat reflow process and protection treatment is performed as described previously (M. A. Unger, H.-P. Chou, T. Throsen, A. Scherer and S. R. Quake, Science 288, 113 (2000)). Thereafter, a mixed two-part-silicone elastomer (GE RTV 615) is spun into the bottom mold and poured onto the top mold, respectively. Again, spin coating can be utilized to control the thickness of bottom polymeric fluid layer. After baking in the oven at 80° C. for 25 minutes, the partially cured top layer is peeled off from its mold, aligned and assembled with the bottom layer. A 1.5-hour final bake at 80° C. is used to bind these two layers irreversibly. Once peeled off from the bottom silicon mother mold, this RTV device is typically treated with HCL (0.1N, 30 min at 80° C.) to cleave some of the Si—O—Si bonds to expose hydroxy groups that make the channels more hydrophilic. The device can the be sealed hermetically to a support. The support can be manufactured of essentially any material. The surface should be flat to ensure a good seal as the seal formed is primarily due to adhesive forces. Examples of suitable supports include glass, plastics and the like. The device can even be directly attached to certain detectors such as CCD elements and CMOS detection elements.

The devices formed according to the foregoing method results in the substrate (e.g., glass slide) forming one wall of the flow channel. Such an arrangement can be useful as certain temperature control elements can easily be formed onto the substrate. For example, as described in greater detail infra in the section on temperature control elements, certain thermistor heaters can be formed by sputtering a resistive metal such as tungsten onto the substrate utilizing established techniques. However, in some instances the device once removed from the mother mold is sealed to a thin elastomeric membrane such that the flow channel is totally enclosed in elastomeric material. The resulting elastomeric device can then optionally be joined to a substrate support. Devices having this latter structure can be useful for analyses are expected to generate high backpressures. Such pressures can sometimes cause the seal between the elastomeric device and the substrate to fail.

It has also been found that the seal between the elastomeric structure and the substrate can be improved by cleaning the elastomeric structure with ethanol prior to placing the structure on the substrate.

Further details regarding the preparation of a rotary pump such as utilized in some of the devices provided herein is set forth in Example 1 infra.

VIII. Temperature Control

A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in an array or matrix microfluidic device). With the devices and methods described herein, typically the temperature controllers are used to maintain a particular temperature within each of the temperature regions. Although in certain applications it may be advantageous to adjust the temperature within one or more of the temperature regions.

A. Resistive Heaters

Figure 4:
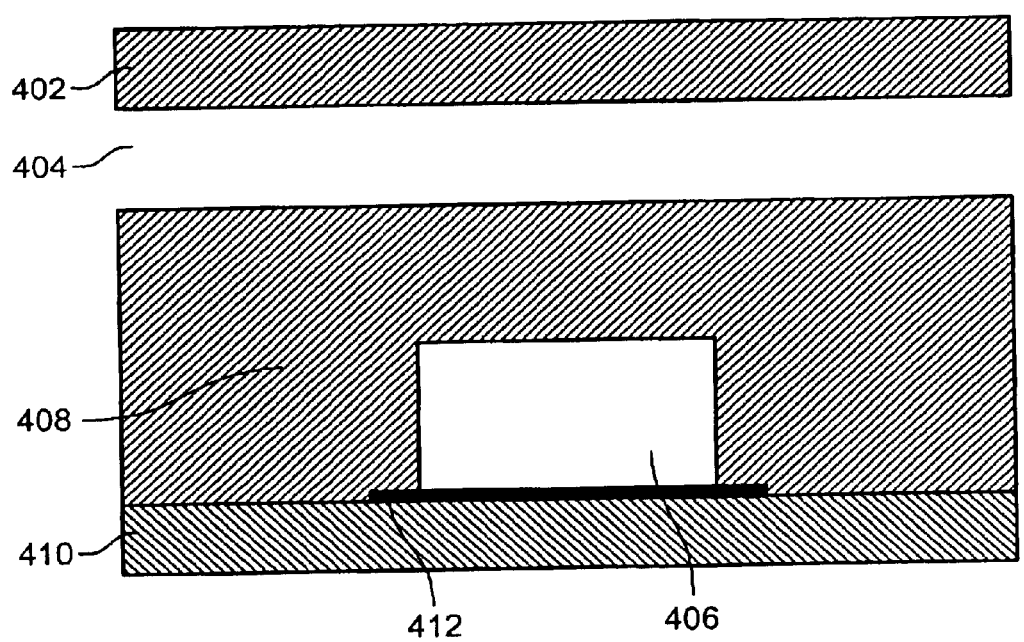
FIG. 4 is a cross-sectional view showing the location of a heater relative to the flow channel in a temperature region of a microfluidic device.

A resistive heater is an example of one heating element that can be utilized. Such heating elements can be adjusted to maintain a particular temperature. FIG. 4 illustrates the use of such a resistive heater. FIG. 4 is a cross-sectional view of a region of a microfluidic device formed of a control layer 402 into which a control channel 404 is formed. This control channel 404 overlays a flow channel 406 formed in fluid layer 408 which itself is attached to a substrate 410. One method for producing a heating element 412 of this type is to sputter a metal (e.g., tungsten) on the support 410 (e.g., glass slide) to which the fluid layer elastomeric structure 408 is applied. The sputtered material (i.e., heating element 412) is typically applied as a very thin layer (e.g., 500 to 1000 Angstroms thick) on support 410. To facilitate alignment of a section of the flow channel 406 with the heating element 412, the heating element 412 is often made wider than the flow channel 406. Because the heating element 412 is so thin, the elastomeric structure 408 having the flow channel 406 molded therein can form a tight seal against the heating element 412.

Typically, different resistive heaters are placed at each of the different temperature regions and regulated by their own power supply. However, the elastomeric devices can also be placed on a single heater that is regulated by a single power supply. The temperature at any given temperature region can then be controlled by the thickness of the metal sputtered adjacent each temperature region.

B. Peltier Heaters

Another suitable temperature controller is a Peltier controller (e.g., INB Products thermoelectric module model INB-2-(11-4)-1.5). This controller is a two-stage device capable of heating to 94° C. Such a controller can be utilized to achieve effective thermal cycling or to maintain isothermal incubations at any particular temperature.

C. Heat Exchangers

In some devices and applications, heat exchangers can also be utilized in conjunction with one of the temperature control sources to regulate temperature. Such heat exchangers typically are made from various thermally conductive materials (e.g., various metals and ceramic materials) and are designed to present a relatively large external surface area to the adjacent region. Often this is accomplished by incorporating fins, spines, ribs and other related structures into the heat exchanger. Other suitable structures include coils and sintered structures. In certain devices, heat exchangers such as these are positioned adjacent to the flow channel within one of the temperature regions or placed within the flow channel or reaction chamber. Heat exchangers that can be utilized with certain devices are discussed, for example, in U.S. Pat. No. 6,171,850.

Figure 17:
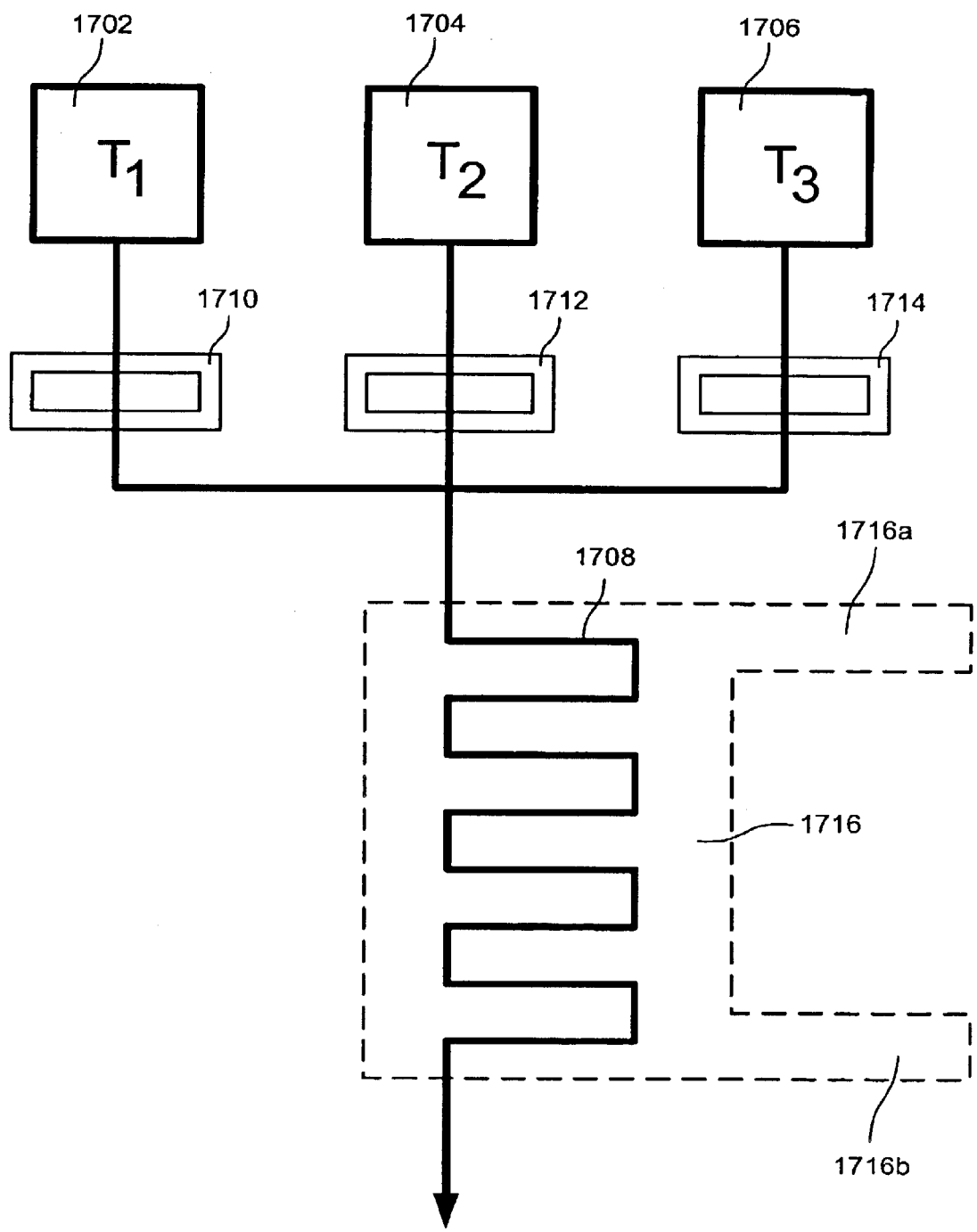
FIG. 17 illustrate another exemplary temperature controller that can be utilized to regulate temperature within a microfluidic device such as those disclosed herein.

FIG. 17 shows a plan view one embodiment of a heat exchanger for use in conjunction with a microfabricated structure in accordance with the present invention. Heat exchanger 1700 includes chambers 1702, 1704, and 1706 containing a flowable liquid. Liquid in each of chambers 1702, 1704, and 1706 is continuously maintained at different temperatures T1, T2, and T3. Serpentine flow channel 1708 is in fluid communication with chambers 1702, 1704, and 1706 through valves 1710, 1712, and 1714 respectively.

Serpentine flow channel 1708 is positioned proximate to microfabricated reaction chamber 1716 having inlet 1716a and outlet 1716b, respectively. In the structure shown in FIG. 17, serpentine flow channel overlies chamber 1716 and is separated from chamber 1716 by a membrane of elastomer material Depending upon actuation of valves 1710, 1712, and 1714, the temperature of liquid flowed through serpentine flow channel 1708 can be rapidly changed, with the corresponding exchange of thermal energy occurring across the thin elastomer membrane over the large surface area defined by serpentine channel 1708.

D. ITO Heaters

Other heating elements are formed from indium tin oxide, which is a transparent conductor. This material is available from a number of sources including Delta Technologies, of Stillwater, Minn. One method for forming an indium tin oxide heating element is to deposit a thin film of the material on a substrate (e.g., thin glass slide); this film is then formed into the desired pattern by etching. Typical etching solutions contain 20% HCl and 5% $HNO_3$. Premixed etching solution is available from Cyantek Corp. Alternatively, the material can be patterned by sputtering and lift off techniques that are known in the art.

ITO heating elements are useful in conducting certain analyses because of their transparency. This feature means that reactions (e.g., PCR reactions) can be monitored in real time. This capability is important because it enables quantitative information regarding expression levels to be determined (see the discussion on quantitative PCR techniques supra).

D. Chamber Thermocyclers

Certain temperature controllers are designed to cycle the temperature of an entire microfluidic device such as those disclosed herein. One such temperature controller includes a thermoelectric module (e.g., from Omega) that can be positioned adjacent a microfluidic device. This thermoelectric module is typically powered by a direct current power supply. A programmable temperature controller can be connected to the module to have the module produce the desired temperature cycle.

Another temperature controller generally consists of a thin chamber formed between two spaced-apart plates, including a top plate and a bottom plate, with the spaced-plates connected to at least one inlet and one outlet through which fluids of different temperatures can be flowed. Typically, the chamber includes two inlets positioned at one end of the chamber and an outlet through which fluid in the chamber can exit. Having two inlets means that two fluids at different temperatures can be flowed into the chamber separately and simultaneously, or that one can rapidly switch which of two fluids are introduced into the chamber. The top plate of the spaced-apart plates is intentionally made very thin so that its thermal resistance is negligible compared to that of the bottom plate and the microfluidic chip that rests upon it. As a consequence, there is little difference in temperature between the heat transport fluid and the microfluidic chip, and a negligible heating and cooling ramp, thus enabling a temperature cycle can to be established with little transition time between temperatures. The can also be appropriately thickness of the temperature controller is sized such that it can be utilized upon a standard microscope stage or similar device which has a narrow field of view, typically less than 5 mm, as well as being at least partially manufactured of optically transparent materials so that reactions within the microfluidic device can be monitored by microscopy or by other visual or spectroscopic means. Thus, the device is designed to permit simultaneous optical access in combination with the ability to both heat and cool the microfluidic device.

Figure 15A:
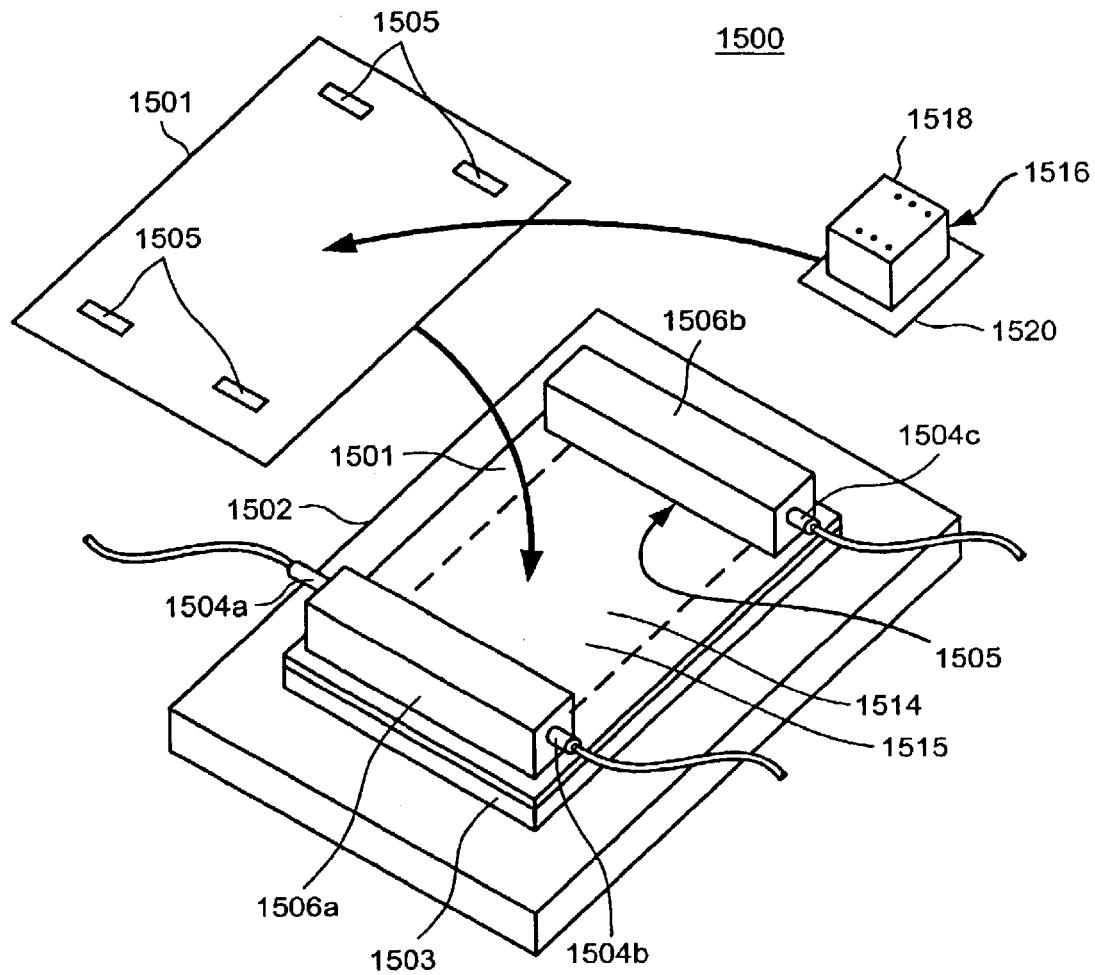
FIGS. 15A–15D show plan and cross-sectional views of an exemplary temperature controller for use with various microfluidic devices such as those disclosed herein.
Figure 15B:
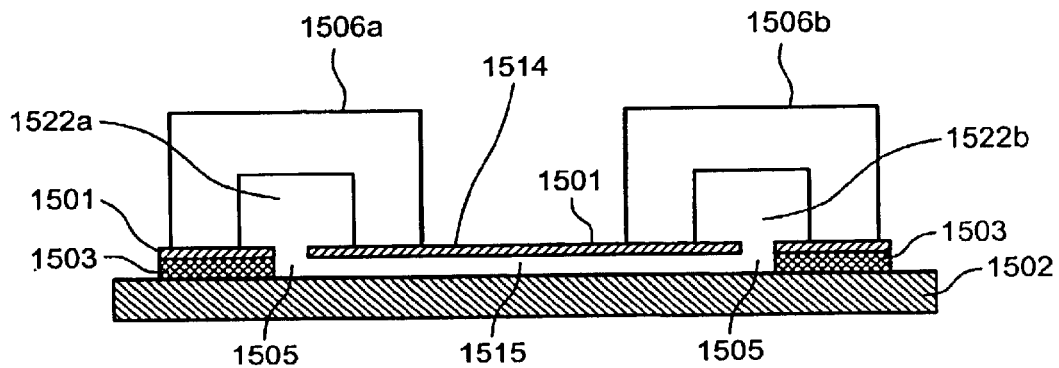

Two examples of such a device are illustrated in FIGS. 15A–15D. The first exemplary device is shown in FIGS. 15A and 15B. This particular temperature controller 1500 includes a bottom glass plate 1502 and an extremely thin (compared to the rest of the device) top glass plate 1501 of negligible thermal resistance that are spaced apart by a gasket 1503. The gasket 1503 is shaped in the form of a hollow loop and is sized such that it extends around the outer peripheral edge of the top plate 1501. Thus, the space between the bottom plate 1502 and the top plate 1501 as further defined by the peripheral gasket 1503 defines a water-tight chamber 1515.

Connector blocks 1506a and 1506b are affixed to each end of the top plate 1501. The connector blocks 1506a and 1506b each have a cavity 1522a and 1522b, respectively, that extends into the central region of one face of the connector block, without extending the entire length of the connector block. The cavity of each connector block 1506a and 1506b is positioned such that it overlays one or more holes 1505 in either end of the top plate 1501. This arrangement means that the cavity 1522a and 1522b of each connector block is in fluid communication with the chamber 1515 formed between the top plate 1501 and bottom plate 1502 via the hole(s) 1505 in the top plate. The two connector blocks 1506a and 1506b and the portion of the upper surface of the top plate 1501 extending therebetween define a bed 1514 onto which a microfluidic chip 1516 can be placed.

A first and second inlet 1504a and 1504b are inserted into opposing ends of first connector block 1506a and each is in fluid communication with the cavity 1522a of first connector block 1506a. Consequently, fluid introduced via first and second inlets 1504a and 1504b can flow into the cavity 1522a of first connector block 1506a and subsequently pass through the hole(s) 1505 in the top plate 1501 and into the chamber 1515. Similarly, an outlet 1504c is positioned in one end of the second connector block 1506b. Outlet 1504c is in fluid communication with the cavity 1522b of connector block 1506b, which means that fluid in the chamber 1515 can flow up through the hole(s) 1505 in the top plate 1501 into the cavity 1522b of second connector block 1506b where the fluid can then exit via outlet 1504c.

Inlets 1504a and 1504b are each connected to a temperature bath (not shown) by a connecting line (not shown). The temperature of the fluid in each bath is set so fluid delivered to the temperature controller will be one of the temperatures in the desired temperature cycle. Each temperature bath is further connected to a pump (not shown) to pump fluid from the temperature bath into the chamber of the temperature controller. Typically, the connecting lines are protected to guard against heat loss. One option is to include the connecting line in a flowing fixed temperature water jacket. Because the top plate is very thin, heat can be rapidly transferred to or from the microfluidic chip positioned on its upper surface. Generally the top plate 1501 is less than millimeter thick, and in other instances less 500 microns, in still other instances less than 250 microns, and in still other instances less than 100 microns.

In operation, microfluidic chip 1516 is placed into bed 1514 such that it rests against the upper face of the top plate 1501. The temperature of the temperature baths are set to the temperatures appropriate for the temperature cycle for the analysis or reaction. In the case of nucleic acid amplification reactions, the temperatures are selected to promote the different stages of the amplification process. By way of illustration but not limitation, one water bath is heated to 97° C., and the other to 60° C. Fluid from the bath at the initial temperature of the cycle is flowed into chamber 1515 via first inlet 1504a and exits via outlet 1504c. The thinness of top plate 1501 and resulting low thermal resistance permits the substrate 1520 of microfluidic chip 1516 to be heated and cooled very rapidly. When the temperature is to be changed during a temperature cycle, fluid from the second temperature bath at the next temperature in the cycle is flowed into second inlet 1504*b*, and flow of fluid from the first temperature bath is stopped. As fluid at the second temperature is flowed into chamber 1515, fluid continues to flow out of chamber 1515 via outlet 1504*c*.

Figure 15C:
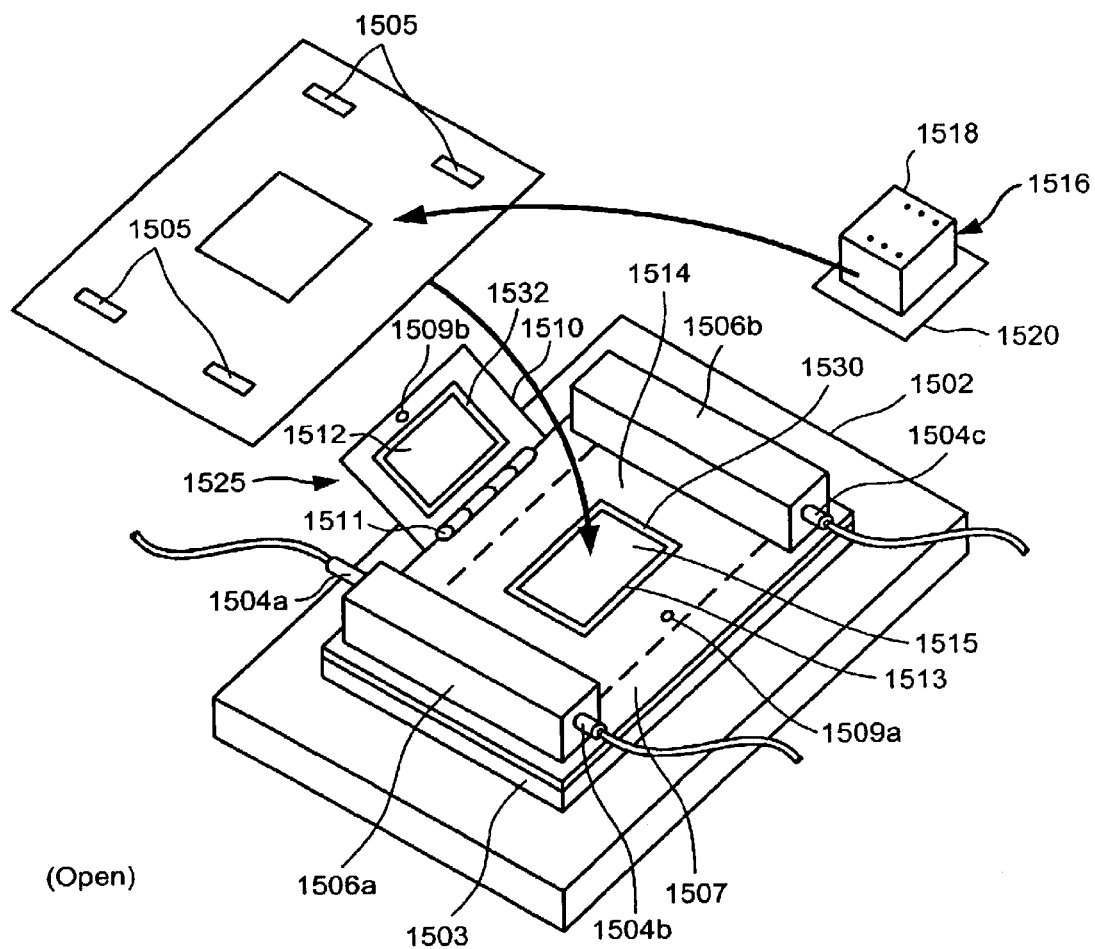
Figure 15D:
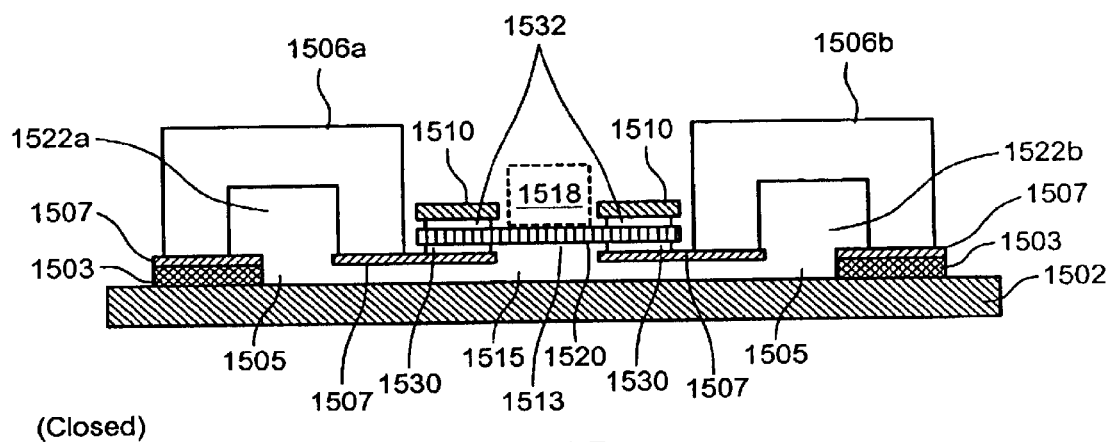

Another temperature controller 1550 is shown in FIGS. 15C and 15D and has a design similar to the device illustrated in FIGS. 15A and 15B. The primary difference is with respect to the construction of the top plate 1507. In the thermocycler shown in FIGS. 15C and 15D, the top plate 1507 is part of an assembly 1525 in which the top plate 1507 is connected by a hinge 1511 to a sealing plate 1510. For increased durability, the top plate 1507 and the sealing plate 1510 are made of metal. Because the thermocycler is preferably transparent to facilitate optical detection, both the top plate 1507 and the sealing plate 1510 contain centrally located holes 1513 and 1512, respectively (the central hole 1513 in top plate 1507 is in addition to the hole(s) 1505 located at either end). Central holes 1512 and 1513 are aligned such that when the sealing plate 1510 is folded down onto top plate 1507, the central holes 1512 and 1513 align with one another. The central hole 1513 in the top plate 1507 is sized such that it is smaller than the substrate 1520 upon which the elastomeric structure 1518 of microfluidic chip 1516 is attached. Thus, when microfluidic chip 1516 is placed in the bed 1514 defined by the upper face of the top plate 1507 and the two connector blocks 1506*a* and 1506*b*, the substrate 1520 spans the central hole 1513 of the top plate 1507. The central hole 1512 in the sealing plate 1510 is also positioned such that when microfluidic chip 1516 is placed in the bed 1514, the central hole 1512 fits around the elastomeric structure 1518, with a part of the elastomeric structure 1518 extending through the central hole 1512 of the sealing plate 1510. Latch 1509*b* is closed upon catch 1509*a*, thereby forcing the microfluidic chip 1516 against top plate 1507.

In order to prevent fluid from flowing through the central hole 1513 in the top plate 1507 and out past the edges of the microfluidic chip 1516 when it is positioned in bed 1514, two additional gaskets 1530 and 1532 are typically utilized to form a water-tight seal. A first gasket 1530 is attached to either the upper face of the top plate 1507 around the periphery of the central top plate hole 1513, or placed on the underside of the substrate 1520 of the microfluidic chip 1516 itself. A second gasket 1532, is either attached to the under surface (assuming the plate is closed) of the sealing plate 1510 and runs around the periphery of the central sealing plate hole 1512, or is simply attached to the upper surface of the substrate 1520 of the microfluidic chip 1516.

Thus, in operation, the sealing plate 1510 is lifted up away from the top plate 1507 so that microfluidic chip 1516 can be placed onto bed 1514, with the elastomeric structure 1518 of the microfluidic chip 1516 being disposed over the central hole 1513 in the top plate 1507. The sealing plate 1510 is then closed such that the underside of the sealing plate 1510 is adjacent the upper surface of the top plate 1507, with the substrate 1520 of the microfluidic chip 1516 being sandwiched therebetween, and the elastomeric structure 1518 extending up through the central hole 1512 in the sealing plate 1510. Fluids of differing temperature can then be cycled through the chamber 1515 as described with respect to the temperature controller 1500 shown in FIGS. 15A and 15B via inlets and outlet.

Because the elastomeric structure 1518 is coincident with the central top plate hole 1513 and the central sealing plate hole 1512, reactions within the microfluidic chip 1516 can be monitored by microscopy or other optical methods.

Further, as alluded to above, this particular design permits the thermocycling device to be made out of sturdier materials (e.g., metal), and is thus reusable and has a longer life than that expected for other devices such as that depicted in FIGS. 15A-B.

While the temperature controller has been described as being formed of glass or metal plates, the plates can be formed of any of a number of materials, including, but not limited to, plastics, ceramics and composite materials. However, the use of transparent materials such as glass plates (e.g., microscope coverslips) permit optical access to reactions within the microfluidic device while simultaneously providing the required temperatures, thus allowing detection of reaction products and monitoring of the reactions in real time.

Likewise, the gaskets can be formed of a number of different materials to provide an adequate seal between the bottom and top plates. Examples of suitable gasket materials or sealants include a wide variety of adhesives, such as PDMS (Polydimethly Siloxane), silicon, or appropriate epoxies.

A number of different fluids can be utilized with this type of temperature controller, provided the fluid has a sufficiently low viscosity such that it readily flows through the chamber and preferably does not form bubbles that would disrupt optical viewing. Examples of suitable fluids include a solution of water and Ethylene Glycol in equal proportions and heat transfer oil.

E. Temperature Sensors

As described above, performance of thermal cycling steps involving heating/cooling of reactants is an important part of the process of amplification of nucleic acids. In order to ensure the accuracy of these thermal cycling steps, in certain devices it is therefore useful to incorporate sensors detecting temperature in the various temperature regions.

One structure for detecting temperature in accordance with the present invention is a thermocouple. Such a thermocouple could be created as thin film wires patterned on the underlying substrate material, or as wires incorporated directly into the microfabricated elastomer material itself.

Temperature may also be sensed through a change in electrical resistance. For example, change in resistance of a thermistor fabricated on an underlying semiconductor substrate utilizing conventional techniques could be calibrated to a given temperature change. Alternatively, a thermistor could be inserted directly into the microfabricated elastomer material. Still another approach to detection of temperature by resistance is described in Wu et al. in "MEMS Flow Sensors for Nano-fluidic Applications", Sensors and Actuators A 89 152–158 (2001), which is hereby incorporated by reference in its entirety. This paper describes the use of doped polysilicon structures to both control and sense temperature. For polysilicon and other semiconductor materials, the temperature coefficient of resistance can be precisely controlled by the identity and amount of dopant, thereby optimizing performance of the sensor for a given application.

Thermo-chromatic materials are another type of structure available to detect temperature on regions of an amplification device. Specifically, certain materials dramatically and reproducibly change color as they pass through different temperatures. Such a material could be added to the solution as they pass through different temperatures. Thermo-chromatic materials could be formed on the underlying substrate or incorporated within the elastomer material. Alternatively, thermo-chromatic materials could be added to the sample solution in the form of particles.

Another approach to detecting temperature is through the use of an infrared camera. An infrared camera in conjunction with a microscope could be utilized to determine the temperature profile of the entire amplification structure. Permeability of the elastomer material to radiation would facilitate this analysis.

Yet another approach to temperature detection is through the use of pyroelectric sensors. Specifically, some crystalline materials, particularly those materials also exhibiting piezoelectric behavior, exhibit the pyroelectric effect. This effect describes the phenomena by which the polarization of the material's crystal lattice, and hence the voltage across the material, is highly dependent upon temperature. Such materials could be incorporated onto the substrate or elastomer and utilized to detect temperature.

Other electrical phenomena, such as capacitance and inductance, may be exploited to detect temperature in accordance with embodiments of the present invention.

IX. Detection

A. General

The microfluidic devices provided can be utilized in combination with a wide variety of detection methodologies. The particular detection system utilized depends upon the particular type of event and/or agent being detected. Examples of particular detection methods useful with the present microfluidic devices include, but are not limited to, light scattering, multichannel fluorescence detection, UV and visible wavelength absorption, luminescence, differential reflectivity, and confocal laser scanning. Applications can also utilize scintillation proximity assay techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

The term "detection section," "detection region," and other like terms refer to the portion of the microfluidic device at which detection occurs. In general, the detection section can be at essentially any point along one of the flow channels or at an intersection of flow channels. As indicated supra, for the devices shown in FIGS. 1 and 2, the detection section can include the central loop (FIG. 1) or a portion thereof, or one or more reaction chambers (FIG. 2). Alternatively, detection can occur at another region on the device or off the device once solution containing unreacted reagents and products has been withdrawn from the flow channel in which thermocycling has occurred.

Similarly, detection with the matrix array devices discussed above and illustrated in FIGS. 5 and 12, for example, typically occurs within regions of flow channels that are adjacent a junction or within the juctions themselves.

The detection region can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by an optical detector. The optical detector can include one or more photodiodes (e.g., avalanche photodiodes), a fiber-optic light guide leading, for example, to a photomultiplier tube, a microscope, and/or a video camera (e.g., a CCD camera).

An optical detector can be microfabricated within the microfluidic device, or can be a separate element. If the optical detector exists as a separate element and the microfluidic device includes a plurality of detection sections, detection can occur within a single detection section at any given moment. In other instances, an automated system is utilized which scans the light source relative to the microfluidic device, scans the emitted light over a detector, or includes a multichannel detector. For example, the microfluidic device can be attached to a translatable stage and scanned under a microscope objective. The acquired signal is routed to a processor for signal interpretation and processing. Arrays of photomultiplier tubes can also be utilized. Additionally, optical systems that have the capability of collecting signals from all the different detection sections simultaneously while determining the signal from each section can be utilized.

In some instances, the detection section includes a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

In some instances in which external radiation and/or an external detector is/are utilized, a substrate that is optically transparent at the wavelength being monitored is used to cover the detection section. However, by appropriate selection of elastomeric materials, monolithic elastomeric devices can still be utilized in conjunction with a wide variety of external optical detection methods. The present devices can utilize a number of optical detection systems that are not possible with conventional silicon-based microfluidic devices because the provided devices typically utilize elastomers that are substantially optically transparent.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

In certain methods, solutions are transported from the microfluidic device to a separate external device for further analysis. The external device can be any of a number of analytical devices such as UV/VIS, IR, NMR and/or ESR spectrometers; chromatographic columns (e.g., HPLC); electrophoretic columns and/or mass spectrometry, for example.

B. Detection of Amplified Nucleic Acids

When the devices provided herein are utilized to conduct nucleic acid amplification reactions, a number of different approaches can be utilized to detect amplified product. Examples of suitable approaches include the following:

1. Intercalation Dyes

One method for detecting the formation of amplified product utilizes labels, such as dyes, that only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941–1948 (1994), which is incorporated by reference in its entirety.

2. Size Separation

In this approach, amplified product can be separated from primers and other unreacted reagents and subsequently detected by utilizing various size-separation techniques. Amplified product can be readily distinguished from any unextended primer because of the significantly larger size of the amplified product. Typically, separation is achieved by withdrawing solution that has completed the thermal cycling process and that includes amplified product and introducing the withdrawn sample into a matrix capable of separating nucleic acids on the basis of size.

Some of the microfluidic devices that are provided herein incorporate a separation module that is in fluid communication with the flow channel in which thermal cycling occurred (e.g., the central flow loop or flow channel with reaction chambers; see FIGS. 1 and 2). In such modules, various size exclusion materials are packed. Typically, the size exclusion material is an electrophoretic gel matrix. Thus, for example, separation can be achieved by capillary gel electrophoresis. Of course, the size separation process can also be conducted off the microfluidic device. Thus, for instance, sample removed after thermal cycling can be separated on a dedicated capillary gel electrophoresis apparatus or via high pressure liquid chromatography (HPLC). Regardless of whether separation is achieved on the microfluidic device or off, amplified product can be detected by staining the gel with intercalating dyes (see supra) or by using labeled primers, for example.

In yet another option, the microfluidic device either includes or is in fluid communication with a microfluidic DNA sizer that employs certain of the same elastomeric elements of the present devices. These DNA sizers enable one to selectively separate different nucleic acid molecules according to size. Such sizers are discussed, for example, by Chou, et al. (1999) Proc. Natl. Acad. Sci. U.S.A. 96:11–13, which is incorporated herein by reference in its entirety for all purposes.

3. Probe-Based Detection Methods

These detection methods involve some alteration to the structure or conformation of a probe caused by hybridization of the probe to the target nucleic acid, primer extension or some other event. Specific examples of such approaches follow:

Quantitative RT-PCR. A variety of so-called "real time amplification" methods or "real time quantitative PCR" methods can also be utilized to determine the quantity of a target nucleic acid present in a sample by measuring the amount of amplification product formed during the amplification process itself. Fluorogenic nuclease assays are one specific example of a real time quantitation method which can be used successfully with the methods described herein. The basis for this method of monitoring the formation of amplification product is to measure continuously PCR product accumulation using a dual-labeled fluorogenic oligonucleotide probe—an approach frequently referred to in the literature as the "TaqMan" method.

The probe used in such assays is typically a short (ca. 20–25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. The probe is designed to have at least substantial sequence complementarity with the probe binding site on the target nucleic acid. Upstream and downstream PCR primers that bind to regions that flank the probe binding site are also included in the reaction mixture.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector.

One detector which is specifically adapted for measuring fluorescence emissions such as those created during a fluorogenic assay is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, as well as Heid, C. A., et al., *Genome Research*, 6:986–994 (1996); Gibson, U. E. M, et al., *Genome Research* 6:995–1001 (1996); Holland, P. M., et al, *Proc. Natl. Acad. Sci. USA* 4 88:7276–7280, (1991); and Livak, K. J., et al., *PCR Methods and Applications* 357–362 (1995), each of which is incorporated by reference in its entirety.

Some RT-PCR reactions are conducted in a somewhat different fashion. For example, amplified product in these reactions is detected by conducting reactions in the presence of dyes that preferentially bind to double stranded DNA (e.g., SYBR GREEN) and that only generate signal once bound. Thus, as the amplification reaction progresses, an increasing amount of dye becomes bound and is accompanied by a concomitant increase in signal.

Molecular Beacons: With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use is described further, for example, by Piatek, A. S., et al., Nat. Biotechnol. 16:359–63 (1998); Tyagi, S. and Kramer, F. R., Nature Biotechnology 14:303–308 (1996); and Tyagi, S. et al., Nat. Biotechnol. 16:49–53 (1998), each of which is incorporated by reference herein in their entirety for all purposes.

4. Capacitive DNA Detection

There is a linear relationship between DNA concentration and the change in capacitance that is evoked by the passage of nucleic acids across a 1-kHz electric field. This relationship has been found to be species independent. (See, e.g., Sohn, et al. (2000) Proc. Natl. Acad. Sci. U.S.A. 97:10687–10690). Thus, in certain devices, nucleic acids within the flow channel (e.g., the substantially circular flow channel of FIG. 1 or the reaction chambers of FIG. 2) are subjected to such a field to determine concentration of amplified product. Alternatively, solution containing amplified product is withdrawn and then subjected to the electric field.

5. Incorporation of Labeled Primers and/or Nucleotides

In certain reactions, labeled primers and/or nucleotides are utilized. Hence, product formed as the result of primer extension is labeled because of the labeled primer and/or the labeled nucleotides that are incorporated into the extension products. A wide variety of labels can be utilized to label the primer and/or nucleotides. Examples of suitable labels are listed supra in the definition section.

X. Variations

A. Types of Amplification Reactions

Although some of the foregoing discussion has focused on the use of the present microfluidic devices to conduct PCR reactions, the devices can be utilized to conduct essentially any type of amplification reaction, especially those that involve thermal cycling. The amplification reactions can be linear amplifications, (amplifications with a single primer), as well as exponential amplifications (i.e., amplifications conducted with a forward and reverse primer set).

Examples of the types of amplification reactions that can be conducted with the microfluidic devices disclosed herein include, but are not limited to, (i) polymerase chain (see generally, *PCR Technology: Principles and Applications for DNA Amplification* (H. A. Erlich, Ed.) Freeman Press, New York, N.Y. (1992); *PCR Protocols: A Guide to Methods and Applications* (Innis, et al., Eds.) Academic Press, San Diego, Calif. (1990); Mattila et al., *Nucleic Acids Res.* 19: 4967 (1991); Eckert et al., *PCR Methods and Applications* 1: 17 (1991); *PCR* (McPherson et al. Ed.), IRL Press, Oxford); and U.S. Pat. Nos. 4,683,202 and 4,683,195); (ii) ligase chain reaction (LCR) (see Wu and Wallace, *Genomics* 4:560 (1989) and Landegren et al., *Science* 241:1077 (1988)); (iii) transcription amplification (see Kwoh et al., *Proc. Natl. Acad. Sci. USA* 86:1173 (1989)); (iv) self-sustained sequence replication (see Guatelli et al., *Proc. Nat. Acad. Sci. USA*, 87:1874 (1990)); and (v) nucleic acid based sequence amplification (NASBA) (see, Sooknanan, R. and Malek, L., *BioTechnology* 13: 563–65 (1995)). Each of the foregoing references are incorporated by reference in their entirety for all purposes.

B. Multiplexing

The microfluidic devices provided herein can be utilized to conduct analyses in a variety of multiplexing format, thus allowing multiple analyses to be conducted simultaneously. Multiplexing in some formats involves preparing a microfluidic device that incorporates multiple devices of the designs described supra. Such devices are readily prepared according to the multilayer soft lithographic techniques described above. Even though a large number of the thermal cycling devices can be incorporated into a single microfluidic device, control of the multiple devices is not rendered unduly complicated. In fact, the different thermal cycling devices can be formed such that solution flow through each device can be driven by the same set of control channels.

Multiplex amplifications can even be performed with a single thermal cycling device (e.g., as illustrated in FIGS. 1 and 2). This is accomplished, for example, by utilizing a plurality of primers, each specific for a particular target nucleic acid of interest, during the thermal cycling process. The presence of the different amplified products can be detected using differentially labeled probes to conduct a quantitative RT-PCR reaction or by using differentially labeled molecular beacons (see supra). In such approaches, each differentially labeled probes is designed to hybridize only to a particular amplified target. By judicious choice of the different labels that are utilized, analyses can be conducted in which the different labels are excited and/or detected at different wavelengths in a single reaction. Further guidance regarding the selection of appropriate fluorescent labels that are suitable in such approaches include: *Fluorescence Spectroscopy* (Pesce et al., Eds.) Marcel Dekker, New York, (1971); White et al., *Fluorescence Analysis: A Practical Approach*, Marcel Dekker, New York, (1970); Berlman, *Handbook of Fluorescence Spectra of Aromatic Molecules*, $2^{nd}$ ed., Academic Press, New York, (1971); Griffiths, *Colour and Constitution of Organic Molecules*, Academic Press, New York, (1976); *Indicators* (Bishop, Ed.). Pergamon Press, Oxford, 19723; and Haugland, *Handbook of Fluorescent Probes and Research Chemicals*, Molecular Probes, Eugene (1992).

Array type devices such as those described in FIGS. 5 and 12 and accompanying text can be utilized to perform a very large number of amplification reactions at once.

C. Immobilized Polymerase

In certain devices, polymerase can be immobilized to a flow channel surface within the temperature region at which primer extension occurs. In this way, one can avoid the polymerase enzyme becoming denatured in the high temperature zone. With such an approach, one could then utilize polymerases from non-thermophile organisms. Such attachment is not possible with other microfluidic configurations in which the enzyme is used in batch and is heated to high temperature (e.g., 95° C.) in every cycle.

Treatment of the elastomeric device with HCl (0.1N, 30 min 80° C.) makes the polymer hydrophilic. This treatment breaks some of the Si—O—Si bonds in the silicone polymer used to form the device to create hydroxyl groups that are displayed on the surface of the channel. These hydroxyl groups can be derivatized with appropriate reagents (e.g. 3-Aminopropyltriethoxysilane) to introduce amino groups onto the surface. These amino groups can then be crosslinked with the amino groups of the protein using various coupling agents (e.g. glutardialdehyde). Alternatively, the polymerase enzyme can also be immobilized on the glass surface. A wide variety of methods for immobilizing proteins on different surfaces are described by Gordon, F Bickerstaff (Ed), "Immobilization of Enzyme and Cells," Humana Press Inc, 1997.

D. Immobilized Nucleic Acid

In a manner related to immobilization of polymerase within a temperature region of one of the microfluidic devices disclosed herein, nucleic acids can also be immobilized within the flow channels of the devices. Usually the nucleic acids are immobilized with a temperature zone or region at which reaction occurs (see, e.g., FIG. 1), or within a reaction chamber or junction (see, e.g., the matrix or array devices illustrated in FIGS. 5 and 12).

The particular nucleic acid immobilized to the flow channel will depend upon the nature of the analysis being conducted. In the case of nucleic acid amplification reactions, the nucleic acid can be one that is to serve as a template or can be a primer. In other instances, nucleic acids are deposited within a flow channel or array junction to function as probes that hybridize to complementary target nucleic acids that are present within the flow channel or junctions (e.g., nucleic acid extension or amplification products that are formed). Binding between a probe and target nucleic acid can be detected by a variety of methods known in the art. In some instances, the nucleic acid probes are deposited to form a type of nucleic acid microarray within a flow channel or junction. By depositing the nucleic acid probes in certain patterns, detection of the absence or presence of a particular target nucleic acid can be readily ascertained spatially, i.e, according to the location on the microarray at which a signal is generated.

Certain methods for immobilizing nucleic acids parallel the methods just described for immobilizing polymerase. Here, too, elastomeric surfaces can be treated with acid to form hydroxyl groups which can be reacted directly with activated nucleic acids or derivatized prior to reaction. Optionally, the activated surface is first reacted with a linker which is then joined to the desired nucleic acid. Use of a linker can minimize unwanted steric interferences. As an alternative to attaching the nucleic acid to an elastomeric surface, the nucleic acid can instead be attached to the substrate (e.g., glass) on which the elastomeric layer is placed. In this approach, the nucleic acid is spotted at an appropriate region on the substrate and then the elastomeric layer is overlayed on the substrate, such that the nucleic acid is positioned in the desired location of the device.

Further discussion regarding synthesis and deposition of nucleic acids to form arrays are discussed for example in the following references: Meier-Ewart, et al., Nature 361:375–376 (1993); Nguyen, C. et al., Genomics 29:207–216 (1995); Zhao, N. et al., Gene, 158:207–213 (1995); Takahashi, N., et al., Gene 164:219–227 (1995); Schena, et al., Science 270:467–470 (1995); Southern et al., Nature Genetics Supplement 21:5–9 (1999); Cheung, et al., Nature Genetics Supplement 21 :15–19 (1999); Beaucage, Tetrahedron Lett., 22:1859–1862 (1981); Needham-VanDevanter, et al., Nucleic Acids Res., 12:6159–6168 (1984); U.S. Pat. Nos. 5,143,854, 5,424,186, 5,744,305; PCT patent publication Nos. WO 90/15070 and 92/10092; Fodor et al., Science 251:767–777 (1991); and Lipshutz, et al., Nature Genetics Supplement 21:20–24 (1999).

E. Integration with Other Microfluidic Components/Devices

The microfluidic thermal cycling devices provided herein can be utilized in conjunction with a variety of other microfluidic elements such as pumps, valves, rotary pumps, separation modules and the like, particularly those manufactured from elastomeric materials such as the devices provided herein (see, e.g., PCT publication WO 01/01025). The devices can also be incorporated into microfluidic devices designed to conduct high throughput screening or cell assays, for example. Examples of such microfluidic devices into which the present devices can be incorporated are described in U.S. provisional application entitled, "Apparatus and Methods for Conducting Cell Assays," having attorney docket number 020174-003210US, and filed on even date herewith, and U.S. Provisional application entitled "Apparatus and Methods for Conducting High Throughput Screening Assays," having attorney docket number 020174-003220US, and filed on even date herewith, both of which are incorporated by reference in their entirety for all purposes.

F. Combinations of Amplification Reactions

The devices can also be utilized to amplify product amplified during a previous amplification process (e.g., a prior PCR reaction). Thus, for example, the devices can be utilized to conduct nested PCR analyses in which the PCR product from one amplification reaction acts as template for a subsequent PCR utilizing primers that hybridize to segments within the amplified product. Reactions of this type are commonly used in various diagnostic applications.

A second PCR is also needed when performing a RT PCR. Here, an initial RT PCR typically is conducted to generate a full length cDNA from a full length transcript. The resulting cDNA library or members thereof can subsequently be amplified to generate amplification products for use in cloning or for generation of hybridization probes.

G. Sample Introduction using a Chip Holder

The inlets to flow channels on certain microfluidic devices are in communication with on-chip reservoirs or wells. However, in a microfluidic device requiring the loading of a large number of solutions, the use of a corresponding large number of input tubes with separate interfacing pins may be impractical given the relatively small dimensions of the fluidic device. In addition, the automated use of pipettes for dispensing small volumes of liquid is known, and thus it therefore may prove easiest to utilize such techniques to pipette solutions directly on to wells present on the face of a chip.

Additionally, capillary action may not be sufficient to draw solutions from on-chip wells into active regions of the chip, particularly where dead-ended chambers are to be primed with material. In such embodiments, one way of loading materials into the chip is through the use of external pressurization. Again, however, the small dimensions of the device coupled with a large number of possible material sources may render impractical the application of pressure to individual wells through pins or tubing.

Figure 16:
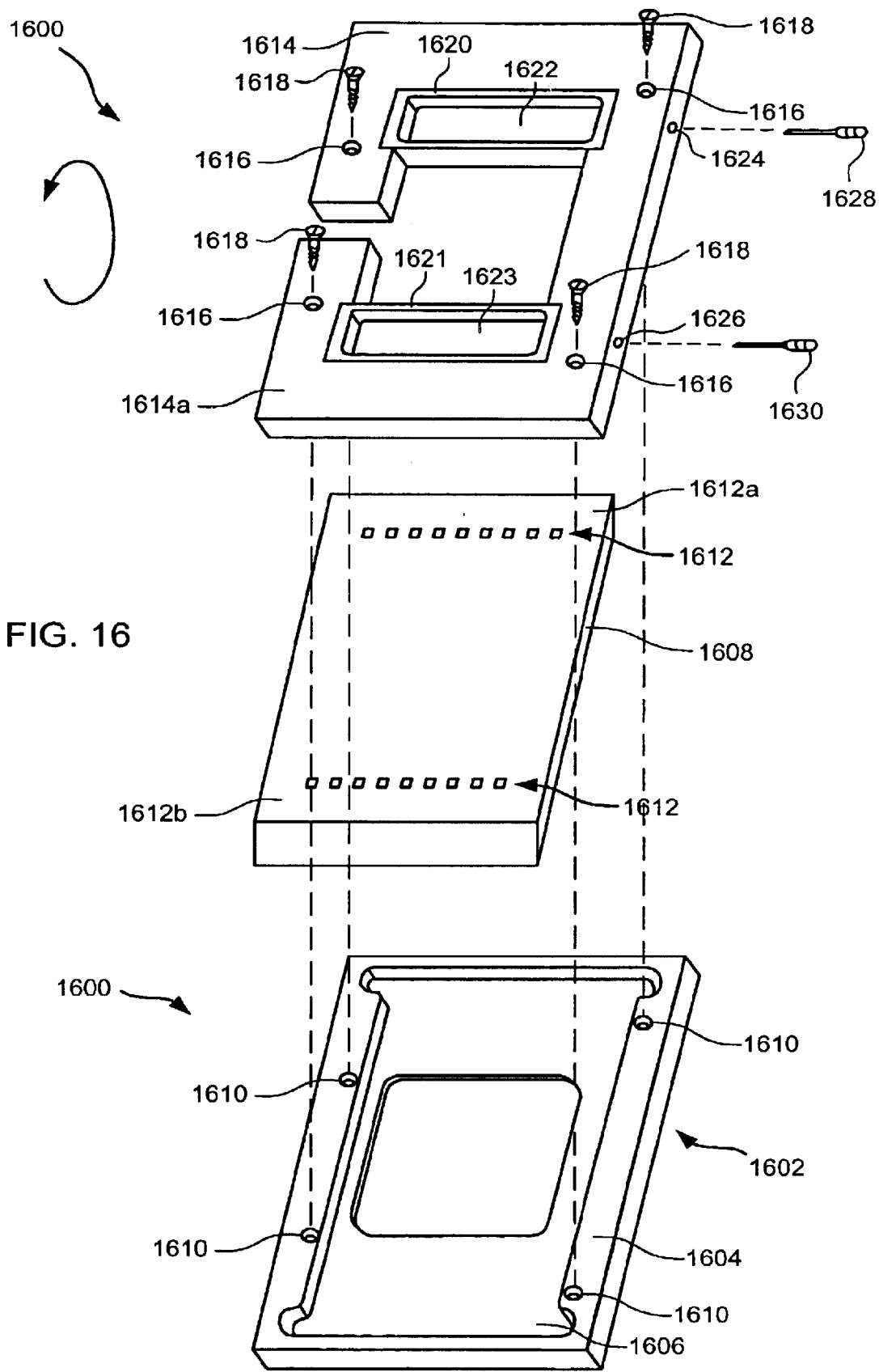
FIG. 16 illustrates a exemplary holder which forms an airtight chamber over wells or recesses in a microfluidic device, thus allowing for pressurized introduction of solutions into the microfluidic device.

Accordingly, FIG. 16 shows an exploded view of a chip holder 1600 designed to hold a chip such as those disclosed herein. Bottom portion 1602 of chip holder 1600 includes raised peripheral portion 1604 surrounding recessed area 1606 corresponding in size to the dimensions of chip 1608, allowing microfluidic chip 1608 to be positioned therein. Peripheral region 1604 further defines screw holes 1610.

Microfluidic device 1608 is positioned within recessed area 1606 of bottom portion 1602 of chip holder 1600. Microfluidic device 1608 comprises an active region that is in fluidic communication with peripheral wells 1612 configured in first and second rows 1612a and 1612b, respectively. Wells 1612 hold sufficient volumes of material to allow device 1608 to function. Wells 1612 may contain, for example, nucleic acid samples, primer solutions or various other reagents.

Top portion 1614 of chip holder 1600 fits over bottom chip holder portion 1602 and microfluidic chip 1608 positioned therein. For ease of illustration, in FIG. 16 top chip holder portion 1614 is shown inverted relative to its actual position in the assembly. Top chip holder portion 1614 includes screw holes 1616 aligned with screw holes 1610 of lower holder portion 1602, such that screws 1618 may be inserted through holes 1616 to secure the chip 1608 between portions 1614 and 1602 of holder 1600.

Lower surface 1614a of top holder portion 1614 includes raised annular rings 1620 and 1621 surrounding recesses 1622 and 1623, respectively. When top portion 1614 of chip holder 1600 is pressed into contact with chip 1608 utilizing screws 1618, rings 1620 and 1621 press into the soft elastomeric material on the upper surface of chip 1608, such that recess 1620 defines a first chamber over top row 1612a of wells 1612, and recess 1623 defines a second chamber over bottom row 1612b of wells 1612. Holes 1624 and 1626 in the side of top holder portion 1614 are in communication with recesses 1620 and 1621 respectively, to enable a positive pressure to be applied to the chambers through pins 1628 and 1630 inserted into holes 1624 and 1626, respectively. A positive pressure can thus simultaneously be applied to all wells within a row, obviating the need to utilize separate connecting devices to each well.

In operation, solutions are pipetted into the wells 1612, and then chip 1608 is placed into bottom portion 1602 of holder 1600. The top holder portion 1614 is placed over chip 11608, and is pressed down by screws. Raised annular rings 1620 and 1621 on the lower surface of top holder portion 1614 make a seal with the upper surface of the chip where the wells are located. Solutions within the wells are exposed to positive pressures within the chamber, and are thereby pushed into the active area of microfluidic device.

The downward pressure exerted by the chip holder can also prevent delamination of the chip from the substrate during loading. This prevention of delamination may enable the use of higher priming pressures.

The chip holder shown in FIG. 16 represents only one possible structure. For example, a chip holder can also include a third portion which fits over control line outlet ports on the front or back side of the chip, thereby enabling the application of pressure to control lines to control valve actuation within the chip. In addition, while the holder described in FIG. 16 includes a window for viewing of the chip, this may not be necessary if the chip is to be removed from the holder once the chip filling process is complete.

The chip holder can be equipped with heating elements to provide spatial and temporal temperature profile to the chip positioned therein. Such an alternative would eliminate the complexity and expense associated with incorporating heating elements directly onto a substrate that may be disposable.

In the particular chip holder illustrated in FIG. 16, the top piece is pressed to the chip by turning screws. However, in alternative embodiments, the downward force could be applied through a press or robotic arm, thereby potentially eliminating the need for a bottom holder piece.

Furthermore, in the particular chip holder illustrated in FIG. 16, the airtight seal over the wells allowing application of a positive pressure is created by pressing the raised ring into the compliant top surface of the elastomer chip. However, a seal could be created by the addition of flexible o-rings to the chip holder. Such o-rings would permit use of a chip holder with embodiments of microfluidic devices that feature a rigid top surface.

Finally, it is important to recognize that use of a chip holder structure in accordance with embodiments of the present invention is not limited to nucleic acid amplification, but enables loading of a large number of solutions onto a microfluidic chip for performance of a variety of applications.

Thus, in certain structures for applying pressure to a elastomeric microfluidic device comprise, a holder portion including a continuous raised rim on a lower surface thereof configured to contact a top surface of the microfluidic device and surround a plurality of material wells located therein. Contact between the raised rim and the top surface of the microfluidic device defines an airtight chamber over the material wells, an orifice in communication with the airtight chamber enabling application of positive pressure to the airtight chamber to drive the contents of the material wells into an active area of the microfluidic device.

Utilizing such holders, certain methods for priming a microfluidic device with a liquid material comprises loading a plurality of wells on an upper surface of a microfluidic device with a liquid material. A holder piece is biased against the upper surface such that a continuous raised rim of the holder piece presses against the upper surface surrounding the wells, such that an airtight chamber is created over the wells. A positive pressure is applied to the airtight chamber to drive the material from the wells into an active area of the elastomeric microfluidic structure.

An embodiment of a method of actuating a valve within a microfluidic elastomer device comprises applying a holder piece having a continuous raised rim against a surface of a microfluidic device having a plurality of control line outlets to create an airtight chamber over the outlets. A positive or negative pressure is applied to the airtight chamber to control a pressure within the control line and thereby actuate a elastomeric valve membrane of the microfluidic device that is in communication with the control line.

XI. Exemplary Applications

A. General

In some instances, the microfluidic devices described herein can be used as an analytical tool to amplify a target nucleic acid potentially present in a sample and then detect the amplified product to determine whether the target nucleic acid is present or absent in the sample. Thus, amplification serves to enhance the ability to detect target nucleic acids present at low levels. When utilized in this manner, the devices can be used in a wide variety of different applications. For example, the devices can be used in various diagnostic applications that involve a determination of whether a particular nucleic acid is present in a sample. Hence, samples can be tested for the presence of a particular nucleic acid associated with particular pathogens (e.g., certain viruses, bacteria or fungi), for instance. The devices can also be utilized for identification purposes, such as in paternity and forensic cases.

The methods and devices provided herein can also be utilized to amplify low levels of nucleic acid for further examination to detect or characterize specific nucleic acids that are correlated with infectious diseases, genetic disorders or cellular disorders (e.g., oncogenes associated with cancer). Genetic disorders are those that involve a specific deletion and/or mutation in genomic DNA. Examples of genetic diseases that can be detected include, but are not limited to, α- and β-thalassemia, cystic fibrosis and sickle cell anemia. Because the devices and methods disclosed herein can utilize very small sample volumes, they are useful in amplifying DNA samples obtained in conjunction with the prenatal diagnosis of genetic disease.

However, the amplification reactions can also be utilized as just one step of a more extensive process involving the diagnostic testing for particular target nucleic acids and in preparing sufficient nucleic acid for use in various genetic engineering applications. Hence, amplified sample can be used in a number of post amplification manipulations and analyses. Examples of such post amplification processes and analyses include, but are not limited to, sequencing of amplified products, cell-typing, DNA fingerprinting and mapping of DNA sequences.

Amplified products can also be generated for use in various genetic engineering applications. For instance, amplified product can be utilized to conduct recombination studies. In other applications, the devices are used to produce target DNA for insertion into a variety of vectors. Such vectors can then be used to transform cells for the production of desired products such as proteins, or nucleic acids in various therapeutic or biotechnological processes.

B. Sequencing

The devices can also be utilized to conduct sequencing reactions such as chain termination methods using dideoxynucleotides. Sequencing reactions utilizing the devices disclosed herein can be conducted in different formats. One approach is to conduct four separate sequencing reactions, a separate reaction being conducted in four different thermal cycling devices as provided herein. Each of the four reactions contains target nucleic acid, a primer complementary to the target, a mixture of one dideoxynucleotide (ddNTP) (optionally labeled) with its counterpart deoxynucleotide (dNTP), and the other three dNTPs. Thus, each one of the reactions is conducted with a different ddNTP/dNTP mix. Following completion of the primer extension reactions, the different sized extension products can be separated by capillary gel electrophoresis. This separation can be performed in a separation module as described supra that is integrated with the present devices or in a stand alone capillary gel electrophoresis apparatus.

The devices can also be utilized in more streamlined formats in which reactions are conducted simultaneously in a single thermal cycling device using differentially labeled dideoxynucleotides. The resulting mixture of chain-terminated reaction products are then separated on a single capillary gel electrophoresis column. The identity of the dideoxynucleotide incorporated into the primer can be determined on the basis of the label.

C. Restriction Digests

Restriction digests of nucleic acids can also be conducted with the present devices. Temperature control in such reactions initially involves controlling the temperature within the device at a temperature that promotes the activity of the restriction enzyme (e.g., 1–3 hours at 30–50° C. depending upon the particular enzyme. The other temperature is selected to promote enzyme deactivation (e.g., 60° C. for 20 minutes).

D. SNP Analyses

Analyses to determine the identity of a nucleotide present at a polymorphic site (i.e., the site of variation between allelic sequences) can also be conducted with certain of the present devices. Often these analyses are conducted using single base pair extension (SBPE) reaction. A number of SPBE assays have been developed, but the general approach is quite similar. Typically, these assays involve hybridizing a primer that is complementary to a target nucleic acid such that the 3' end of the primer is immediately 5' of the variant site or is adjacent thereto. Extension is conducted in the presence of one or more labeled non-extendible nucleotides that are complementary to the nucleotide(s) that occupy the variant site and a polymerase. The non-extendible nucleotide is a nucleotide analog that prevents further extension by the polymerase once incorporated into the primer. If the added non-extendible nucleotide(s) is(are) complementary to the nucleotide at the variant site, then a labeled non-extendible nucleotide is incorporated onto the 3' end of the primer to generate a labeled extension product. Hence, extended primers provide an indication of which nucleotide is present at the variant site of a target nucleic acid. Such methods and related methods are discussed, for example, in U.S. Pat. Nos. 5,846,710; 6,004,744; 5,888,819; 5,856,092; and 5,710,028; and in WO 92/16657.

Using devices as described herein, the temperature within a temperature control region can be selected to promote the primer annealing, primer extension and denaturation steps involved in these particular analyses, and thus allows these extension reactions to be conducted in a thermal cycling format.

E. Non-Nucleic Acid Analyses

While the foregoing discussion of the matrix or array microfluidic devices has focused on their utility in conducting a large number of nucleic acid amplification reactions, it will be appreciated by those with ordinary skill in the art that such microfluidic devices can be utilized to conduct a wide variety of types of reactions and screening methods. Thus, by way of illustration but not limitation, the devices can be utilized to conduct synthetic reactions between a plurality of reactants. Using the device shown in FIG. 12, for instance, a first set of reagents can be introduced into the horizontal flow channels, a second set of reagents can be introduced into the vertical flow channels that have an independent inlet; and a third reagent can be introduced into the vertical flow channels that are connected to the shared inlet. Using the metering technique discussed above, these various reagents can be combined within the junctions or reactant chambers for reaction.

The devices can also be utilized to screen compounds for a desired activity. With the devices described in FIGS. 5 and 12 for example, typical screening methods involve introducing a set of test compounds into the horizontal flow channels, with another set of compounds, cells, vesicles or the like being introduced via the vertical flow channels. Mixing occurs at the junctions and the presence or absence of the desired activity can then be monitored at the junction.

For instance, a wide variety of binding assays can be conducted utilizing the microfluidic devices disclosed herein. Interactions between essentially any ligand and anti-ligand can be detected. Examples of ligand/antiligand binding interactions that can be investigated include, but are not limited to, enzyme/ligand interactions (e.g., substrates, cofactors, inhibitors); receptor/ligand; antigen/antibody; protein/protein (homophilic/heterophilic interactions); protein/nucleic acid; DNA/DNA; and DNA/RNA. Thus, the assays can be used to identify agonists and antagonists to receptors of interest, to identify ligands able to bind receptors and trigger an intracellular signal cascade, and to identify complementary nucleic acids, for example. Assays can be conducted in direct binding formats in which a ligand and putative antiligand are contacted with one another or in competitive binding formats well known to those of ordinary skill in the art. Binding assays can be conducted in heterogenous formats, as well as homogenous formats. In the homogeneous formats, ligands and antiligands are contacted with one another in solution and binding complexes detected without having to remove uncomplexed ligands and antiligands. Two approaches frequently utilized to conduct homogenous assays are fluorescence polarization (FP) and FRET assays.

Immunological assays are one general category of assays that can be performed with certain of the microfluidic devices disclosed herein. Some assays are conducted to screen a population of antibodies for those that can specifically bind to a particular antigen of interest. In such assays, a test antibody or population of antibodies is contacted with the antigen. Typically, the antigen is attached to a solid support. Examples of immunological assays include enzyme linked immunosorbent assays (ELISA) and competitive assays as are known in the art.

A variety of enzymatic assays can be performed using some of the devices disclosed herin. Such enzymatic assays generally involve introducing an assay mixture containing the necessary components to conduct an assay into a flow channel or jucention for reaction with an enzyme that is subsequently introduced. The assay mixtures typically contain the substrate(s) for the enzyme, necessary cofactors (e.g., metal ions, NADH, NAPDH), and buffer, for example. If a coupled assay is to be performed, the assay solution will also generally contain the enzyme, substrate(s) and cofactors necessary for the enzymatic couple.

A number of different cell reporter assays can be conducted with the provided microfluidic devices. One common type of reporter assay that can be conducted include those designed to identify agents that can bind to a cellular receptor and trigger the activation of an intracellular signal or signal cascade that activates transcription of a reporter construct. Such assays are useful for identifying compounds that can activate expression of a gene of interest. Two-hybrid assays, discussed below, are another major group of cell reporter assays that can be performed with the devices. The two-hybrid assays are useful for investigating binding interactions between proteins.

Cells utilized in screening compounds to identify those able to trigger gene expression typically express a receptor of interest and harbor a heterologous reporter construct. The receptor is one which activates transcription of a gene upon binding of a ligand to the receptor. The reporter construct is usually a vector that includes a transcriptional control element and a reporter gene operably linked thereto. The transcriptional control element is a genetic element that is responsive to an intracellular signal (e.g., a transcription factor) generated upon binding of a ligand to the receptor under investigation. The reporter gene encodes a detectable transcriptional or translational product. Often the reporter (e.g., an enzyme) can generate an optical signal that can be detected by a detector associated with a microfluidic device.

In addition to the assays just described, a variety of methods to assay for cell membrane potential can be conducted with the microfluidic devices disclosed herein. In general, methods for monitoring membrane potential and ion channel activity can be measured using two alternate methods. One general approach is to use fluorescent ion shelters to measure bulk changes in ion concentrations inside cells. The second general approach is to use of FRET dyes sensitive to membrane potential.

Assays of cell proliferation can also be monitored with certain of the microfluidic devices disclosed herein. Such assays can be utilized in a variety of different studies. For example, the cell proliferation assays can be utilized in toxicological analyses, for example. Cell proliferation assays also have value in screening compounds for the treatment of various cell proliferation disorders including tumors.

The microfluidic devices disclosed herein can be utilized to perform a variety of different assays designed to identify toxic conditions, screen agents for potential toxicity, investigate cellular responses to toxic insults and assay for cell death. A variety of different parameters can be monitored to assess toxicity. Examples of such parameters include, but are not limited to, cell proliferation, monitoring activation of cellular pathways for toxicological responses by gene or protein expression analysis, DNA fragmentation; changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis.

By contacting various microbial cells with different test compounds, some of the devices provided herein can be used to conduct antimicrobial assays, thereby identifying potential antibacterial compounds. The term "microbe" as used herein refers to any microscopic and/or unicellular fungus, any bacteria or any protozoan. Some antimicrobial assays involve retaining a cell in a cell cage and contacting it with at least one potential antimicrobial compound. The effect of the compound can be detected as any detectable change in the health and/or metabolism of the cell. Examples of such changes, include but are not limited to, alteration in growth, cell proliferation, cell differentiation, gene expression, cell division and the like.

Additional discussion of biological assays that can be conducted with certain of the microfluidic devices disclosed herein is provided in commonly owned PCT application PCT/US01/44869, filed Nov. 16, 2001.

The following examples are provided to describe in greater detail certain aspects of the methods and devices disclosed herein.

EXAMPLE 1

This example illustrates one method of fabricating a microfluidic device comprising a rotary microfluidic channel and a temperature controller (e.g., heater).

A glass slide was gas phase treated with HMDS and Shipley SJR 574 was spun onto the glass slide. After photolithography and developing, tungsten was sputtered on the slide after removal of the photoresist (under the tungsten) with acetone. Contacts between the electrical lines running from the power supply and the heaters are made with conductive epoxy (Chemtronics, Kennesaw, Ga.).

A device having the configuration shown in FIG. 1 was prepared as follows. Air and fluid mother molds (for formation of control and flow channels, respectively) were fabricated on silicon wafers by photolithography. Photoresist (Shipley SJR5740) was spun onto the silicon substrate at spin rates corresponding to the desired channel heights. After photolithography, intrusive channels made of photoresist were formed. Fluid channel molds were baked on a hot plate of 200° C. for 30 minutes such that the photoresist could reflow and form a rounded shape, which is important for a complete valve closure (see, M. A. Unger, et al. (2000) Science 288:113–116). A one minute trimethylchlorosilane (TMCS) vapor treatment was applied to these molds before each RTV replication process to prevent adhesion of cured RTV to the photoresist. With this protective coating, molds can be reused many times.

30:1 GE-RTV 615A:615B was spun on a fluid channel mold at 2,000 RPM, which covers the photoresist channel and leave a thin membrane on top of it. At the same time, 3:1 GE-RTV 615A:615B was poured onto an air channel mold. After baking both in an oven of 80° C. for 20 minutes, the block of 3:1 RTV with air channels at the bottom was peeled off from the second mold. Air supply through-holes were punched. Aligned to the fluid pattern under a microscope, it was then pressed against the thin 30:1 RTV on the first mold. A post-bake of an hour at 80° C. made the two silicone pieces chemically bond to each other. After peeling it off from the mold and punching the fluid through-holes, the monolithic RTV device was subjected to an HCl treatment (0.1 N, 30 min. at 80° C.). This treatment breaks some Si—O—Si bonds and displays them on the surface of the channel. This helps make the polymer more hydrophilic, thereby enhancing solution flow through the channel. The monolithic device was then hermetically sealed to the glass cover slip upon which the heaters had previously been sputtered.

As illustrated in FIG. 1, samples containing or potentially containing target nucleic acids (e.g., DNA), amplification reagents and agents for detection of unreacted reagents and/or products can enter from the two branches of the top T-channel. On/off states of each microvalves can be controlled by external pneumatic valves (Lee LHDA1211111H) which either apply 100-kPa air pressure to the microvalves or vent them to the atmosphere. A maximum cycling frequency of 75 Hz has been demonstrated with complete opening and closing of the valves (see, e.g., L. C. Waters, et al. (1998) *Analytical Chemistry.*, 70:158).

EXAMPLE 2

This method illustrate another method of fabricating a microfluidic device comprising a rotary microfluidic channel and a temperature controller (e.g., heater).

Figure 7A:
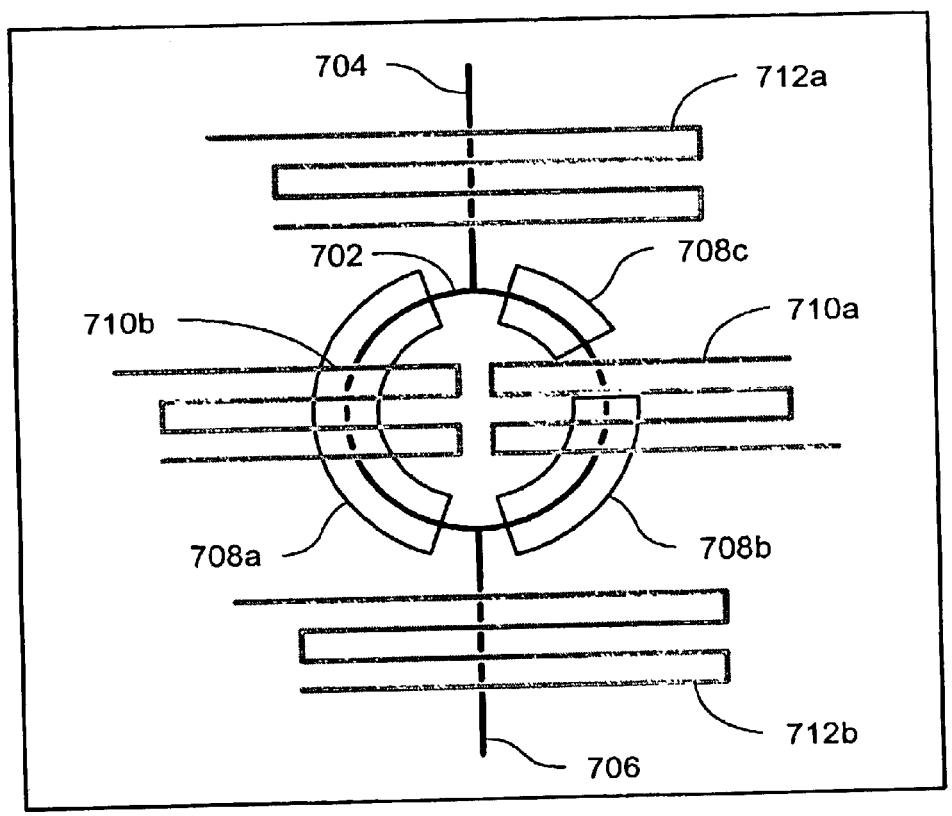
FIG. 7A is a schematic representation of an exemplary microfluidic device comprising a rotary channel, pumps and heaters. Three heaters arranged in the following order (clockwise from upper right): denaturation, annealing, and extension. (In the 2-step Taqman PCR, only the two heaters for denaturation and extension were used.)

The rotary microfluidic devices were fabricated by multilayer soft lithography techniques (Unger, M. A. et al., *Science*, 288:113–116 (2000); Chou, H. P. et al., Proceedings of the Solid State Sensor and Actuator Workshop, Hilton Head, S.C. (2000)). The channel pattern of the device is shown in FIG. 7A. As can be seen, the device 700 includes a circular flow channel 702 in fluid communication with an inlet 704 and an outlet 706. The flow channel 702 overlays three resistive heaters 708a, 708b and 708c, each defining a different temperature region and having a different length. S-shaped control channels 710a and 710b overlay the circular flow channel 702 to form pumps for flowing fluid through the circular flow channel 702. The control channels 712a and 712b overlaying the inlet 704 and outlet 706 serve to introduce and withdraw solution from the main flow channel.

The masks for making the flow channel were printed on transparency films by a high resolution printer (3556 dpi). Photoresist (Shipley SJR5740) was spun onto the silicon wafer, which had been pretreated with HDMS, at 3000 RPM for 60 seconds. After preheating at 90° C. for 1 hour, the channel pattern was exposed onto the wafer with a mask aligner (Karl Suss). The pattern was developed by 5:1 (v/v) developing solution (Shipley 2401). Then the wafer was put onto a hot plate for 30 min to round the remaining photoresist.

Figure 7B:
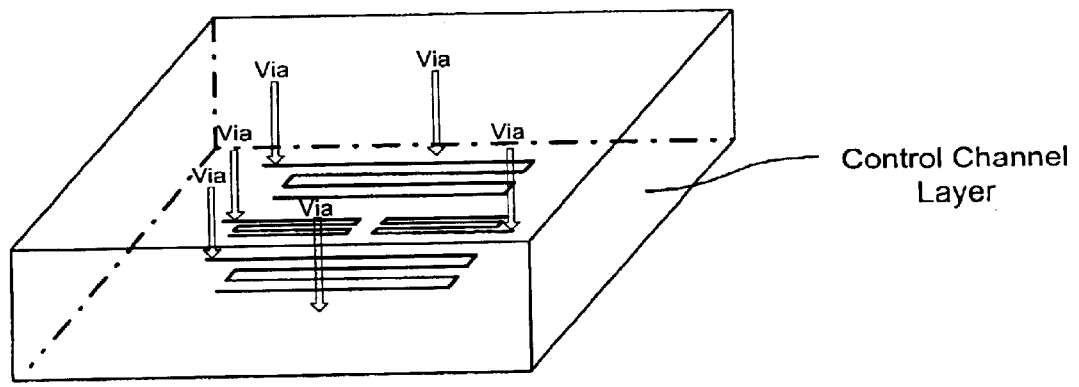
FIG. 7B is a schematic representation of assembly of the rotary microchip and the heaters showing control layer, flow layer, glass cover-slip and heaters, with arrows indicating the air and fluid vias (i.e., the openings in the layer which connect to a flow or control channel).
Figure 7B:
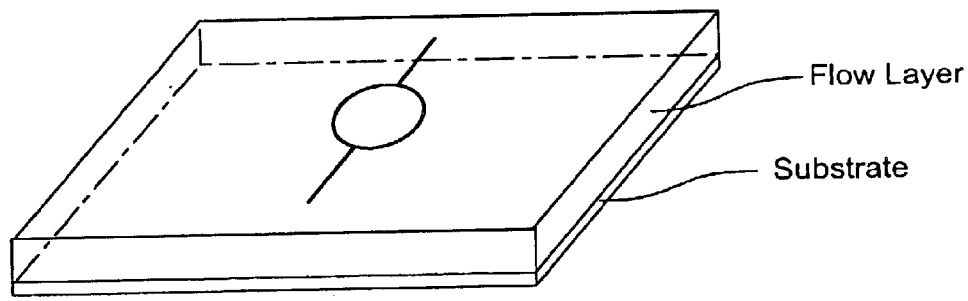
Figure 7B:
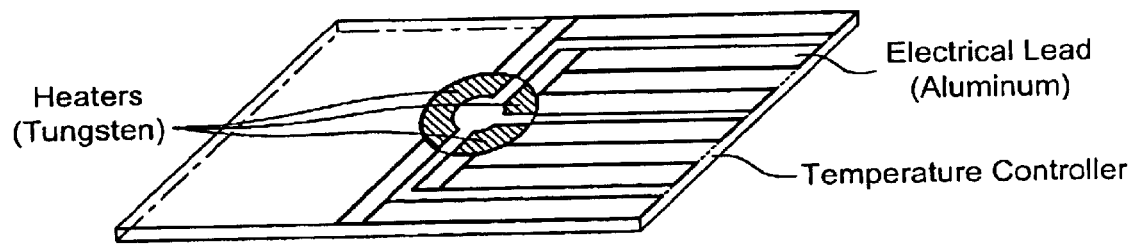

As represented in FIG. 7B, 20:1 RTV 615(GE) was spun on a flow channel mold at 2,000 RPM; while 5:1 RTV (GE) was spun on a control channel mold, then 10:1 RTV (GE) was poured onto it. After baking them in an oven of 80° C. for 1.5 hour, the RTV block on the latter mold was peeled off to punch air supply vias. Then it was aligned and pressed against the thin RTV layer on the former mold. After a post-bake at 80° C. for 2 hours, the multilayer RTV was peeled off the mold to punch fluid vias. Finally, the device was made by sealing the multilayer RTV onto a glass coverslip at 80° C. for 2 hours.

The on-chip valves were actuated with a pneumatic controller supplied by Fluidigm, Inc. The Fluid Controller system allowed selective actuation of valves to seal off the loop as well as peristaltic pumping at variable rates within the loop. Typical actuation pressures were 10 psi; the pumping frequency was 30 Hz.

The pattern of heaters is shown in FIG. 7B. They were made of thin layers of tungsten (heating component) and aluminum (electrical leads) sputtered onto a glass microscope slide. Similar to the fluidic fabrication, a negative pattern of photoresist was developed onto a piece of a glass microscope slide (40 mm×26 mm×1.1 mm). Then a thin layer (~500 Angstroms) of tungsten was deposited on the sample by a DC sputter system. After that, acetone was used to clean off the remaining photoresist in order to get the designed tungsten pattern. The procedure was repeated in order to sputter another thin layer of aluminum as the electrical leads for the heater.

The heaters were calibrated via a two step process. After the fluidic device was attached to the heaters, thermochromic liquid crystals (TLC) were pumped into the channels of the device. The TLC were then imaged at various heater currents with a color camera (KR222, Panasonic) and a stereomicroscope (ASA012-3449, Japan). The temperature response of the TLC were separately calibrated with a thermistor and hot plate. Briefly, images of the beads were digitized and average hues of the beads were calculated, with outliers discarded. Hue and temperature have a fairly linear relationship from 75–100 degrees, sufficient to determine the denaturing temperature. The lower annealing/extension temperature was extrapolated from this curve.

During Taqman PCR, the denaturing temperature was set at 95° C., and the annealing temperature at 60° C. Two independent resistive heaters were used to heat the microchip to set temperatures. The output power of the heaters was adjusted by the voltage: around 380 mW (12.6V) and 75 mW(7.0V), respectively.

EXAMPLE 3

This example illustrates Taqman PCR assay using the microfluidic device of Example 2 having two distinct temperature zones.

The Taqman PCR technique exploits the 5'-3' nuclease activity of AmpliTaq Gold DNA polyrnerase to allow direct detection of PCR product by the release of a fluorescent reporter during PCR (Protocol of TaqMan PCR Reagent Kit with AmpliTaq Gold DNA Polymerase, Applied Biosystems. http://www.appIiedbiosystems.com. (2001)). An advantage of using this kit is that the increase in fluorescence during POR quantitatively reflects the amount of product created. The probe was an oligonucicotide containing a report dye, 6-carboxyfluorescein (FAM) in the 5' end and a quencher dye, 6-carboxytetramethylrhodamifle, in the 3' end. The excitation wavelength was 488 nm, while the emission wavelength of the reporter dye and quencher dye were 518 nm and 582 nm, respectively. The template, Human DNA Male, was provided with the kit. The target was portion of the β-actin gene; forward primer and reverse primer were the following: 5'-TCA CCC ACA CTG TGC CCA TCT ACG A-3' (SEQ ID NO:1) and 5-'CAG CGG AAC CGC TCA TTG CCA ATG G-3' (SEQ ID NO:2), respectively. A segment of DNA about 294 bp was amplified. Typical PCR reagent conditions were as follows (50-$\mu$L volumes): template, 0.1 ng/$\mu$L; primers, 300 nM; $Mg^{2+}$, 3.5 mM; dATP, 200 $\mu$M; dCTP, 200 $\mu$M; dGTP, 200 $\mu$M; dUTP, 400 $\mu$M; AmpliTaq Gold, 0.025 U/$\mu$L; AmpErase UNG, 0.01 U/$\mu$L; Probe, 200 nM. A benchtop PCR machine (PTC200 Peltier Thermal Cycler, MJ Research) was used to check the Taqman PCR kit by the manufacturer's protocol: 2 minutes at 50° C.; 10 minutes at 95° C.; 40 cycles: 15 seconds at 95° C.; 1 minute at 60° C.

Figure 8:
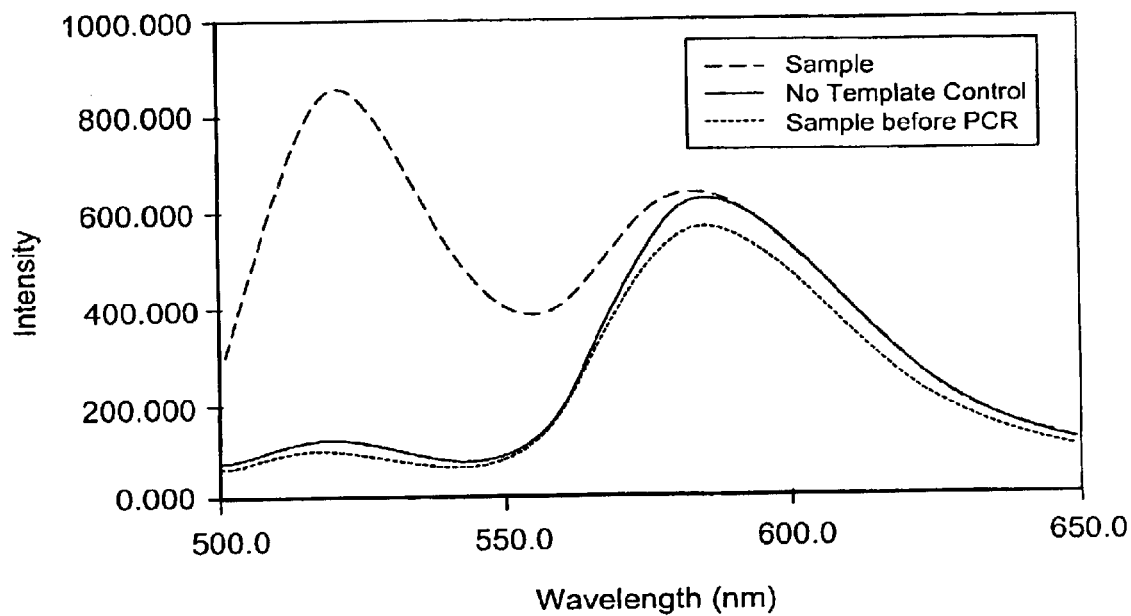
FIG. 8 is a graph showing bulk confirmation of the Taqman amplification of the human $\beta$-actin gene fragment.
Figure 9A:
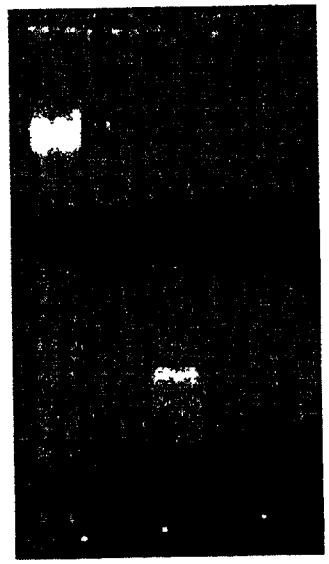
FIGS. 9A and 9B show gel electrophoresis analysis of bulk PCR products.

FIGS. 8 and 9A show the emission spectrum and gel electrophoresis results, respectively, of the PCR product by ordinary PCR machine. The emission spectra in FIG. 8 show the sample and the negative control (no template). The fluorescent peak at 525 nm appears in the sample with the template, while there is no peak for the control. In FIG. 9A, lane 1 (left) is that of human β-actin Taqman PCR amplicon: 123 bp DNA ladder; lane 3 (middle) is that of a sample; and lane 5 (right), which is nearly invisible is no template control.

EXAMPLE 4

This example illustrates Taqman PCR assay using the microfluidic device of Example 2 having three temperature zones.

A segment (199-bp) of λ phage DNA was selected for amplification; forward primer and reverse primer were the following: 5'-GGT TAT CGA AAT CAG CCA CAG CGC C-3' (SEQ ID NO:3) and 5'-GGA TAG GTC TGA ACT GGT CAC-3' (SEQ ID NO:4), respectively (Khandurina, J. et al., *Anal. Chem.*, 72:2995–3000 (2000)). Typical PCR reagent conditions were as follows (100-μL volumes): template, 2 ng/μL; primers, 500 nM; $Mg^{2+}$, 1.5 mM; dNTP, 200 μM; Taq polymerase, 0.025 U/μL (Qiagen); An intercalating dye, Syhr Green I (Molecular Probes), was added to the reagent mixture using a 1:10,000 dilution of the stock reagent.

Figure 9B:
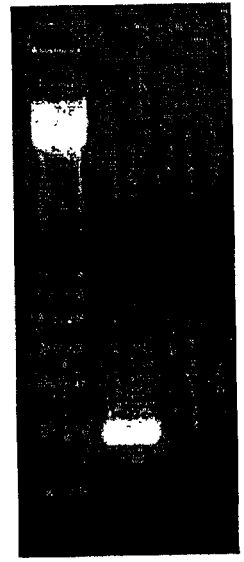

For amplification by benchtop PCR machine, the temperature steps were set as follows: 2 minutes at 94° C.; 30 cycles: 30 seconds at 94° C.; 30 seconds at 55° C.; 1 minute at 72° C.; and 10 minutes at 72° C. finally. FIG. 9B shows the gel electrophoresis result of the PCR product of phage DNA by this method. In FIG. 9B, lane 1 (left) is that of 123 bp DNA ladder; lane 2 (middle) is that of λ-DNA amplicon; and lane 3 (right) is that of no template control. The sample and the control were displayed in 2% Agarose gel (Model 1A, easy-cast™). All samples were treated with Sybr Green I stain. The picture was taken by the Kodak electrophoresis documentation and analysis system.

EXAMPLE 5

This example illustrates real-time measurement of PCR products using a microfluidic device of Example 2.

After having injected the reagent mixture into the microchip, the rotary microfluidic channel (i.e., loop) circulation was operated with the Fluid Controller (Fluidigm) and turned on the power supply for the heaters. The fluorescence change inside the channel was imaged by a high resolution camera (ST-7, Santa Babara Instruments Group) assembled on a fluorescence microscope (IX50, Olympus) every a few minutes during the process of PCR. The filters (Chroma) in the fluorescence microscope were chosen as follows: Exciter, HQ 470/40x; Dichroic, Q 495LP; Emitter, HQ 525/50m. The snap pictures were analyzed with the CCDOPS (SBIG) software.

As shown schematically in FIG. 7, the flow channel is a central loop (i.e., rotary microfluidic channel) with an inlet and an outlet. In this particular example, the channel width of the central loop is asymmetrical: 120 mm on the left; 70 μm on the right. In such a pattern, the fluid velocities in the two parts are different from each other. Therefore, the time that the fluid resides in different temperature zones can be adjusted either by the width of flow channel or the length of the heater. The fluid motion in the channel was characterized by using a solution of 2.5 μm beads. In order to mimic the actual conditions of the assay, we used the same concentration of Taqman PCR buffer and Human DNA (male) in the bead solution. At room temperature, the speed of beads was about 3.4 mm/second in the narrow channel and 1.5 mm/second in the wide channel. However, it was slowed down to 25%–30% of the above velocity when the device was run at its operating temperatures, resulting in about 20–30 seconds per full cycle.

In the control layer, three separate valves were used to create the peristaltic pump. Alternatively, one S-shaped valve can also accomplish the same peristaltic pumping as three separate valves. In addition, the S-shape channels provide more secure closing of the inlet and outlet than a single channel.

In each of the experiments one portion of the flow channel was selected to observe the fluorescence change. The CCDOPS software provided a way to get the intensity values inside the channel and outside the channel by sampling the different regions of the picture. The intensity value outside the channel was subtracted as a measure of the background.

Spatial Cycling

Figure 10:
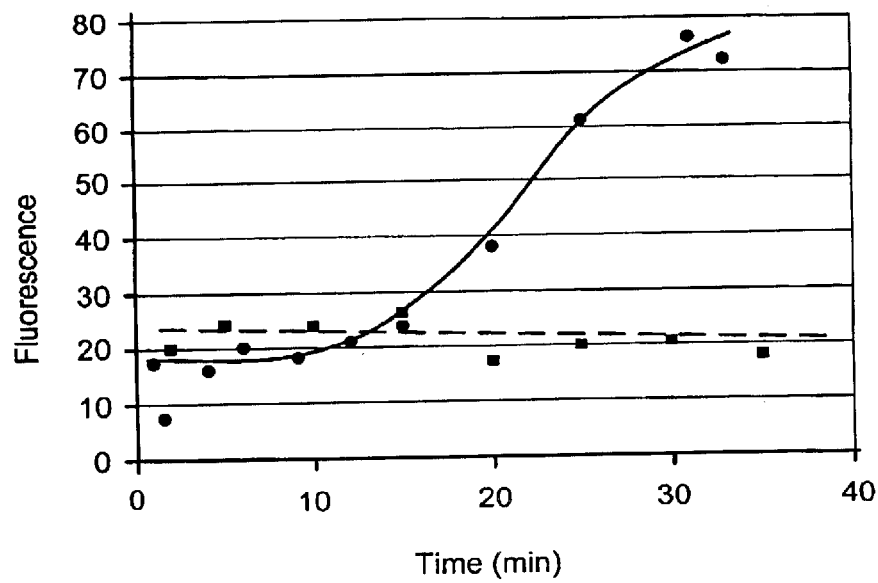
FIG. 10 is a graph of fluorescence increase in a spatially cycled Taqman assay performed using a microfluidic device as provided herein.

The microfluidic device described above was used in the spatial cycling mode to amplify a fragment of the human β-actin gene using the Taqman assay. After running the rotary pump in the microchip for about 10 minutes, a rapid increase in fluorescence was observed. As shown in FIG. 10, there was a more than four fold increase in fluorescence intensity in the presence of the sample template, while the no-template control remained flat. In FIG. 10, dot represents sample and square represents no template control. The curves are a guide for the eye.

Calibration experiments showed that the recorded increase in fluorescence was comparable to that of 30–35 cycles of PCR product by a benchtop PCR machine (PTC200 Peltier Thermal Cycler, MJ Research) (FIG. 10).

Figure 11A:
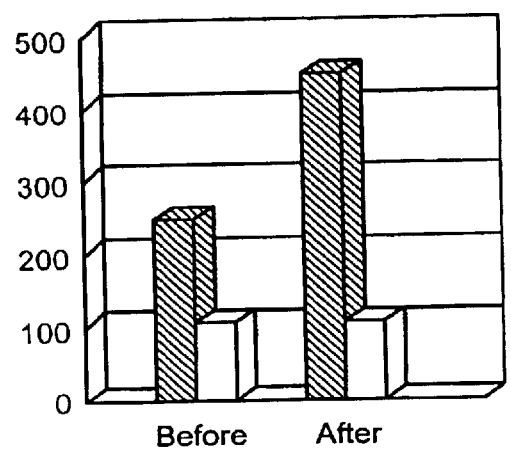
FIG. 11A shows a bar graph of results of three-temperature spatial cycling PCR of a segment of $\lambda$ DNA.

The microfluidic device was also used to perform a three temperature PCR assay in which the creation of product was directly monitored by observing the product via an intercalating dye. The reagents were pumped through three different temperature zones as follows: denaturing (94° C.) and annealing (55° C.) extension (72° C.). A fragment of λ DNA was amplified by Taq Polymerase while the PCR product was investigated with Sybr Green I. FIG. 11A shows the fluorescence difference before and after PCR process, and indicates that some amplification occurs relative to the no template control. FIG. 11A shows fluorescence measured in the channel before and after 40 minutes of pumping, where the dark bar represents PCR process with DNA template and the white bar represents control without template.

Temporal Cycling

Figure 11B:
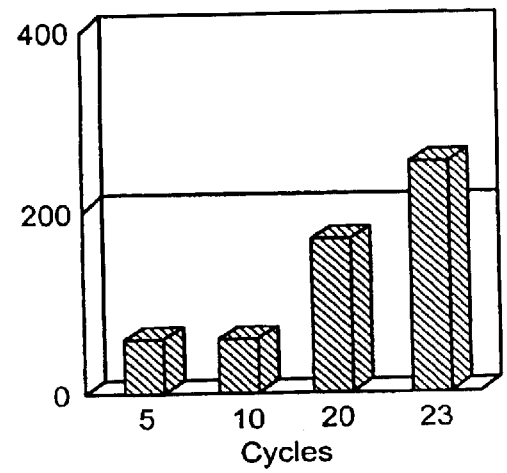
FIG. 11B shows a bar graph of results of three-temperature temporal cycling PCR of a segment of $\lambda$ DNA.

The same segment of λ phage DNA was amplified using the microfluidic described above. After having injected the reagent mixture into the microfluidic device, the inlet and outlet valves were closed. The central loop was heated and cooled repeatedly without circulating the sample within the loop. The heaters were calibrated to the set temperatures by choosing a set of voltages; the temperature steps were as follows: 15 seconds at 94° C.; 30 seconds at 55° C.; and 30 seconds at 72° C. Each cycle took about 6 minutes and 23 cycles were conducted in the experiment. The change of fluorescence during PCR was monitored by the same setup every a few cycles. The fluorescence increased dramatically during the experiment as shown in FIG. 11B.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A microfluidic device, comprising:
   (a) a substrate comprising an elastomeric material;
   (b) a flow channel disposed within the substrate, the flow channel
      configured such that a sample introduced into the flow channel can be cycled around the flow channel; and comprising a plurality of temperature regions at which temperature can be regulated, each temperature region located at a different location along the flow channel;
   (c) an inlet in fluid communication with the flow channel via which the sample can be introduced into the flow channel; and
   (d) a temperature controller operatively disposed to regulate temperature within at least one of the plurality of temperature regions.

2. The microfluidic device of claim 1, further comprising a pump operatively disposed to transport fluid through the flow channel.

3. The microfluidic device of claim 1, further comprising one or more control channels, and wherein the pump comprises one or more of the control channels, each of the control channels of the pump formed within an elastomeric material and separated from the flow channel by a section of an elastomeric membrane, the membrane being deflectable into or retractable from the flow channel in response to an actuation force applied to the control channel.

4. The microfluidic device of claim 1, wherein the flow channel is substantially circular.

5. The microfluidic device of claim 4, wherein at least one of the temperature regions differs in length from the other temperature regions.

6. The microfluidic device of claim 4, wherein the size of the substantially circular flow channel is enlarged in the plurality of temperature regions relative to the regions of the substantially circular flow channel outside of the plurality of temperature control regions.

7. The microfluidic device of claim 4, further comprising a pump operatively disposed to transport fluid through the substantially circular flow channel, and one or more control channels, and wherein the pump comprises one or more of the control channels, each of the control channels of the pump formed within an elastomeric material and separated from the substantially circular flow channel by a section of an elastomeric membrane, the membrane being deflectable into or retractable from the substantially circular flow channel in response to an actuation force applied to the control channel.

8. The microfluidic device of claim 1, further comprising a plurality of reaction chambers disposed along the flow channel and in fluid communication therewith, and wherein each reaction chamber is located within one of the temperature regions.

9. The microfluidic device of claim 8, further comprising a plurality of control channels, each formed within an elastomeric material and separated from one of the reaction chambers by an elastomeric membrane, the membrane being deflectable into one of the reaction chambers in response to an actuation force applied to the control channel; and
wherein the sample can be transported between the reaction chambers by actuation of the control channels.

10. The microfluidic device of claim 9, wherein the plurality of reaction chambers are in fluid communication such that substantially all of the sample within the plurality of reaction chambers is collected at one of the plurality of reaction chambers upon actuation of the control channels associated with the other reaction chambers.

11. The microfluidic device of claim 9, wherein there are three reaction chambers, each reaction chamber being in fluid communication with the other two chambers.

12. The microfluidic device of claim 8, further comprising an outlet that is in fluid communication with one of the plurality of reaction chambers, and wherein the inlet is in fluid communication with one of the plurality of reaction chambers.

13. The micro fluidic device of claim 1, wherein the temperature controller is selected from the group consisting of a Peltier device, a resistive heater, a heat exchanger and an indium tin oxide element.

14. The microfluidic device of claim 1, wherein a single temperature controller regulates temperature at all of the temperature regions.

15. The microfluidic device of claim 1, wherein the temperature controller is one of a plurality of temperature controllers, each temperature controller separately regulating temperature at a different temperature region.

16. The microfluidic device of claim 1, wherein one or more nucleic acids are immobilized within one or more of the temperature regions.

17. The microfluidic device of claim 1, wherein a polymerase is immobilized within one or more of the temperature regions.

18. The microfluidic device of claim 1, wherein there at least two temperature regions.

19. The microfluidic device of claim 18, wherein there are at least three temperature regions.

20. A microfluidic device, comprising
(a) a substantially circular microfabricated flow channel in fluid communication with an inlet;
(b) a plurality of temperature regions, each region located at a different location along the substantially circular flow channel; and
(c) a temperature controller operatively disposed to regulate the temperature within at least one of the plurality of temperature regions.

21. A method for conducting an analysis, the method comprising:
(a) providing a microfluidic device, comprising
(i) a substrate comprising an elastomeric material;
(ii) a flow channel disposed within the substrate, the flow channel
configured such that a sample introduced into the flow channel can be cycled around the flow channel; and
comprising a plurality of temperature regions at which temperature can be regulated, each temperature region located at a different location along the flow channel;
(b) introducing a sample into the flow channel; and
(c) transporting the sample between the different temperature regions.

22. The method of claim 21, wherein the flow channel is substantially circular.

23. The method of claim 21, wherein the microfluidic device further comprises a plurality of reaction chambers disposed along the flow channel and in fluid communication therewith, and wherein
each reaction chamber is located within one of the temperature regions; and
the transporting step comprises repeatedly transporting the sample through the plurality of reaction chambers.

24. The method of claim 21, wherein the sample is transported through two temperature regions, each at a different temperature.

25. The method of claim 21, wherein the sample is transported through at least three temperature regions, each at a different temperature.

26. The method of claim 21, wherein the sample comprises a target nucleic acid and the introducing step comprises introducing one or more components for conducting a nucleic acid amplification reaction.

27. The method of claim 26, wherein the sample and the one or more components are repeatedly transported through the flow channel, whereby the sample and the one or more components are exposed to the temperature regions multiple times and an amplified product is formed.

28. The method of claim 27, further comprising detecting the amplified product.

29. The method of claim 28, wherein the amplified product bears a detectable label and the detecting step comprises detecting the label.

30. The method of claim 29, wherein the label is selected from the group consisting of a fluorophore, a chromophore, a radioisotope, a luminescent agent, a mass label, an enzyme conjugated to a nucleic acid, and a magnetic agent.

31. The method of claim 28, wherein the detecting step comprises contacting the amplified product with a label such that the amplified product becomes labeled.

32. The method of claim 31, wherein the label is a interchelating dye.

33. The method of claim 31, wherein the label is a molecular beacon.

34. The method of claim 28, wherein the amplified product is detected by conducting a quantitative PCR assay.

35. The method of claim 28, wherein the amplified product is detected by conducting capillary gel electrophoresis.

36. The method of claim 28, wherein detecting comprises measuring capacitance of a solution containing amplified product.

37. The method of claim 28, wherein the microfluidic device further comprises a separation module in fluid communication with the flow channel, and wherein the method further comprises transporting a mixture containing amplified product from the flow channel to the separation module and separating amplified product from other components in the mixture prior to the detection step.

38. The method of claim 37, wherein separating comprises performing capillary gel electrophoresis.

39. The method of claim 27, wherein the sample comprises a plurality of target nucleic acids and a plurality of amplified products are formed.

40. The method of claim 39, wherein the plurality of amplified products are detected by differentially labeling the amplified products.

41. The method of claim 40, wherein the amplified products are differentially labeled by contacting the amplified products with a plurality of molecular beacons, each of the molecular beacons being complementary to a different amplified product.

42. The method of claim 39, wherein the amplified products are detected by conducting quantitative PCR with a plurality of sets of primers and probes, each set comprising a primer and probe complementary to a segment of one of the amplified products.

43. The method of claim 39, the method further comprising separating the plurality of extension products by capillary gel electrophoresis.

44. The method of claim 21, wherein a polymerase enzyme is immobilized within one or more of the temperature regions, whereby during transport the sample and the one or more components are brought into contact with the immobilized polymerase.

45. The method of claim 21, wherein the flow channel one or more nucleic acids are immobilized within one 6r more of the temperature regions such that when the sample is transported through the temperature regions the sample and the one or more components are brought into contact with the one or more nucleic, acids.

46. The method of claim 21, wherein the sample comprises a target nucleic acid and the introducing step comprises introducing one or more components for conducting a sequencing reaction.

47. The method of claim 21, wherein the sample comprises a target nucleic acid and the introducing step comprises introducing one or more components for conducting a quantitative PCR analysis.

48. The method of claim 21, wherein the microfluidic device further comprises a pump operatively connected to the flow channel, and the sample is repeatedly transported through the flow channel under the action of the pump.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:Taqman PCR
      beta-actin gene forward primer

<400> SEQUENCE: 1
tcacccacac tgtgcccatc tacga                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:Taqman PCR
      beta-actin gene reverse primer

<400> SEQUENCE: 2
cagcggaacc gctcattgcc aatgg                                              25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:Taqman PCR
      199-bp lambda phage DNA segment forward primer

<400> SEQUENCE: 3
ggttatcgaa atcagccaca gcgcc                                              25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Taqman PCR
      199-bp lambda phage DNA segment reverse primer

<400> SEQUENCE: 4
ggatacgtct gaactggtca c                                                  21